(12) United States Patent
Crowe et al.

(10) Patent No.: US 12,234,279 B2
(45) Date of Patent: *Feb. 25, 2025

(54) PEPTIDE CONSTRUCT HAVING A PROTEASE-CLEAVABLE LINKER

(71) Applicant: Sorriso Pharmaceuticals, Inc., San Diego, CA (US)

(72) Inventors: Scott Crowe, Babraham (GB); Mike West, Babraham (GB); Kevin Roberts, Babraham (GB)

(73) Assignee: SORRISO PHARMACEUTICALS, INC., San Diego, CA (US)

( * ) Notice: Subject to any disclaimer, the term of this patent is extended or adjusted under 35 U.S.C. 154(b) by 354 days.

This patent is subject to a terminal disclaimer.

(21) Appl. No.: 17/196,498

(22) Filed: Mar. 9, 2021

(65) Prior Publication Data

US 2021/0198345 A1 Jul. 1, 2021

Related U.S. Application Data

(63) Continuation of application No. 15/717,174, filed on Sep. 27, 2017, now abandoned, which is a continuation of application No. PCT/EP2016/057022, filed on Mar. 31, 2016.

(30) Foreign Application Priority Data

Mar. 31, 2015 (EP) .................... 15162112
Mar. 31, 2015 (EP) .................... 15162114
Mar. 31, 2015 (EP) .................... 15162115
Jan. 21, 2016 (EP) .................... 16152320

(51) Int. Cl.
*C07K 16/12* (2006.01)
*C07K 16/24* (2006.01)

(52) U.S. Cl.
CPC ........ *C07K 16/1282* (2013.01); *C07K 16/241* (2013.01); *C07K 2317/56* (2013.01); *C07K 2317/64* (2013.01); *C07K 2317/94* (2013.01); *C07K 2319/50* (2013.01)

(58) Field of Classification Search
None
See application file for complete search history.

(56) References Cited

U.S. PATENT DOCUMENTS

| | | | |
|---|---|---|---|
| 3,300,077 A | 1/1967 | David et al. | |
| 5,512,459 A * | 4/1996 | Wagner | C12P 21/02 435/68.1 |
| 5,780,028 A | 7/1998 | Graham | |
| 7,442,159 B1 * | 10/2008 | Riechmann | C40B 40/02 506/14 |
| 8,399,188 B2 | 3/2013 | Zhao et al. | |
| 8,697,654 B2 * | 4/2014 | Cheng | A61K 8/64 424/47 |
| 9,080,157 B2 | 7/2015 | Convents et al. | |
| 9,527,925 B2 | 12/2016 | Gschwind et al. | |
| 9,932,412 B2 | 4/2018 | Kim et al. | |
| 10,633,438 B2 | 4/2020 | Crowe et al. | |
| 10,772,839 B2 | 9/2020 | Crowe et al. | |
| 10,980,748 B2 | 4/2021 | Crowe et al. | |
| 11,623,952 B2 * | 4/2023 | Crowe | A61P 1/12 424/135.1 |
| 11,667,719 B2 * | 6/2023 | Crowe | C07K 16/2896 530/387.3 |
| 11,684,677 B2 * | 6/2023 | Crowe | A61K 9/0053 424/139.1 |
| 2004/0041867 A1 | 3/2004 | Lapstun et al. | |
| 2005/0147612 A1 | 7/2005 | Yayon et al. | |
| 2006/0034833 A1 | 2/2006 | Beirnaert | |
| 2006/0034845 A1 | 2/2006 | Silence et al. | |
| 2006/0057197 A1 | 3/2006 | Han et al. | |
| 2006/0138181 A1 | 6/2006 | Thom et al. | |
| 2007/0020267 A1 | 1/2007 | Fuh et al. | |
| 2007/0042399 A1 | 2/2007 | Wright et al. | |
| 2007/0077249 A1 | 4/2007 | Silence et al. | |
| 2007/0178082 A1 | 8/2007 | Silence et al. | |
| 2007/0237769 A1 | 10/2007 | Silence et al. | |
| 2008/0026820 A1 | 1/2008 | Okada | |
| 2008/0031770 A1 | 2/2008 | Heselton et al. | |
| 2008/0039761 A1 | 2/2008 | Heaton et al. | |
| 2008/0122965 A1 | 5/2008 | Fang | |
| 2008/0145420 A1 | 6/2008 | Simon | |
| 2008/0149143 A1 | 6/2008 | Chou et al. | |

(Continued)

FOREIGN PATENT DOCUMENTS

| | | |
|---|---|---|
| AU | 2014214850 A1 | 8/2015 |
| CA | 2817265 A1 | 10/2004 |

(Continued)

OTHER PUBLICATIONS

Yusakul et al., Bioscience, Biotechnology and Biochemistry 80(7): 1306-1312 (Year: 2016).*
Barata et al. Flip the coin: IL-7 and IL-7R in health and disease. Nat Immunol 20(12):1584-1593 (2019).
Lee et al. Anti-IL-7 receptor-α reverses established type 1 diabetes in nonobese diabetic mice by modulating effector T-cell function. PNAS USA 109(31):12674-12679 (2012).

(Continued)

*Primary Examiner* — Phuong Huynh
(74) *Attorney, Agent, or Firm* — WILSON SONSINI GOODRICH & ROSATI

(57) ABSTRACT

There is provided inter alia a construct suitable for oral administration comprising a first polypeptide and a second polypeptide connected by a labile peptide linker, wherein the labile peptide linker is labile to one or more proteases present in the intestinal tract and wherein the first and second polypeptides are substantially resistant to said one or more proteases.

16 Claims, 8 Drawing Sheets

Specification includes a Sequence Listing.

(56) References Cited

U.S. PATENT DOCUMENTS

| | | |
|---|---|---|
| 2008/0260820 A1 | 10/2008 | Borrelly et al. |
| 2009/0064457 A1 | 3/2009 | Brustle |
| 2009/0064460 A1 | 3/2009 | Tang et al. |
| 2010/0077422 A1 | 3/2010 | Bushinsky |
| 2010/0137213 A1 | 6/2010 | Fernandez et al. |
| 2010/0239682 A1 | 9/2010 | Andremont et al. |
| 2010/0260857 A1 | 10/2010 | Fallon et al. |
| 2011/0028695 A1 | 2/2011 | Revets et al. |
| 2011/0098518 A1 | 4/2011 | Minoux et al. |
| 2011/0109365 A1 | 5/2011 | Mai |
| 2011/0112229 A1 | 5/2011 | Nagaoka et al. |
| 2011/0229476 A1 | 9/2011 | Liu et al. |
| 2012/0130872 A1 | 5/2012 | Baughman et al. |
| 2012/0151199 A1 | 6/2012 | Shriver |
| 2013/0173687 A1 | 7/2013 | Tuchman et al. |
| 2014/0030049 A1 | 1/2014 | Imai et al. |
| 2014/0044730 A1 | 2/2014 | Yancopoulos et al. |
| 2014/0141152 A1 | 5/2014 | Sostek et al. |
| 2014/0170212 A1 | 6/2014 | Ortenzi et al. |
| 2014/0186365 A1 | 7/2014 | Robinson et al. |
| 2014/0294826 A1 | 10/2014 | Shoemaker |
| 2014/0377287 A1 | 12/2014 | Govindan et al. |
| 2015/0017183 A1 | 1/2015 | Seidah et al. |
| 2015/0058173 A1 | 2/2015 | Schmeling et al. |
| 2015/0147318 A1 | 5/2015 | Bergeron et al. |
| 2015/0176031 A1 | 6/2015 | Streffer |
| 2015/0337035 A1 | 11/2015 | Anderson et al. |
| 2016/0060338 A1 | 3/2016 | Barrett et al. |
| 2016/0156465 A1 | 6/2016 | Vaikuntanathan et al. |
| 2016/0264659 A1 | 9/2016 | Heavner et al. |
| 2017/0002069 A1 | 1/2017 | Crowe et al. |
| 2017/0022271 A1 | 1/2017 | Hoffman et al. |
| 2017/0260266 A1 | 9/2017 | Ahmed et al. |
| 2018/0009881 A1 | 1/2018 | Crowe et al. |
| 2018/0037639 A1 | 2/2018 | Crowe et al. |
| 2018/0100008 A1 | 4/2018 | Crowe et al. |
| 2018/0100009 A1 | 4/2018 | Crowe et al. |
| 2019/0008778 A1 | 1/2019 | Crowe et al. |
| 2019/0040156 A1 | 2/2019 | Demarest et al. |
| 2019/0092855 A1 | 3/2019 | Crowe et al. |
| 2019/0137495 A1 | 5/2019 | Shaked et al. |
| 2019/0307891 A1 | 10/2019 | Crowe et al. |
| 2020/0079844 A1 | 3/2020 | Beirnaert |
| 2020/0317769 A1 | 10/2020 | Crowe et al. |
| 2021/0317195 A1 | 10/2021 | Crowe et al. |
| 2022/0242945 A1* | 8/2022 | Crowe .................. C07K 16/241 |
| 2022/0332810 A1 | 10/2022 | Crowe et al. |
| 2022/0363769 A1 | 11/2022 | Crowe et al. |
| 2023/0056445 A1* | 2/2023 | Crowe .................... A61P 37/02 |
| 2023/0143091 A1* | 5/2023 | Crowe .................... A61P 29/00 424/158.1 |
| 2023/0287098 A1* | 9/2023 | Crowe .................... A61P 29/00 |
| 2024/0277864 A1 | 8/2024 | Crowe et al. |

FOREIGN PATENT DOCUMENTS

| | | | |
|---|---|---|---|
| CN | 1809383 A | | 7/2006 |
| CN | 101128182 A | | 2/2008 |
| CN | 102090373 A | | 6/2011 |
| CN | 102388069 A | | 3/2012 |
| CN | 102971341 A | | 3/2013 |
| CN | 103703129 A | | 4/2014 |
| CN | 106715471 A | | 5/2017 |
| EP | 2275443 A1 | | 1/2011 |
| EP | 2275443 B1 | | 12/2015 |
| EP | 2955196 A1 | | 12/2015 |
| WO | WO-9102078 A1 | | 2/1991 |
| WO | WO-9201047 A1 | | 1/1992 |
| WO | WO-9300077 A1 | | 1/1993 |
| WO | WO-9404678 A1 | | 3/1994 |
| WO | WO-9425591 A1 | | 11/1994 |
| WO | WO-9508562 A1 | | 3/1995 |
| WO | WO-9634103 A1 * | 10/1996 | ............. C07K 16/00 |
| WO | WO-9923221 A2 | | 5/1999 |
| WO | WO-0212502 A2 | | 2/2002 |
| WO | WO-0248382 A2 | | 6/2002 |
| WO | WO-03035694 A2 | | 5/2003 |
| WO | WO-2004009776 A2 | | 1/2004 |
| WO | WO-2004037205 A2 | | 5/2004 |
| WO | WO-2004041862 A2 | | 5/2004 |
| WO | WO-2004041863 A2 | | 5/2004 |
| WO | WO-2004041865 A2 | | 5/2004 |
| WO | WO-2004041867 A2 | | 5/2004 |
| WO | WO-2006056306 A2 | | 6/2006 |
| WO | WO-2006071877 A2 | | 7/2006 |
| WO | WO-2006122786 A2 | | 11/2006 |
| WO | WO-2006122787 A1 | | 11/2006 |
| WO | WO-2006138181 A2 | | 12/2006 |
| WO | WO-2007005955 A2 | | 1/2007 |
| WO | WO-2007025977 A2 | | 3/2007 |
| WO | WO-2007027714 A2 | | 3/2007 |
| WO | WO-2007048022 A2 | | 4/2007 |
| WO | WO-2007070948 A1 | | 6/2007 |
| WO | WO-2007104529 A2 | | 9/2007 |
| WO | WO-2008020079 A1 | | 2/2008 |
| WO | WO-2008031770 A2 | | 3/2008 |
| WO | WO-2008039761 A2 | | 4/2008 |
| WO | WO-2008049897 A1 | | 5/2008 |
| WO | WO-2008074840 A2 | | 6/2008 |
| WO | WO-2008101985 A2 | | 8/2008 |
| WO | WO-2008101985 A3 | | 10/2008 |
| WO | WO-2008122965 A2 | | 10/2008 |
| WO | WO-2008124170 A2 | | 10/2008 |
| WO | WO-2008144753 A2 | | 11/2008 |
| WO | WO-2008124170 A3 | | 12/2008 |
| WO | WO-2008149143 A2 | | 12/2008 |
| WO | WO-2009021754 A2 | | 2/2009 |
| WO | WO-2008149143 A3 | | 4/2009 |
| WO | WO-2009046168 A1 | | 4/2009 |
| WO | WO-2009064457 A2 | | 5/2009 |
| WO | WO-2009064460 A2 | | 5/2009 |
| WO | WO-2009068627 A2 | | 6/2009 |
| WO | WO-2009147248 A2 | | 12/2009 |
| WO | WO-2010020811 A1 | | 2/2010 |
| WO | WO-2010045506 A2 | | 4/2010 |
| WO | WO-2010056550 A1 | | 5/2010 |
| WO | WO-2010045506 A3 | | 7/2010 |
| WO | WO-2010077422 A2 | | 7/2010 |
| WO | WO-2010085643 A1 | | 7/2010 |
| WO | WO-2010115998 A2 | | 10/2010 |
| WO | WO-2011009365 A1 | | 1/2011 |
| WO | WO-2011083175 A1 | | 7/2011 |
| WO | WO-2011094259 A2 | | 8/2011 |
| WO | WO-2011098518 A2 | | 8/2011 |
| WO | WO-2011104687 A1 | | 9/2011 |
| WO | WO-2011112229 A2 | | 9/2011 |
| WO | WO-2011135026 A1 | | 11/2011 |
| WO | WO-2011135040 A1 | | 11/2011 |
| WO | WO-2011139269 A1 | | 11/2011 |
| WO | WO-2011139629 A2 | | 11/2011 |
| WO | WO-2012007880 A2 | | 1/2012 |
| WO | WO-2011139629 A3 | | 4/2012 |
| WO | WO-2012055030 A1 | | 5/2012 |
| WO | WO-2012078878 A2 | | 6/2012 |
| WO | WO-2012130872 A1 | | 10/2012 |
| WO | WO-2012131053 A1 | | 10/2012 |
| WO | WO-2012151199 A1 | | 11/2012 |
| WO | WO-2012175741 A2 | | 12/2012 |
| WO | WO-2013024059 A2 | | 2/2013 |
| WO | WO-2013056984 A1 | | 4/2013 |
| WO | WO-2013058833 A1 | | 4/2013 |
| WO | WO-2013064701 A2 | | 5/2013 |
| WO | WO-2013087857 A2 | | 6/2013 |
| WO | WO-2013087874 A1 | | 6/2013 |
| WO | WO-2013091103 A1 | | 6/2013 |
| WO | WO-2013173687 A1 | | 11/2013 |
| WO | WO-2013184871 A1 | | 12/2013 |
| WO | WO-2014030049 A2 | | 2/2014 |
| WO | WO-2014058875 A3 | | 6/2014 |
| WO | WO-2014141152 A2 | | 9/2014 |
| WO | WO-2015009996 A1 | | 1/2015 |
| WO | WO-2015058173 A1 | | 4/2015 |
| WO | WO-2015065987 A1 | | 5/2015 |

(56) References Cited

FOREIGN PATENT DOCUMENTS

| WO | WO-2015100409 A2 | 7/2015 |
|---|---|---|
| WO | WO-2015144852 A1 | 10/2015 |
| WO | WO-2015176031 A2 | 11/2015 |
| WO | WO-2015189302 A1 | 12/2015 |
| WO | WO-2016065323 A2 | 4/2016 |
| WO | WO-2016103093 A1 | 6/2016 |
| WO | WO-2016156465 A1 | 10/2016 |
| WO | WO-2016156466 A1 | 10/2016 |
| WO | WO-2016162537 A1 | 10/2016 |
| WO | WO-2016202411 A1 | 12/2016 |
| WO | WO-2016202414 A1 | 12/2016 |
| WO | WO-2016202415 A1 | 12/2016 |
| WO | WO-2018060453 A1 | 4/2018 |
| WO | WO-2018104483 A1 | 6/2018 |
| WO | WO-2020254826 A1 | 12/2020 |
| WO | WO-2020254827 A1 | 12/2020 |
| WO | WO-2020254828 A1 | 12/2020 |

OTHER PUBLICATIONS

Marković et al. Modulation of Signaling Mediated by TSLP and IL-7 in Inflammation, Autoimmune Diseases, and Cancer. Front Immunol 11:1557 (2020).
Gomes, A., et al., "Comparison of Yeasts as Hosts for Recombinant Protein Production," Microorganisms 6.2 (2018): 38, 23 pages.
Hu, G., et al., "A phylogenomic approach to reconstructing the diversification of serine proteases in fungi." Journal of evolutionary biology 17.6 (2004): 1204-1214.
Muszewska, A., et al., "Fungal lifestyle reflected in serine protease repertoire." Scientific Reports 7.1 (2017): 1-12.
Casset et al. A peptide mimetic of an anti-CD4 monoclonal antibody by rational design. Biochemical and Biophysical Research Communication 307:198-205 (2003).
Chen et al. Enhancement and destruction of antibody function U by somatic mutation: unequal occurrence is controlled by V gene combinatorial associations. The EMBO Journal 14(12):2784-2794 (1995).
MacCallum et al.: Antibody-antigen interactions: contact analysis and binding site topography. J Mol Biol. 262(5):732-745 (1996).
U.S. Appl. No. 16/821,287 Office Action dated Oct. 21, 2022.
U.S. Appl. No. 17/752,710 Office Action dated Nov. 4, 2022.
Arbabi-Ghahroudi et al. Selection and identification of single domain antibody fragments from camel heavy-chain antibodies. FEBS Letters 414(3):521-526 (1997).
Baumgart et al. Crohn's disease. Lancet 380(9853):1590-1605 (2012).
Bendig. Humanization of Rodent Monoclonal Antibodies by CDR Grafting. Methods A Companion to Methods in Enzymology. 8:83-93 (1995).
Biancheri et al. Proteolytic cleavage and loss of function of biologic agents that neutralize tumor necrosis factor in the mucosa of patients with inflammatory bowel disease. Gastroenterology 149(6):1564-1574 (2015).
Binz et al. Designing repeat proteins: well-expressed, soluble and stable proteins from combinatorial libraries of consensus ankyrin repeat proteins. J. Mol. Biology 332(2):489-503 (2003).
Blattler et al. New heterobifunctional protein crosslinking reagent that forms an acid-labile link. Biochemistry 24(6):1517-1524 (1985).
Bruno, et al. Basics and recent advances in peptide and protein drug delivery. Ther Deliv. 4(11):1443-67 (2013).
Chen et al. Fusion Protein Linkers: Property, Design and Functionality. Adv Drug Deliv Rev 65:1357-1369 (2013). Available online Sep. 29, 2012.
Chomczynski, et al. Single-step method of RNA isolation by acid guanidinium thiocyanate-phenol-chloroform extraction. Anal Biochem. 162(1):156-9 (1987).
Colman et al., Effects of amino acid sequence changes on antibody-antigen interactions, Research in Immunology 145(1):33-36 (1994).

Coppieters et al. Formatted anti-tumor necrosis factor alpha VHH proteins derived from camelids show superior potency and targeting to inflamed joints in a murine model of collagen-induced arthritis. Arthritis Rheum 54(6): 1856-1866 (2006).
Crowe et al. Gastrointestinal Stability and Tissue Penetration of V565: a Novel Orally Administered Anti-TNFa Vorabody™. Poster from 10th Annual Proteins and Antibodies Congress [1] (2017).
Crowe et al. Gastrointestinal Stability and Tissue Penetration of V565: A Novel Orally Administered Anti-TNFa Vorabody™. Vhsquared, Poster from PEGS Europe Protein and Antibody Engineering Summit, Lisbon, Portugal [1] (2017).
Crowe et al. Oral Delivery of a Novel Engineered Anti TNFa Domain Antibody (Vorabody™) for the Treatment of Intestinal Bowel Disease. PEGS Europe Protein & Antibody Engineering Summit [1] (2017).
Crowe et al. Preclinical Assessment of a Novel Anti-TNFa Vorabody™ as an Oral Therapy for Crohn's Disease. 18th International Congress of Mucosal Immunology, Washington D.C. [1] (2017).
Crowe et al: Preclinical Development of a Novel, Orally-Administered Anti-Tumour Necrosis Factor Domain Antibody for the Treatment of Inflammatory Bowel Disease. Scientific Reports 8:4941 [1-13] (2018).
Danese: New therapies for inflammatory bowel disease: from the bench to the bedside. Gut 61(6):918-932 (2012).
Deschacht et al. A novel promiscuous class of camelid single-domain antibody contributes to the antigen-binding repertoire. J. Immmunol 184(10):5696-5704 (2010).
Faisst et al. Isolation of a fully infectious variant of parvovirus H-1 supplanting the standard strain in human cells. Journal of Virology 69(7):4538-4543 (1995).
Fields et al. Dual-attribute continuous monitoring of cell proliferation/cytotoxicity. Am Biotechnol Lab 11(4):48-50 (1993).
Frenken et al. Isolation of antigen specific llama VHH antibody fragments and their high level secretion by *Saccharomyces cerevisiae*. J Biotechnol 78(1):11-21 (2000).
Giusti et al. Somatic diversification of S107 from an antiphosphocholine to an anti-DNA autoantibody is due to a single base change in its heavy chain variable region. PNAS USA 84(9):2926-30 (1987).
Griffiths et al. Shark Variable New Antigen Receptor (VNAR) Single Domain Antibody Fragments: Stability and Diagnostic Applications. Antibodies 2(1):66-81 (2013).
Grundstrom et al. Oligonucleotide-directed mutagenesis by microscale 'shot-gun' gene synthesis. Nucleic Acids Research 13(9):3305-3316 (1985).
Hamers-Casterman et al. Naturally occurring antibodies devoid of light chains. Nature 363(6428):446-8 (1993).
Harmsen et al. Effect of a pmr 1 disruption and different signal sequences on the intracellular processing and secretion of Cyamopsis tetragonoloba alpha-galactosidase by *Saccharomyces cerevisiae*. Gene 125(2):115-123 (1993).
Harmsen et al. Properties, production, and applications of camelid single-domain antibody fragments. Appl. Microbiol. Biotechnol. 77:13-22 (2007).
Harmsen et al. Selection and Optimization of Proteolytically Stable Llama Single-Domain Antibody Fragments for Oral Immunotherapy. Applied Microbiology and Biotechnology 72(3):544-551 (2006).
Hashimoto et al. Effects of signal sequences on the secretion of hen lysozyme by yeast: construction of four secretion cassette vectors. Protein Engineering 11(2):75-77 (1998).
Hendrickson et al. Clinical aspects and pathophysiology of inflammatory bowel disease. Clinical Microbiology Reviews 15(1):79-94 (2002).
Hoogenboom et al. Multi-subunit proteins on the surface of filamentous phage: methodologies for displaying antibody (Fab) heavy and light chains. Nucleic Acids Res. 19(15):4133-4137 (1991).
Horwitz et al. Secretion of functional antibody and Fab fragment from yeast cells. Proc. Natl. Acad. Sci. U.S.A. 85(22):8678-8682 (1988).
Humphreys et al. Modes of L929 cell death induced by TNF-alpha and other cytotoxic agents. Cytokine 11(10):773-782 (1999).
Huse et al. Generation of a large combinatorial library of the immunoglobulin repertoire in phage lambda. Science 246(4935):1275-1281 (1989).

(56) References Cited

OTHER PUBLICATIONS

Hussack et al. Engineered Single-Domain Antibodies with High Protease Resistance and Thermal Stability. PLoS One. 6(11):e28218 (2011).
Hussack et al. Isolation and characterization of Clostridium difficile toxin-specific single-domain antibodies. Methods Mol Biol. 911:211-239 (2012).
Hussack et al. Neutralization of Clostridium difficile toxin A with single-domain antibodies targeting the cell receptor binding domain. J. Biol. Chem. 286(11):8961-8976 (2011).
Hussack et al. Protease-resistant single-domain antibodies inhibit Campylobacter jejuni motility. Protein Eng Des Sel. 27(6):191-198 (2014).
Hussack et al. Single-domain Antibody Inhibitors of Clostridium difficile Toxins. Thesis submitted to the Faculty of Graduate and Postdoctoral Studies, Dept. of Biochemistry, Microbiology and Immunology [1-227] (2011).
Hussack: Single-domain Antibody Inhibitors of Clostridium difficile Toxins. Universite d'Ottawa website [1-3] (2013)https://ruor.uottawa.ca/handle/10393/20362.
Kabat et al. Sequences of proteins of immunological interest. NIH Publ. No. 91-3242 1:647-669 (1991).
Kamm et al. Practical application of anti-TNF therapy for luminal Crohn's disease. Inflammatory Bowel Diseases. 17(11):2366-2391 (2011).
Khantasup et al. Design and Generation of Humanized Single-chain Fv Derived from Mouse Hybridoma for Potential Targeting Application. Monoclon Antib Immunodiagn Immunother. 34(6):404-17 (2015).
Kim et al. A Dual Target-directed Agent against Interleukin-6 Receptor and Tumor Necrosis Factor α ameliorates experimental arthritis. Scientific Reports 6:20150 doi: 10.1038/srep20150 [1-12] (2015).
Kim et al. Antibody light chain variable domains and their biophysically improved versions for human immunotherapy. Mabs. 6(1):219-235 (2014).
Kohler et al. Continuous cultures of fused cells secreting antibody of predefined specificity. Nature256(5517):495-497 (1975).
Ling et al. Approaches to DNA Mutagenesis: An Overview. Analytical Biochemistry 254(2):157-178 (1997).
Liu et al. Targeting TNF-alpha with a tetravalent mini-antibody TNF-TeAb. Biochemical Journal 406(2):237-246 (2007).
Lopes et al. Mechanism of high-copy-number integration of pMIRY-type vectors into the ribosomal DNA of *Saccharomyces cerevisiae*. Gene. 105(1):83-90 (1991).
McCoy et al. Neutralisation of HIV-1 cell-cell spread by human and llama antibodies. Retrovirology 11:83 doi:10.1186/s12977-014-0083-y [1-15] (2014).
Merchlinksy et al. Construction of an infectious molecular clone of the autonomous parvovirus minute virus of mice. Journal of Virology 47(1):227-232 (1983).
Miethe et al. Production of Single Chain Fragment Variable (scFv) Antibodies in *Escherichia coli* Using the LEX TM Bioreactor. Journal of Biotechnology 163(2):105-111 (2012).
Molhoj, et al. CD19-/CD3-bispecific antibody of the BiTE class is far superior to tandem diabody with respect to redirected tumor cell lysis. Mol Immunol. 44(8):1935-43 (2007).
Muyldermans. Nanobodies: natural single-domain antibodies. Annu Rev Biochem 82:775-797 (2013).
Muyldermans et al. Sequence and structure of VH domain from naturally occurring camel heavy chain immunoglobulins lacking light chains. Protein Engineering 7(9):1129-1133 (1994).
Nambiar, et al. Total synthesis and cloning of a gene coding for the ribonuclease S protein. Science 223(4642):1299-301 (1984).
Nelson et al. Nonoclonal antibodies. Molecular Pathology 53(3):111-117 (2000).
Nguyen et al. Functional heavy-chain antibodies in Camelidae. Adv Immunol 79:261-296 (2001).
Nogi et al. Nucleotide sequence of the transcriptional initiation region of the yeast GAL7 gene. Nucleic Acid Research 11(24):8555-8568 (1983).
Nurbhai et al. Measured and Modelled Data Suggest That Oral Administration of V565, A Novel Domain Antibody to TNF-alpha, Could be Beneficial in the Treatment of IBD. 13th Congress of ECCO, Vienna, Austria, 1 page (2018).
Ortonne. Recent developments in the understanding of the pathogenesis of psoriasis. British Journal of Dermatology 140(Suppl 54):1-7 (1999).
Padlan. Anatomy of the Antibody Molecule. Mol Immunol 31(3):169-217 (1994).
Patnaik et al. Penicillin fermentation: mechanisms and models for industrial-scale bioreactors. Crit Rev Biotechnol 20:1-15 (2015).
Paul. Fundamental Immunology. 3rd Edition, pp. 292-295, Raven Press (1993).
PCT/EP2016/057021 International Search Report and Written Opinion dated Aug. 8, 2016.
PCT/EP2016/057022 International Search Report and Written Opinion dated Jun. 14, 2016.
PCT/EP2016/057032 International Search Report and Written Opinion dated Aug. 4, 2016.
PCT/EP2016/057034 International Search Report and Written Opinion dated Aug. 3, 2016.
Robinson et al. A Protease-Resistant Oral Domain Antibody to TNFα Delivers High Concentrations of Active Compound in Ileal Fluid of Subjects with an Ileostomy. 25th United European Gastroenterology Week, Barcelona, Spain [1] (2017).
Rose-John: IL-6 trans-signaling via the soluble IL-6 receptor: importance for the pro-inflammatory activities of IL-6. Int. J. Biol. Sci. 8(9):1237-1247 (2012).
Roux et al. Structural analysis of the nurse shark (new) antigen receptor (NAR): molecular convergence of NAR and unusual mammalian immunoglobulins. PNAS USA 95(20):11804-11809 (1998).
Rudikoff et al. Single amino acid substitution altering antigen-binding Specificity. PNAS USA 79:1979-1983 (1982).
Sakmar et al. Total synthesis and expression of a gene for the alpha-subunit of bovine rod outer segment guanine nucleotide-binding protein (transducin). Nucleic Acids Research 16(14A):6361-6372 (1988).
Shaji, et al. Protein and Peptide drug delivery: oral approaches. Indian J Pharm Sci. 70(3):269-77 (2008).
Shealy et al. Characterization of golimumab, a human monoclonal antibody specific for human tumor necrosis factor a. MAbs 2(4):428-439 (2010).
Siontorou: Nanobodies as novel agents for disease diagnosis and therapy. Int J Nanomedicine 8:4215-4227 (2013).
Skerra et al. Assembly of a functional Immunoglobulin Fv fragment in *Escherichia coli*. Science 240(4855):1038-1041 (1988).
STIC report (2019).
Tanha et al. Selection by phage display of llama conventional V(H) fragments with heavy chain antibody V(H)H properties. Journal of Immunological Methods 263(1-2):97-109 (2002).
Thomassen et al. Large-scale production of VHH antibody fragments by *Saccharomyces cerevisiae*. Enzyme and Microbial Technology 30(3):273-278 (2002).
Unger et al. Selection of nanobodies that block the enzymatic and cytotoxic activities of the binary Clostridium difficile toxin CDT. Scientific Reports 5:7850 [1-10] (2015).
UniProt Database: Uncharacterized protein. Accession No. B5H131, 2 pages (2008) http://www.uniprot.org/uniprot/B5H131.
U.S. Appl. No. 15/717,174 Office Action dated Apr. 22, 2020.
U.S. Appl. No. 15/717,174 Office Action dated Aug. 8, 2019.
U.S. Appl. No. 15/717,174 Office Action dated Mar. 6, 2019.
U.S. Appl. No. 15/717,174 Office Action dated Sep. 16, 2020.
Vandenbroucke et al. Orally administered L. lactis secreting an anti-TNF nanobody demonstrate efficacy in chronic colitis. Mucosal Immunology 3(1):49-56 (2010).
Vandeventer: Anti-TNF antibody treatment of Crohn's disease. Ann Rheum Dis. 58(Suppl I):1114-1120 (1999).
Verma et al. Modified oligonucleotides: synthesis and strategy for users. Annu Rev Biochem 67:99-134 (1998).

(56) References Cited

OTHER PUBLICATIONS

Volkel et al. Optimized linker sequences for the expression of monomeric and dimeric bispecific single-chain diabodies. Protein Eng. 14(10):815-823 (2001).
Vu et al. Comparison of llama VH sequences from conventional and heavy chain antibodies. Molecular Immunology 34(16-17):1121-1131 (1997).
Wahlich et al. Oral Delivery of a Novel Domain Antibody (VorabodyTM) for the Treatment of Chron's Disease. PEGS Europe Protein & Antibody Engineering Summit, Lisbon, Portugal, 1 page (2017).
Ward et al. Binding activities of a repertoire of single immunoglobulin variable domains secreted from *Escherichia coli*. Nature 341(6242):544-546 (1989).
Wells et al. Cassette mutagenesis: an efficient method for generation of multiple mutations at defined sites. Gene 34:315-323 (1985).
West et al. Predicting intestinal tract luminal concentrations after oral dosing of an anti-TNFa domain antibody engineered for intestinal protease resistance. VHsquared Antibody Engineering & Therapeutics Meeting, San Diego, USA, 1 page (2017).
Yan et al. Construction of a synthetic phage-displayed Nanobody library with CDR3 regions randomized by trinucleotide cassettes for diagnostic applications. Journal of Translational Medicine 12:343. doi: 10.1186/s12967-014-0343-6. [1-12] (2014).
Yu et al., Interaction between Bevacizumab and Murine VEGF-A: A Reassessment, Investigative Ophthalmology & Visual Science 49(2):522-527 (2008).
Zabetakis et al. Contributions of the complementarity determining regions to the thermal stability of a single-domain antibody. PLoS One 8(10):e77678 (2013).
2005 Drug Bank Data (https://wwwdrugbank.caldrugs/DB00085) for Pancrelipase.
Biancheri et al. Differential Cleavage of Anti-Tumor Necrosis Factor-Alpha Agents by Matrix Metalloproteinase (MMP)-10 and MMP-12 in Inflammatory Bowel Disease. ECCO, Abstract, 1 page, Dublin (2011).
Bjerkan et al. Multiple Functions of the New Cytokine-Based Antimicrobial Peptide Thymic Stromal Lymphopoietin (TSLP). Pharmaceuticals (Basel) 9(3):E41 (2016).
Bruno et al.: Basics and recent advances in peptide and protein drug delivery. Ther Deliv. 4(11):1443-1467 (2013).
Caldas et al. Humanization of the anti-CD18 antibody 6.7: an unexpected effect of a framework residue in binding to antigen. Mol Immunol. 39(15):941-952 (2003).
Cianferoni et al. Eosinophilic Esophagitis and Gastroenteritis. Curr Allergy Asthma Rep. 15(9):58 (2015).
Colombel et al. Adalimumab for maintenance of clinical response and remission in patients with Crohn's disease: the Charm trial. Gastroenterology 132:52-65 (2007).
Corren et al. Tezepelumab in Adults with Uncontrolled Asthma. N Engl J Med. 377(10):936-946 (2017).
Crawley et al. Soluble IL-7R alpha (sCD127) inhibits IL-7 activity and is increased in HIV infection. J Immunol. 184(9):4679-4687 (2010).
Croxford et al. IL-23: one cytokine in control of autoimmunity. Eur J Immunol. 42:2263-2273 (2012).
Desmet et al. Structural basis of IL-23 antagonism by an Alphabody protein scaffold. Nature Communications 5:5237 (2014).
Desmyter et al.: Neutralization of Human Interleukin 23 by Multivalent Nanobodies Explained by the Structure of Cytokine-Nanobody Complex. Front Immunol. 8:884 (2017).
Dooms. Interleukin-7: Fuel for the autoimmune attack. J Autoimmun. 45:40-48 (2013).
Ebersbach et al.: Affilin-novel binding molecules based on human gamma-B-crystallin, an all beta-sheet protein. J. Molecular Biology 372(1):172-185 (2007).
Eken et al. Interleukin 23 in Crohn's disease. Inflamm Bowel Dis. 20:587-595 (2014).

Ellis et al. Anti-IL-7 receptor α monoclonal antibody (GSK2618960) in healthy subjects—a randomized, double-blind, placebo-controlled study. Br J Clin Pharmacol. 85(2):304-315 (2019).
Fadda et al.: Physiological bicarbonate buffers: stabilisation and use as dissolution media for modified release systems. Int. J. Pharm. 382(1-2):56-60 (2009).
Fornasa et al. Dichotomy of short and long thymic stromal lymphopoietin isoforms in inflammatory disorders of the bowel and skin. J Allergy Clin Immunol. 136(2):413-422 (2015).
Fry et al. Interleukin-7: from bench to clinic. Blood 99(11):3892-3904 (2002).
Fry et al. The many faces of IL-7: from lymphopoiesis to peripheral T cell maintenance. J Immunol. 174(11):6571-6576 (2005).
Furfaro et al. IL-23 Blockade for Crohn's disease: next generation of anti-cytokine therapy. Expert Rev Clin Immunol. 13:457-467 (2017).
Garbacz et al.: A dynamic system for the simulation of fasting luminal pH-gradients using hydrogen carbonate buffers for dissolution testing of ionisable compounds. Eur J Pharm Sci. 51:224-231 (2014).
Goldberg et al.: Engineering a targeted delivery platform using Centyrins. Protein Eng Des Sel. 29(12):563-572 (2016).
Goldberg et al. The unusual suspects—innate lymphoid cells as novel therapeutic targets in IBD. Nat Rev Gastroenterol Hepatol (5):271-283 (2015).
Goyanes et al.: Gastrointestinal release behaviour of modified-release drug products: dynamic dissolution testing of mesalazine formulations. Int. J. Pharm. 484(1-2):103-108 (2015).
Grabulovski et al. A novel, non-immunogenic Fyn SH3-derived binding protein with tumor vascular targeting properties. J Biol Chem. 282(5):3196-3204 (2007).
Guerra et al.: Management of inflammatory bowel disease in poor responders to infliximab. Clin Exp Gastroenterol 7:359-367 (2014).
Hafler et al. Risk alleles for multiple sclerosis identified by a genomewide study. N Engl J Med. 357(9):851-862 (2007).
Hanauer et al. Human anti-tumor necrosis factor monoclonal antibody (adalimumab) in Crohn's disease: the Classic-I trial. Gastroenterology 130:323-333 (2006).
Hanauer et al., Maintenance infliximab for Crohn's disease: the Accent I randomized trial. Lancet 359:1541-1549 (2002).
Henikoff et al. Amino acid substitution matrices from protein blocks. PNAS USA 89(22):10915-10919 (1992).
Heninger et al. IL-7 abrogates suppressive activity of human CD4+CD25+FOXP3+ regulatory T cells and allows expansion of alloreactive and autoreactive T cells. J Immunol. 189(12):5649-5658 (2012).
Hoefman et al.: Pre-Clinical Intravenous Serum Pharmacokinetics of Albumin Binding and Non-Half-Life Extended Nanobodies(R). Antibodies 4(3):141-156 (2015).
Hussack et al: A V(L) single-domain antibody library shows a high-propensity to yield non-aggregating binders. Protein Eng Des Sel. 25(6):313-318 (2012).
Hussan et al. A review on recent advances ofenteric coating. IOSR J Pharm 2(6):5-11 (2012).
Johnson et al.: Sensitive affimer and antibody based impedimetric label-free assays for c-reactive protein. Analytical Chemistry 84(15):6553-6560 (2012).
Jones et al.: Targeted localized use of therapeutic antibodies: a review of non-systemic, topical and oral applications. Crit Rev Biotechnol 36(3):506-520 (2015).
Karlin, et al. Applications and statistics for multiple high-scoring segments in molecular sequences. PNAS USA 90:5873-5877 (1993).
Knezevic et al. Quantitation of affinity, avidity, and binding kinetics of protein analytes with a dynamically switchable biosurface. J Am Chem Soc 134(37):15225-15228 (2012).
Koide et al. Monobodies: antibody mimics based on the scaffold of the fibronectin type III domain. Methods in Molecular Biology 352:95-111 (2007).
Krehenbrink et al.: Artificial binding proteins (Affitins) as probes for conformational changes in secretin PuID. J Mol Biol. 383(5):1058-1068 (2008).
Lipovsek: Adnectins: engineered target-binding protein therapeutics. Protein Engineering, Design & Selection 24(1-2):3-9 (2011).

(56) References Cited

OTHER PUBLICATIONS

Liu et al. Crucial role of interleukin-7 in T helper type 17 survival and expansion in autoimmune disease. Nat Med. 16(2):191-197 (2010) (retraction in: Nat Med. 2013 19(12):1673).
Liu. Thymic stromal lymphopoietin: master switch for allergic inflammation. J Exp Med 203(2):269-273 (2006).
McGovern et al. The IL23 axis plays a key role in the pathogenesis of IBD. Gut 56:1333-1336 (2007).
Merchant et al.: Predicting the gastrointestinal behaviour of modified-release products: utility of a novel dynamic dissolution test apparatus involving the use of bicarbonate buffers. Int. J. Pharm. 475(1-2):585-591 (2014).
Michael. The role of digestive enzymes in orally induced immune tolerance. Immunol Invest. 18(9-10):1049-1054 (1989) (Abstract).
Nixon et al. Engineered protein inhibitors of proteases. Curr Opin Drug Discov Devel. 9(2):261-268 (2006).
Noti et al. Thymic stromal lymphopoietin-elicited basophil responses promote eosinophilic esophagitis. Nat Med. 19(8):1005-1013 (2013).
Nurbhai et al.: Oral Anti-Tumour Necrosis Factor Domain Antibody V565 Provides High Intestinal Concentrations, and Reduces Markers of Inflammation in Ulcerative Colitis Patients. Sci Rep. 9(1):14042 (2019).
Nygren. Alternative binding proteins: affibody binding proteins developed from a small three-helix bundle scaffold. FEBS J. 275(11):2668-2676 (2008).
Ordas et al.: Anti-TNF monoclonal antibodies in inflammatory bowel disease: pharmacokinetics-based dosing paradigms. Clin Pharmacol Ther. 91(4):635-646 (2012).
PCT/EP2016/057024 International Search Report and Written Opinion dated Jun. 16, 2016.
PCT/EP2017/057775 International Search Report and Written Opinion dated Jul. 7, 2017.
PCT/GB2020/051495 International Search Report and Written Opinion dated Sep. 30, 2020.
PCT/GB2020/051496 International Search Report and Written Opinion dated Oct. 20, 2020.
PCT/GB2020/051497 International Search Report and Written Opinion dated Sep. 17, 2020.
PCT/MT2017/000001 International Search Report and Written Opinion dated Oct. 20, 2017.
Peters et al. Innate lymphoid cells in inflammatory bowel diseases. Immunol Lett. 172:124-131 (2015).
Rimoldi et al. Intestinal immune homeostasis is regulated by the crosstalk between epithelial cells and dendritic cells. Nat Immunol. 6(5):507-514 (2005).
Rose et al. Identification and biochemical characterization of human plasma soluble IL-7R: lower concentrations in HIV-1-infected patients. J Immunol. 182(12):7389-7397 (2009).
Saerens et al. Identification of a universal VHH framework to graft non-canonical antigen-binding loops of camel single-domain antibodies. J Mol Biol. 352(3):597-607 (2005).
Sandborn et al. Certolizumab pegol for the treatment of Crohn's disease. N Engl J Med. 357:228-238 (2007).
Schreiber et al. Maintenance therapy with certolizumab pegol for Crohn's disease. N Engl J Med. 357:239-250 (2007).
Silverman et al., Multivalent avimer proteins evolved by exon shuffling of a family of human receptor domains. Nat. Biotechnol. 23 (12):1556-1561 (2005).
Skerra: Alternative binding proteins: anticalins—harnessing the structural plasticity of the lipocalin ligand pocket to engineer novel binding activities. FEBS J. 275(11):2677-2683 (2008).
Suderman et al.: Development of polyol-responsive antibody mimetics for single-step protein purification. Protein Expr Purif. 134:114-124 (2017).
Tal et al.: Interleukin 7 and thymic stromal lymphopoietin: from immunity to leukemia. Cell Mol Life Sci. 71(3):365-378 (2014).
Teng et al. IL-12 and IL-23 cytokines: from discovery to targeted therapies for immune-mediated inflammatory diseases. Nat Med. 21:719-729 (2015).
Teutsch et al. Identification of 11 novel and common single nucleotide polymorphisms in the interleukin-7 receptor-alpha gene and their associations with multiple sclerosis. Eur J Hum Genet. 11(7):509-515 (2003).
Tsilingiri et al. Thymic Stromal Lymphopoietin: To Cut a Long Story Short. Cell Mol Gastroenterol Hepatol. 3(2):174-182 (2017).
Ungar et al.: Optimizing Anti-TNF-a Therapy: Serum Levels of Infliximab and Adalimumab Are Associated With Mucosal Healing in Patients With Inflammatory Bowel Diseases. Clin Gastroenterol Hepatol. 14(4):550-557 (2016).
U.S. Appl. No. 15/273,353 Office Action dated Aug. 16, 2018.
U.S. Appl. No. 15/273,353 Office Action dated Jan. 23, 2018.
U.S. Appl. No. 15/273,353 Office Action dated Jun. 4, 2019.
U.S. Appl. No. 15/717,230 Office Action dated Jan. 21, 2020.
U.S. Appl. No. 15/717,230 Office Action dated May 18, 2020.
U.S. Appl. No. 15/717,230 Office Action dated Sep. 3, 2019.
U.S. Appl. No. 16/140,843 Office Action dated Nov. 26, 2019.
U.S. Appl. No. 16/988,506 Office Action dated Oct. 6, 2020.
Van Schie et al.: The antibody response against human and chimeric anti-TNF therapeutic antibodies primarily targets the TNF binding region. Ann Rheum Dis. 74(1):311-314 (2015).
Verstraete et al. Structure and antagonism of the receptor complex mediated by human TSLP in allergy and asthma. Nat Commun. 8:14937 (2017).
Vetter et al. Emerging oral targeted therapies in inflammatory bowel diseases: opportunities and challenges. Therap Adv Gastroenterol. 10(10):773-790 (2017).
Vincke et al. General strategy to humanize a camelid single-domain antibody and identification of a universal humanized nanobody scaffold. J. Biol. Chem. 284(5):3273-3284 (2009).
Vossenkamper et al.: A CD3-specific antibody reduces cytokine production and alters phosphoprotein profiles in intestinal tissues from patients with inflammatory bowel disease. Gastroenterology 147(1):172-183 (2014).
Walsh. Structural insights into the common γ-chain family of cytokines and receptors from the interleukin-7 pathway. Immunol Rev. 250(1):303-316 (2012).
Winkler et al. Changing the antigen binding specificity by single point mutations of an anti-p24 (HIV-1) antibody. J Immunol. 165(8):4505-4514 (2000).
Burkovitz et al. Large-scale analysis of somatic hypermutations in antibodies reveals which structural regions, positions and amino acids are modified to improve affinity. FEBS 281(1):306-319 (2014).
Clark et al. Trends in antibody sequence changes during the somatic hypermutation process. J Immunol 177(1):333-340 (2006).
Julian et al. Efficient affinity maturation of antibody variable domains requires co-selection of compensatory mutations to maintain thermodynamic stability. Sci Rep 7:45259 (2017).
Lu et al. Immune Modulation by Human Secreted RNases at the Extracellular Space. Front Immunol 9:1012 (2018).
Murphy et al. Enhancing recombinant antibody performance by optimally engineering its format. J Immunol Methods 463:127-133 (2018).
Murtaugh et al. A combinatorial histidine scanning library approach to engineer highly pH-dependent protein switches. Protein Sci 20(9):1619-1631 (2011).
U.S. Appl. No. 16/950,758 Office Action dated Oct. 23, 2023.
U.S. Appl. No. 17/698,823 Office Action dated Nov. 7, 2023.
Wallace et al. Immunopathology of inflammatory bowel disease. World J Gastroenterol 20(1):6-21 (2014).
Gustot et al. Profile of soluble cytokine receptors in Crohn's disease. Gut. 54(4):488-495 (2005).
Hosokawa et al. Interleukin-6 and soluble interleukin-6 receptor in the colonic mucosa of inflammatory bowel disease. Journal of Gastroenterology and Hepatology 14(10):987-996 (1999).
Ito et al. A pilot randomized trial of a human anti-interleukin-6 receptor monoclonal antibody in active Crohn's disease. Gastroenterology 126(4):989-996 (2004).
Katoh et al. MAFFT multiple sequence alignment software version 7: improvements in performance and usability. Mol Biol Evol. 30(4):772-780 (2013).

(56) References Cited

OTHER PUBLICATIONS

Koh et al. Generation of a family-specific phage library of llama single chain antibody fragments that neutralize HIV-1. Journal of Biological Chemistry 285(25):19116-19124 (2010).

Kusugami et al. Elevation of interleukin-6 in inflammatory bowel disease is macrophage- and epithelial cell-dependent. Dig Dis Sci. 40(5):949-959 (1995).

Merchlinsky et al. Construction of an infectious molecular clone of the autonomous parvovirus minute virus of mice. Journal of Virology 47(1):227-232 (1983).

Mitsuyama et al. Therapeutic strategies for targeting the IL-6/STAT3 cytokine signaling pathway in inflammatory bowel disease. Anticancer Research 27(6A):3749-3756 (2007).

Nelson et al. Monoclonal antibodies. Mol Pathol. 53(3):111-117 (2000).

Reimund et al. Increased production of tumour necrosis factor-alpha interleukin-1 beta, and interleukin-6 by morphologically normal intestinal biopsies from patients with Crohn's disease. Gut 39(5):684-689 (1996).

Reimund et al. Mucosal inflammatory cytokine production by intestinal biopsies in patients with ulcerative colitis and Crohn's disease. Journal of Clinical Immunology 16(3):144-150 (1996).

Reinecker et al., Enhanced secretion of tumor necrosis factor-alpha, IL-6 and IL-1 beta by isolated lamina propia mononuclear cells from patients with ulcerative colitis and Crohn's disease Clin Exp Immunol 94:174-181 (1993).

U.S. Appl. No. 16/950,758 Office Action dated Feb. 29, 2024.

U.S. Appl. No. 17/620,030 Ex Parte Quayle Action dated Aug. 2, 2024.

Waetzig et al. Hitting a complex target: an update on interleukin-6 trans-signalling. Expert Opin Ther Targets. 16(2):225-236 (2012).

\* cited by examiner

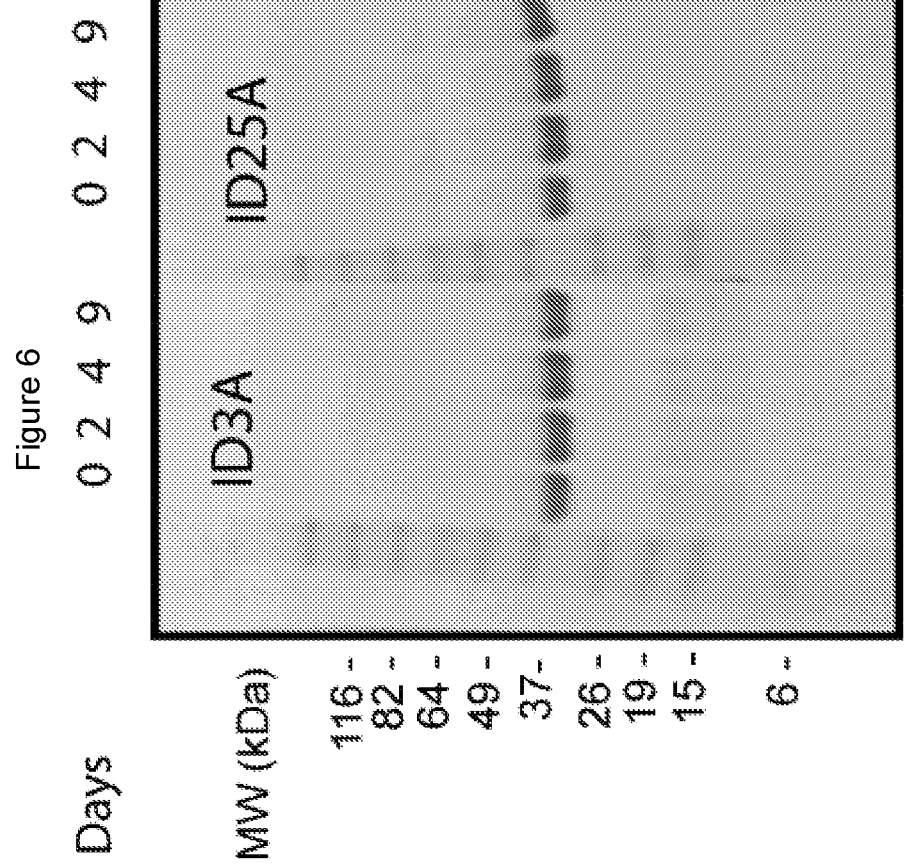

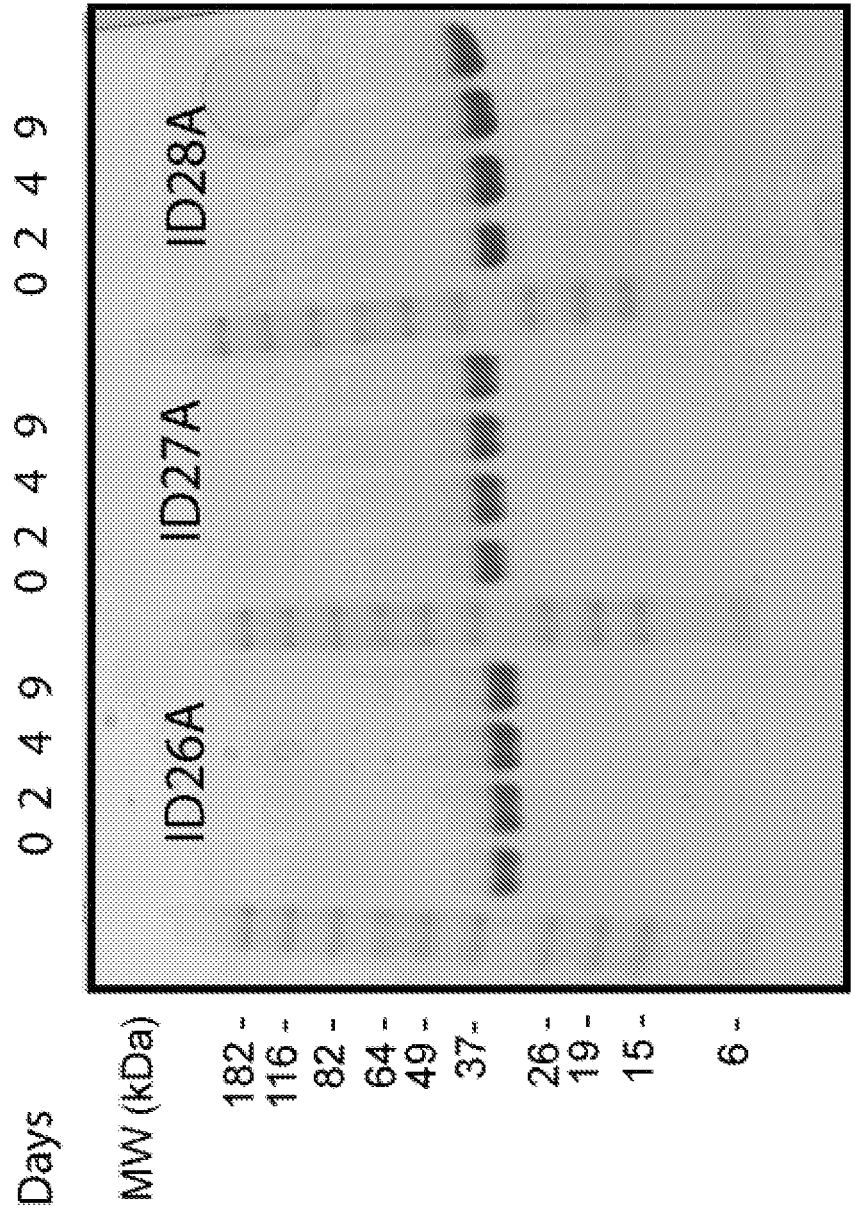

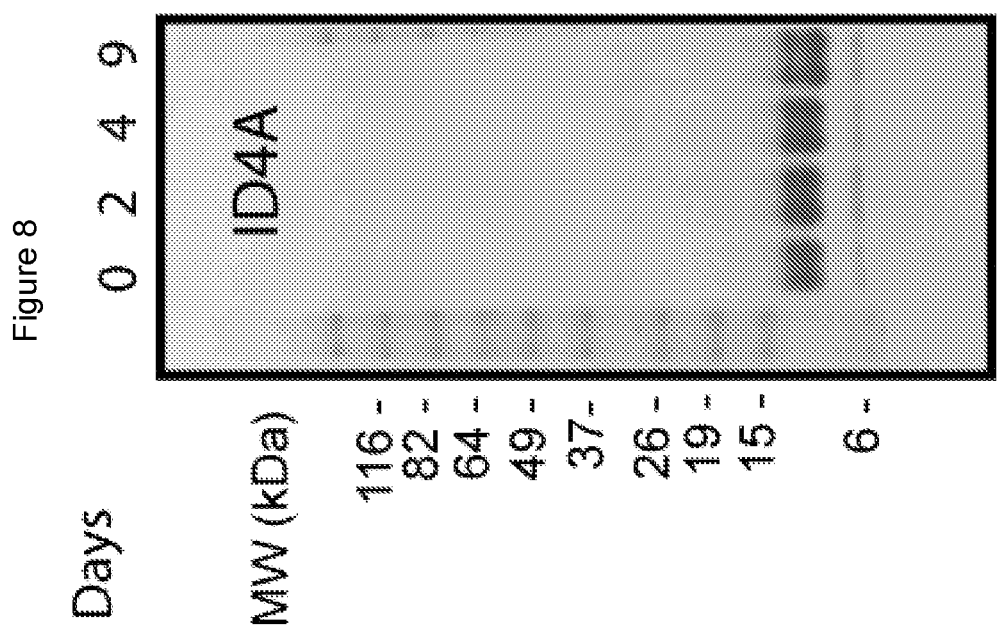

PEPTIDE CONSTRUCT HAVING A PROTEASE-CLEAVABLE LINKER

CROSS-REFERENCE TO RELATED APPLICATIONS

The present application is a continuation application of Ser. No. 15/717,174, filed Sep. 27, 2017, now abandoned, which is a continuation application of PCT/EP2016/057022 filed Mar. 31, 2016 which claims priority from EP 15162114.1 filed Mar. 31, 2015, EP 15162115.8 filed Mar. 31, 2015, EP 15162112.5 filed on Mar. 31, 2015 and EP 16152320.4 filed on Jan. 21, 2016, the contents of each of which are incorporated herein by reference in their entirety.

FIELD OF THE INVENTION

The present invention relates to constructs suitable for oral administration comprising polypeptides connected by a labile peptide linker as well as to pharmaceutical compositions comprising such constructs. The present invention also relates to methods for preparing such constructs, methods which assay the lability of such constructs, methods which utilise such constructs, nucleic acids encoding such constructs, cDNA and vectors comprising nucleic acids encoding such constructs, host cells expressing or capable of expressing such constructs and to uses of such constructs or pharmaceutical compositions.

BACKGROUND OF THE INVENTION

Constructs comprising two or more polypeptides are a class of biomolecules with multi-functional properties. By genetically fusing two or more polypeptides together, the resultant construct may obtain many distinct functions derived from each component polypeptide. Such constructs have been utilised in biological research for many purposes such as protein purification and imaging. Such constructs have also become an important category of biopharmaceuticals. An effective construct requires a suitable linker. Direct fusion of polypeptides without a linker may lead to many undesirable outcomes including misfolding of the fused polypeptides, low yield in polypeptide production or impaired bioactivity. Therefore, the selection or rational design of a linker to join polypeptides is an important area in recombinant polypeptide technology.

Many constructs incorporate linkers which are relatively stable for the purposes of in vivo delivery or recombinant production. Stable linkers covalently join functional domains together to act as one molecule throughout the in vivo or recombinant production processes. A stable linkage between polypeptides may provide many advantages such as a prolonged plasma half-life and resistance to cleavage by host organism proteases. However, stable linkers also have several potential drawbacks including steric hindrance between polypeptides, decreased bioactivity, and altered biodistribution (Chen et al. 2013 *Adv Drug Deliv Rev.* 65(10):1357-1369). It would be advantageous therefore to release free polypeptides from a construct in vivo and thereby potentially reduce steric hindrance, improve bioactivity or achieve independent functions of individual polypeptides.

In the context of polypeptides having effects in the intestinal tract, such release would ideally take place in the intestinal tract after oral administration. It may be preferable that such release takes place only in one or a number of specific locations within the intestinal tract.

Constructs of the present invention may, in at least some embodiments, have one or more of the following advantages compared to substances of the prior art:

(i) increased suitability for oral administration;
(ii) increased suitability for local delivery to the intestinal tract following oral administration;
(iii) ability to target (i.e. cleave the construct into component polypeptides) at one or more specific regions of the intestinal tract;
(iv) increased convenience in incorporating two or more separable polypeptides in one recombinant product;
(v) improved treatment and/or prevention of gastrointestinal tract infection or autoimmune and/or inflammatory diseases;
(vi) increased suitability for expression, in a heterologous host such as bacteria (e.g. *Escherichia coli*) and/or mammalian cells and/or a yeast or mould (e.g. those belonging to the genera *Aspergillus, Saccharomyces, Kluyveromyces, Hansenula* or *Pichia*, such as *Saccharomyces cerevisiae* or *Pichia pastoris*);
(vii) increased stability to protease degradation during production (for example resistance to yeast, mould or mammalian cell proteases);
(viii) improved folding of polypeptides;
(ix) improved yield during recombinant production;
(x) improved bioactivity and/or biodistribution;
(xi) suitability for, and improved properties for, use in a pharmaceutical;
(xii) suitability for, and improved properties for, use in a functional food.

SUMMARY OF THE INVENTION

The present inventors have produced surprisingly advantageous constructs suitable for oral administration comprising a first polypeptide and a second polypeptide connected by a labile peptide linker. These constructs are particularly advantageous due to their convenience of production and their ability to release free component polypeptides within the intestinal tract. In one embodiment, the free component polypeptides may be released in one or more specific regions of the intestinal tract.

It may be expected that these constructs have particular utility in the prevention or treatment of diseases of the GIT such as autoimmune and/or inflammatory disease such as inflammatory bowel disease, or in the prevention or treatment of infection from an intestinal tract resident pathogenic microbe.

The present invention provides a construct suitable for oral administration comprising a first polypeptide and a second polypeptide connected by a labile peptide linker, wherein the labile peptide linker is labile to one or more proteases present in the intestinal tract and wherein the first and second polypeptides are substantially resistant to said one or more proteases. Also provided are related compositions, methods and nucleic acids relating to the inventive construct.

DESCRIPTION OF THE SEQUENCES

Figure 1:
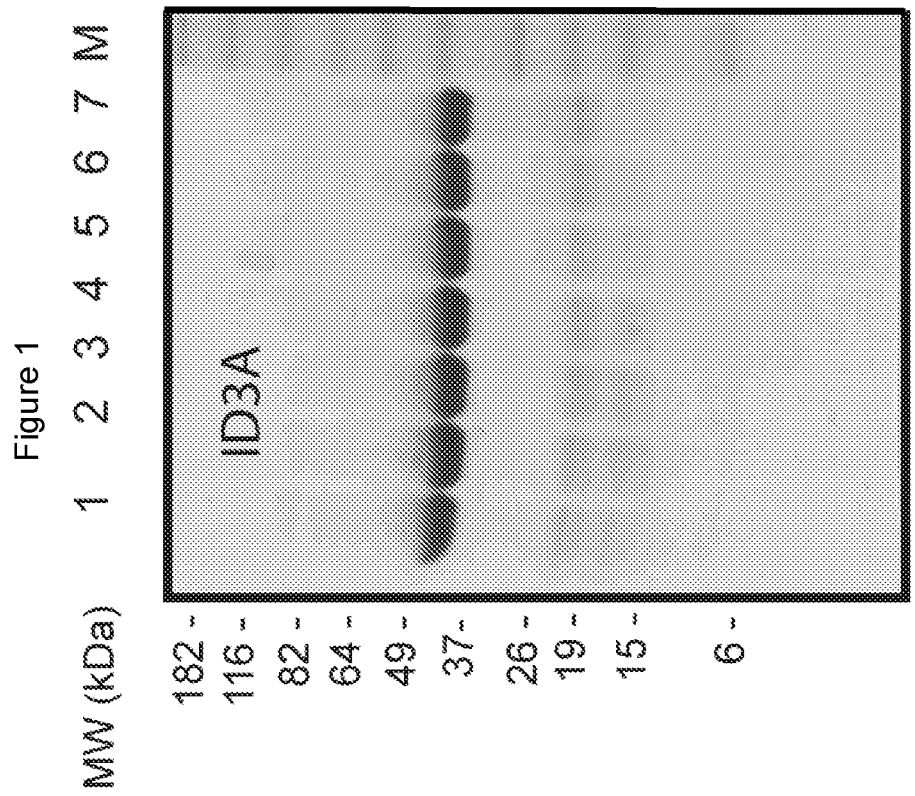
FIG. 1—Stained PAGE gel demonstrating non-lability of ID3A using the Trypsin Protease Assay FIG. 2—Stained PAGE gel demonstrating lability of ID25A and ID26A using the Trypsin Protease Assay FIG. 3—Stained PAGE gel demonstrating lability of ID27A and ID28A using the Trypsin Protease Assay FIG. 4—Stained PAGE gel demonstrating lability of ID3A, ID25A, ID26A, ID27A and ID28A using the Faecal Protease Assay FIG. 5—Stained PAGE gel demonstrating lability of ID55F, ID56F, ID57F, ID58F, ID59F and ID60F using the Faecal Protease Assay FIG. 6—Stained PAGE gels demonstrating storage stability of ID3A and ID25A FIG. 7—Stained PAGE gel demonstrating storage stability of ID26A, ID27A and ID28A FIG. 8—Stained PAGE gel demonstrating storage stability of ID4A

SEQ ID NO: 1—Polypeptide sequence of linker used in constructs ID3A and ID55F
SEQ ID NO: 2—Polypeptide sequence of linker used in constructs ID25A and ID57F
SEQ ID NO: 3—Polypeptide sequence of linker used in constructs ID26A and ID58F
SEQ ID NO: 4—Polypeptide sequence of linker used in constructs ID27A and ID59F
SEQ ID NO: 5—Polypeptide sequence of linker used in constructs ID28A and ID60F
SEQ ID NO: 6—Polypeptide sequence of linker used in construct ID56F
SEQ ID NO: 7—Polypeptide sequence of ID3A construct
SEQ ID NO: 8—Polypeptide sequence of ID25A construct
SEQ ID NO: 9—Polypeptide sequence of ID26A construct
SEQ ID NO: 10—Polypeptide sequence of ID27A construct
SEQ ID NO: 11—Polypeptide sequence of ID28A construct
SEQ ID NO: 12—Polypeptide sequence of ID55F construct
SEQ ID NO: 13—Polypeptide sequence of ID57F construct
SEQ ID NO: 14—Polypeptide sequence of ID58F construct
SEQ ID NO: 15—Polypeptide sequence of ID59F construct
SEQ ID NO: 16—Polypeptide sequence of ID60F construct
SEQ ID NO: 17—Polypeptide sequence of ID56F construct
SEQ ID NO: 18—Polypeptide sequence of ID1A ICVD
SEQ ID NO: 19—Polypeptide sequence of ID5F ICVD
SEQ ID NO: 20—Polynucleotide sequence encoding ID3A construct
SEQ ID NO: 21—Polynucleotide sequence encoding ID25A construct
SEQ ID NO: 22—Polynucleotide sequence encoding ID26A construct
SEQ ID NO: 23—Polynucleotide sequence encoding ID27A construct
SEQ ID NO: 24—Polynucleotide sequence encoding ID28A construct
SEQ ID NO: 25—Polynucleotide sequence encoding ID55F construct
SEQ ID NO: 26—Polynucleotide sequence encoding ID57F construct
SEQ ID NO: 27—Polynucleotide sequence encoding ID58F construct
SEQ ID NO: 28—Polynucleotide sequence encoding ID59F construct
SEQ ID NO: 29—Polynucleotide sequence encoding ID60F construct
SEQ ID NO: 30—Polynucleotide sequence encoding ID56F construct
SEQ ID NO: 31—An exemplary polynucleotide sequence which would encode linker used in constructs ID3A and ID55F
SEQ ID NO: 32—An exemplary polynucleotide sequence which would encode linker used in constructs ID25A and ID57F
SEQ ID NO: 33—An exemplary polynucleotide sequence which would encode linker used in constructs ID26A and ID58F
SEQ ID NO: 34—An exemplary polynucleotide sequence which would encode linker used in constructs ID27A and ID59F
SEQ ID NO: 35—An exemplary polynucleotide sequence which would encode linker used in constructs ID28A and ID60F
SEQ ID NO: 36—An exemplary polynucleotide sequence which would encode linker used in construct ID56F
SEQ ID NO: 37—Proposed chymotrypsin-labile linker
SEQ ID NO: 38—Polypeptide sequence of ID4A construct

DETAILED DESCRIPTION OF THE INVENTION

Labile Peptide Linkers

The construct of the invention comprises a labile peptide linker, which connects the first and second polypeptides. In one embodiment of the invention, the labile peptide linker can be engineered such that it resists cleavage by proteases to a desired extent and/or is only cleaved upon exposure to a specific area of the intestinal tract. For example, if a construct is recombinantly produced in a host such as yeast, trypsin-like proteases produced by the yeast may cleave the recombinant construct product. This may result in difficulties in purification and cause regulatory, clinical and commercial complications. Similarly, if for example the first polypeptide is a toxin, the second polypeptide of the construct may act to 'quench' the effects of the toxin until it is released at a suitable, target location.

This can be achieved according to one embodiment of the invention by incorporating shielding residues into the labile peptide linker flanking the labile site(s). Shielding residues flank the labile site(s) of the labile peptide linker and reduce the lability thereof. Cleavage resistance can also be increased by positioning the labile site(s) closer to or at the periphery of the labile peptide linker. This concept is referred to as a "shielded labile site" and provides controlled lability.

In a further embodiment of the invention, the labile peptide linker can be engineered such that it is highly labile to cleavage by intestinal tract proteases, thereby quickly releasing the constituent first and second polypeptides of the construct after oral administration. This is achieved by incorporating one or more labile sites into the labile peptide linker such that the labile site is exposed for proteolysis, for example by positioning the labile site(s) substantially centrally in the labile peptide linker and/or by the labile site not being shielded substantially by flanking residues. This concept is referred to as a "non-shielded labile site".

Suitably the labile peptide linker has a length of at least 3, such as at least 4, such as at least 5, such as at least 6, such as at least 7, such as at least 8, such as at least 9, such as at least 10 residues. Suitably the labile peptide linker has a length of no greater than 40, such as no greater than 35, such as no greater than 30, such as no greater than 25, such as no greater than 20, such as no greater than 15 residues.

Incorporation of a P residue into the labile peptide linker of the construct of the invention is expected to substantially prevent cleavage of the labile peptide linker. Suitably the labile peptide linker does not comprise any P residues.

Trypsin Labile Sites

Shielded Trypsin Labile Sites

Suitably the labile peptide linker of the construct of the invention comprises a cleavage site for trypsin or a trypsin-like protease. Suitably the labile peptide linker comprises at least 1, such as at least 2, such as at least 3, such as at least 4, such as at least 5, such as at least 6, such as at least 7, such as at least 8, such as at least 9, such as at least 10 K residues. Suitably the labile peptide linker comprises at least 1, such as at least 2, such as at least 3, such as at least 4, such as at least 5, such as at least 6, such as at least 7, such as at least 8, such as at least 9, such as at least 10 R residues. Preferably the cleavage site(s) is/are one or more K residue(s).

Shielding residues in the case of a trypsin or trypsin-like protease labile site may be D or E. Suitably the labile peptide linker comprises one or more shielding residues selected from the list consisting of D or E.

Suitably all K or R residues comprised within the labile peptide linker have at least 1, such as at least 2, such as at least 3, such as at least 4, such as at least 5 shielding residues on their N-terminal side, wherein the shielding residues are selected from the list consisting of: D and E. Suitably all K or R residues comprised within the labile peptide linker have 1 to 5, 1 to 4, 1 to 3, 1 to 2, 2 to 5, 2 to 4, 2 to 3, 3 to 5, 3 to 4, 4 to 5 shielding residues on their N-terminal side, wherein the shielding residues are selected from the list consisting of: D and E.

Suitably all K or R residues comprised within the labile peptide linker have and at least 1, such as at least 2, such as at least 3, such as at least 4, such as at least 5 shielding residues on their C-terminal side, wherein the shielding residues are selected from the list consisting of: D and E. Suitably all K or R residues comprised within the labile peptide linker have 1 to 5, 1 to 4, 1 to 3, 1 to 2, 2 to 5, 2 to 4, 2 to 3, 3 to 5, 3 to 4, 4 to 5 shielding residues on their C-terminal side, wherein the shielding residues are selected from the list consisting of: D and E.

Suitably all K and R residues have at least one shielding residue adjacent to them, suitably followed by one or more further contiguous shielding residues. Suitably the shielding residues occur on one or both sides of one or more of the K or R residues.

Suitably the labile peptide linker comprises or more suitably consists of a polypeptide sequence of the format:

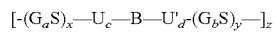

wherein
a is 1 to 10;
b is 1 to 10;
U is D or E;
U' is D or E;
c is 0 to 7;
d is 0 to 7;
x is 1 to 10;
y is 1 to 10
z is 1 to 10 and
B is K or R.

Suitably a is 2 to 5, more suitably a is 4. Suitably b is 2 to 5, more suitably b is 4. Suitably x is 1 to 5, more suitably x is 1. Suitably y is 1 to 5, more suitably y is 1. Suitably z is 1 to 3, more suitably z is 1. Suitably, B is K. Suitably, U if present, is D. Suitably, U' if present, is D. In one embodiment c is 1 and d is 1. In another embodiment c is 0 and d is 0. In a further embodiment c is 4 and d is 0. Suitably both U and U' are each individually D and c and d are both 1.

Suitably the labile peptide linker comprises or more suitably consists of a polypeptide sequence of the format:

wherein
a is 1 to 10;
x is 1 to 10;
B is K or R and
B' is K or R.

In one embodiment, a is 2 to 5, more suitably a is 4. In a further embodiment x is 1 to 5. More suitably, x is 2. Suitably, B is K. Suitably, B' is K.

Suitably the labile peptide linker comprises or more suitably consists of a polypeptide sequence of the format:

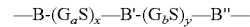

wherein
a is 1 to 10;
b is 1 to 10;
x is 1 to 10;
y is 1 to 10;
B is K or R
B' is K or R and
B" is K or R.

In one embodiment, a is 2 to 5, more suitably a is 4. In one embodiment, b is 2 to 5, more suitably b is 4. In a further embodiment x is 1 to 5. More suitably, x is 2. In a further embodiment y is 1 to 5. More suitably, y is 2. Suitably, B is K. Suitably, B' is K. Suitably, B" is K.

Non-Shielded Trypsin Labile Sites

Suitably the labile peptide linker of the construct of the invention comprises a cleavage site for trypsin or a trypsin-like protease. Suitably the labile peptide linker comprises at least 1, such as at least 2, such as at least 3, such as at least 4, such as at least 5, such as at least 6, such as at least 7, such as at least 8, such as at least 9, such as at least 10 K residues. Suitably the labile peptide linker comprises at least 1, such as at least 2, such as at least 3, such as at least 4, such as at least 5, such as at least 6, such as at least 7, such as at least 8, such as at least 9, such as at least 10 R residues. Preferably the cleavage site(s) is/are one or more K residue(s).

Suitably all K or R residues comprised within the labile peptide linker have at least 1, such as at least 2, such as at least 3, such as at least 4, such as at least 5 non-shielding residues on their N-terminal side wherein the non-shielding residues are selected from the list consisting of: C, A, S, N, G, L, I, V, T, M, F, Y, H, W and Q; more suitably A, G, L, I, V, M, S and T; more suitably A, G, L, I, V and S; more suitably G and S. Suitably all K or R residues comprised within the labile peptide linker have 1 to 5, 1 to 4, 1 to 3, 1 to 2, 2 to 5, 2 to 4, 2 to 3, 3 to 5, 3 to 4, 4 to 5 non-shielding residues on their N-terminal side, wherein the shielding residues are selected from the list consisting of: C, A, S, N, G, L, I, V, T, M, F, Y, H, W and Q; more suitably A, G, L, I, V, M, S and T; more suitably A, G, L, I, V and S; more suitably G and S.

Suitably all K or R residues comprised within the labile peptide linker have at least 1, such as at least 2, such as at least 3, such as at least 4, such as at least 5 non-shielding residues on their C-terminal side, wherein the non-shielding residues are selected from the list consisting of: C, A, S, N, G, L, I, V, T, M, F, Y, H, W and Q; more suitably A, G, L, I, V, M, S and T; more suitably A, G, L, I, V and S; more suitably G and S. Suitably all K or R residues comprised within the labile peptide linker have 1 to 5, 1 to 4, 1 to 3, 1 to 2, 2 to 5, 2 to 4, 2 to 3, 3 to 5, 3 to 4, 4 to 5 non-shielding residues on their C-terminal side, wherein the shielding residues are selected from the list consisting of: C, A, S, N, G, L, I, V, T, M, F, Y, H, W and Q; more suitably A, G, L, I, V, M, S and T; more suitably A, G, L, I, V and S; more suitably G and S.

Suitably all K and R residues have at least one non-shielding residue adjacent to them, suitably followed by one or more further contiguous non-shielding residues. Suitably the non-shielding residues occur on one or both sides of one or more of the K or R residues.

Suitably the labile peptide linker does not comprise any D or E residues. Suitably the labile peptide linker consists of residues selected from the list consisting of C, A, S, N, G, L, I, V, T, M, F, Y, H, K, R, W and Q; more suitably A, G, L, I, V, M, S, T, K and R residues; more suitably S, G, K and R residues.

Suitably the labile peptide linker comprises or more suitably consists of a polypeptide sequence of the format:

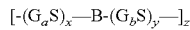

wherein
a is 1 to 10;
b is 1 to 10;
x is 1 to 10;
y is 1 to 10
z is 1 to 10 and
B is K or R.

Suitably a is 2 to 5, more suitably a is 4. Suitably b is 2 to 5, more suitably b is 4. Suitably x is 1 to 5, more suitably x is 1. Suitably y is 1 to 5, more suitably y is 1. Suitably z is 1 to 3, more suitably z is 1. Suitably B is K.

Suitably the labile peptide linker comprises or more suitably consists of a polypeptide sequence of the format:

$[-(G_4S)_x\text{—}B\text{-}(G_4S)_y\text{—}]_z$ wherein
x is 1 to 10;
y is 1 to 10
z is 1 to 10 and
B is K or R.

Suitably x is 1 to 5, more suitably x is 1. Suitably y is 1 to 5, more suitably y is 1. Suitably z is 1 to 3, more suitably, z is 1. Suitably B is K.

Chymotrypsin Labile Sites
Non-Shielded Chymotrypsin Labile Sites

Alternatively, or in addition to trypsin labile sites, the labile peptide linker of the construct of the invention comprises a cleavage site for chymotrypsin or a chymotrypsin-like protease. Suitably the labile peptide linker comprises at least 1, such as at least 2, such as at least 3, such as at least 4, such as at least 5, such as at least 6, such as at least 7, such as at least 8, such as at least 9, such as at least 10 residues selected from the list consisting of W, F, Y, L and M; more suitably W, F and Y. Suitably the labile peptide linker consists of residues selected from the list consisting of S, G, W, F, Y, L and M; such as S, G, W, F and Y.

Suitably the labile peptide linker comprises or more suitably consists of a polypeptide sequence of the format:

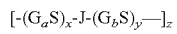

wherein
a is 1 to 10;
b is 1 to 10;
x is 1 to 10;
y is 1 to 10
z is 1 to 10 and
J is W, F, Y, L or M; such as W, F or Y.

In one embodiment a is 2 to 5, in a further embodiment, b is 2 to 5, in a further embodiment x is 1 to 5, in a further embodiment, y is 1 to 5, in a further embodiment z is 1 to 3. Suitably x is 1, y is 1 and z is 1.

Suitably the labile peptide linker comprises or more suitably consists of a polypeptide sequence of the format:

$[-(G_4S)_x\text{-}J\text{-}(G_4S)_y\text{—}]_z$ wherein
x is 1 to 10;
y is 1 to 10
z is 1 to 10 and
J is W, F, Y, L or M; such as W, F or Y.

In one embodiment, x is 1 to 5, in a further embodiment, y is 1 to 5, in a further embodiment z is 1 to 3. Suitably x is 1, y is 1 and z is 1.

MMP Labile Sites

In one embodiment, the labile peptide linker of the construct of the invention comprises a cleavage site for MMP3, MMP10 or MMP12.

Lability

The lability of a construct, and therefore the utility of a construct as a controlled-lability or highly labile construct can be assayed using the Faecal Protease Assay, the Trypsin Protease Assay and/or the Chymotrypsin Protease Assay defined in Examples 1 to 3.

Suitably at least 20%, such as at least 40%, such as at least 60%, such as at least 80%, such as at least 90%, such as at least 100% by mass of the construct remains uncleaved after at least 10, such as at least 20, such as at least 30, such as at least 40, such as at least 50, such as at least 60, such as at least 70, such as at least 80, such as at least 90, such as at least 100, such as at least 110, such as at least 120, such as at least 130, such as at least 140, such as at least 150, such as at least 160 minutes after mixing in the Faecal Protease Assay and/or Trypsin Protease Assay and/or Chymotrypsin Protease Assay.

Alternatively, at least 60%, such as at least 80%, such as at least 90%, such as at least 100% of the construct is cleaved after no more than 5, such as no more than 4, such as no more than 3, such as no more than 2, such as no more than 1 minute, after mixing in the Faecal Protease Assay and/or Trypsin Protease Assay and/or Chymotrypsin Protease Assay.

In one aspect of the invention there is provided a method of assaying the lability of a construct of the invention, comprising the steps of: (a) incubating the construct in a solution comprising trypsin, a solution comprising chymotrypsin, faecal supernatant, small intestinal fluid or a solution comprising enteropeptidase (such as by performing the Trypsin Protease Assay, the Chymotrypsin Protease Assay or the Faecal Protease Assay) then (b) ascertaining the proportion of cleaved construct after one or more periods of incubation.

In a further aspect of the invention there is provided a method of delivering a monomeric antibody or a monomeric antigen binding fragment thereof to a targeted region of the intestinal tract, comprising the steps of: (a) performing the method of assaying construct lability described above, (b) selecting a construct with an appropriate level of lability for

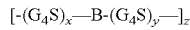

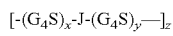

the targeted region of the intestinal tract, (c) producing the selected construct with an enterically coated packaging then (d) administering the packaged selected construct to a subject.

In a further aspect of the invention there is provided a method of preparing a product comprising a construct of the invention which has been selected, the method comprising adding the selected construct into the product, wherein the selected construct is selected and produced by a method comprising the steps of: (a) performing the method of assaying construct lability described above then (b) selecting a construct with an appropriate level of lability for the targeted region of the intestinal tract.

Stability

Various organisms may be used to express recombinant polypeptides. Commonly used expression organisms include yeast, mould and mammalian cells. However, many of these expression organisms also produce proteases, such as trypsin-like proteases, which may cleave the expressed recombinant polypeptide. If the expressed polypeptide incorporates a peptide linker which is labile to one or more proteases present in the intestinal tract, then this peptide linker may undesirably also be labile to proteases produced by the expression organism, thus preventing effective expression of intact polypeptide.

It is advantageous for the labile peptide linker to be substantially non-labile to enzymes produced by the recombinant host used to produce the construct. Suitably the labile peptide linker is substantially resistant to proteases produced by a recombinant host such as bacteria such as *E. coli* or such as a yeast or mould belonging to the genera *Aspergillus, Saccharomyces, Kluyveromyces, Hansenula* or *Pichia*; such as *Saccharomyces cerevisiae* or *Pichia pastoris*. Suitably the recombinant host is a yeast. Suitably the recombinant host is a mould. Suitably the yeast belongs to the genera *Saccharomyces, Kluyveromyces, Hansenula* or *Pichia*. Further examples of yeasts are those belonging to the genera *Candida* and *Torulopsis*. Suitably the mould belongs to the genus *Aspergillus*. Further examples of moulds are those belonging to the genera *Acremonium, Alternaria, Chrysosporium, Cladosporium, Dictyostelium, Fusarium, Mucor, Penicillium, Rhizopus, Stachybotrys, Trichoderma* and *Trichophyton*. Suitably the labile peptide linker is substantially resistant to proteases produced by a recombinant host for at least 2, such as at least 4, such as at least 9, such as at least 14, such as at least 60 days' storage at 4 degrees C.

Yeast-Produced Constructs for Oral Administration

In one aspect of the invention there is provided a construct for use in the treatment by oral administration of a disease of the intestinal tract with a first immunoglobulin chain variable domain and a second immunoglobulin chain variable domain, wherein the construct comprises the first immunoglobulin chain variable domain and the second immunoglobulin chain variable domain connected by a labile peptide linker, wherein:
  (i) the labile peptide linker is labile to one or more proteases present in the intestinal tract,
  (ii) the labile peptide linker is stable to yeast proteases and
  (iii) the first and second immunoglobulin chain variable domains are substantially resistant to said one or more proteases and
wherein the construct is produced in yeast.

In a further aspect of the invention there is provided a method of treating by oral administration a disease of the intestinal tract with a first immunoglobulin chain variable domain and a second immunoglobulin chain variable domain from a construct, wherein the construct comprises the first immunoglobulin chain variable domain and the second immunoglobulin chain variable domain connected by a labile peptide linker, wherein:
  (i) the labile peptide linker is labile to one or more proteases present in the intestinal tract,
  (ii) the labile peptide linker is stable to yeast proteases and
  (iii) the first and second immunoglobulin chain variable domains are substantially resistant to said one or more proteases;
wherein the construct is produced in yeast.

In a further aspect of the invention there is provided a method of delivering a first immunoglobulin chain variable domain and a second immunoglobulin chain variable domain to the intestinal tract comprising producing in yeast and then orally administering a construct comprising the first immunoglobulin chain variable domain and the second immunoglobulin chain variable domain connected by a labile peptide linker, wherein:
  (i) the labile peptide linker is labile to one or more proteases present in the intestinal tract,
  (ii) the labile peptide linker is stable to yeast proteases and
  (iii) the first and second immunoglobulin chain variable domains are substantially resistant to said one or more proteases.

In a further aspect of the invention there is provided a method of making a construct comprising a first immunoglobulin chain variable domain and a second immunoglobulin chain variable domain connected by a labile peptide linker, wherein:
  (i) the labile peptide linker is labile to one or more proteases present in the intestinal tract,
  (ii) the labile peptide linker is stable to yeast proteases and
  (iii) the first and second immunoglobulin chain variable domains are substantially resistant to said one or more proteases;
comprising the step of producing the construct in yeast.

Suitably the step of producing the construct in yeast is performed by providing a host yeast cell which is capable of expressing the construct of the invention, transformed with a vector, wherein the vector comprises a polynucleotide encoding the construct of the invention and wherein the host yeast cell is exposed to conditions suitable for expression of the construct of the invention.

Suitably the first immunoglobulin chain variable domain and the second immunoglobulin chain variable domain are substantially resistant to yeast proteases.

Suitably the methods outlined above further comprise the step of purifying the construct. Suitably the labile peptide linker is cleaved in the intestinal tract by the one or more proteases present in the intestinal tract. In a further aspect of the invention, there is provided a construct obtained by any of the above methods.

The constructs for use and methods described above relate to the production of a construct in yeast. However, these constructs for use and methods are also equally applicable to production of a construct in any expression organism which produces proteases which may cleave a peptide linker, such as mammalian cells or moulds (such as moulds from any one or more of the genera *Acremonium, Alternaria, Aspergillus, Chrysosporium, Cladosporium, Dictyostelium, Fusarium, Mucor, Penicillium, Rhizopus, Stachybotrys, Trichoderma* and *Trichophyton*).

Particular characteristics of these embodiments of the invention are further discussed as follows.

1. A Labile Peptide Linker which is Labile to One or More Proteases Present in the Intestinal Tract Examples 5 and 6 below provide details on specific constructs of the invention which comprise labile peptide linkers which are labile to one or more proteases present in the intestinal tract.

Suitably the labile peptide linker is labile to one or more proteases present in the intestinal tract such that greater than 50%, such as greater than 60%, such as greater than 70%, such as greater than 80%, such as greater than 85%, such as greater than 90% by mass of the construct is cleaved into first and second immunoglobulin chain variable domains after 160 minutes, more suitably after 105 minutes, more suitably after 60 minutes, more suitably after 25 minutes, more suitably after 10 minutes after mixing in the Trypsin Protease Assay.

2. A Labile Peptide Linker which is Stable to Yeast Proteases

Example 7 below provides details on specific constructs of the invention which comprise labile peptide linkers which are stable to yeast proteases. Example 9 below provides details on a specific construct (ID4A) which is not stable to yeast proteases.

The stability of a linker to yeast proteases may be assessed using the Yeast Expression Protocol outlined as follows.

The Yeast Expression Protocol:

The following protocol outlines a method for the cloning of polypeptides (such as constructs comprising ICVDs or monomeric ICVDs) into the chromosome of *Saccharomyces cerevisiae* such that induction in a suitable growth medium results in polypeptide expression and secretion into the extracellular supernatant.

An *S. cerevisiae* strain of the following description is used for this process: The production strain used for expression and manufacture of polypeptides is a derivative of the CEN.PK series from the EUROSCARF collection (EUROpean *Saccharomyces Cerevisiae* ARchive for Functional analysis). The genotype of the CEN.PK strain is: MATa/MATa ura3-52/ura3-52; trp1-289/trp1-289; leu2-3, 112/leu2-3, 112; his3Δ 1/his3Δ 1; MAL2-8C/MAL2-8C; SUC2/SUC2. This strain is then further modified to inhibit the ability to grow on galactose by deletion of the galactokinase gene (gal1::URA3). This is the final strain used for transformation by the polypeptide expression constructs.

Monomeric or multimeric DNA constructs, in which polypeptides (such as constructs comprising ICVDs or monomeric ICVDs) joined by protein linkers, are cloned into a suitable multi-copy chromosomal integration vector (Lopes et al. 1991. Gene. 105, 83-90), generating an integration cassette. The integration cassette may include an inducible promoter (for example pGal7, Nogi & Fukasawa (1983). *Nucleic Acids Res.* 11(24):8555-68), the polypeptide encoding region, a signal sequence that encodes secretion into the extracellular supernatant in yeast (Hashimoto et al. 1998. Protein Engineering. 11 (75-77)) fused immediately upstream of the first amino acid in the polypeptide coding region, an auxotrophic selection marker and DNA sequences that contribute to recombination into the chromosome. Transformation of competent yeast cells with linear DNA encoding the integration cassette and subsequent selection on a suitable auxotrophic medium (for example omitting leucine where a leucine biosynthesis gene is the selection marker) results in integration and amplification at the rDNA locus, such that 100-200 copies of the expression construct may be present in the cell. Following the removal of the selective pressure the expression construct remains stably integrated into the chromosome. Alternatively, polypeptide production may be achieved from a multi-copy episomal vector based on the yeast 2 μM plasmid with a similar expression cassette, without the need for chromosomal integration.

To induce polypeptide expression, a colony of the resulting yeast strain is inoculated into 5 mL of yeast soytone broth supplemented with 2% glucose and grown overnight at 30° C. (150-200 rpm). The following day 50 mL of yeast soytone broth containing 2% glucose and 0.5% galactose (for induction) in a 500 mL Erlenmeyer flask is inoculated with the entire 5 mL overnight culture. The resulting induction culture is incubated at 30° C., 200 rpm for 3 days. The culture is then spun down at 4200 rpm for 20 min in a swing rotor centrifuge to remove yeast cells. The supernatant is then filtered through 0.45 μm and 0.2 μm filters in series.

After carrying out the Yeast Expression Protocol, the polypeptide may then optionally undergo a storage period at 4° C. in the yeast supernatant under sterile conditions.

Suitably a construct of the invention is stable to yeast proteases such that no more than 10%, more suitably no more than 5%, more suitably no more than 1% by mass of the construct is cleaved into first and second immunoglobulin chain variable domains after producing the construct using the Yeast Expression Protocol (i.e. with no subsequent storage period) and then optionally storing for 2 days, more suitably 4 days or more suitably 9 days. "0 days storage" as used herein refers to no subsequent storage period.

Yeast-produced polypeptides may be distinct from those produced using alternative expression organisms such as bacteria, in that yeast-produced polypeptides may comprise post translational modifications such as glycosylation.

3. A First and Second Immunoglobulin Chain Variable Domain which are Substantially Resistant to One or More Proteases Present in the Intestinal Tract Examples 5 and 6 below provide details on specific constructs of the invention which comprise first and second immunoglobulin chain variable domains, wherein the first and second immunoglobulin chain variable domains are substantially resistant to one or more proteases present in the intestinal tract.

Suitably the first immunoglobulin chain variable domain and the second immunoglobulin chain variable domain are substantially resistant to one or more proteases present in the intestinal tract such that at least 70%, such as at least 80%, such as at least 90%, such as at least 95%, such as at least 99%, such as about 100% by mass of the first immunoglobulin chain variable domain and at least 70%, such as at least 80%, such as at least 90%, such as at least 95%, such as at least 99%, such as about 100% by mass of the second immunoglobulin chain variable domain remain uncleaved after 10 minutes, more suitably after 25 minutes, more suitably after 60 minutes, more suitably after 105 minutes, more suitably after 160 minutes after mixing in the Trypsin Protease Assay.

4. A First and Second Immunoglobulin Chain Variable Domain which are Substantially Resistant to Yeast Proteases Example 7 below provides details on specific constructs of the invention which comprise immunoglobulin chain variable domains, wherein the immunoglobulin chain variable domains are stable to yeast proteases.

Suitably the first immunoglobulin chain variable domain and the second immunoglobulin chain variable domain are substantially resistant to yeast proteases such that no more than 10%, more suitably no more than 5%, more suitably no more than 1% by mass of the first or second immunoglobulin chain variable domain are cleaved after producing the first or second immunoglobulin chain variable domain using the Yeast Expression Protocol and then optionally storing for 2 days, more suitably 4 days or more suitably 9 days.

Assessment of Stability and Lability Under Points 1-4 Above

Suitably the cleaved mass of the construct and/or the uncleaved mass of the first and second immunoglobulin chain variable domains and/or the cleaved mass of the first and second immunoglobulin chain variable domains are assessed by gel electrophoresis followed by visual inspection of the gel. More suitably, assessment is by quantitative gel electrophoresis. Alternatively, assessment is by gel electrophoresis followed by mass spectrometry.

Bands on a gel corresponding to cleaved construct and uncleaved immunoglobulin chain variable domain may be identified as those bands having approximately half the mass of the construct (i.e. the mass of one constituent immunoglobulin chain variable domain), by comparison with molecular weight marker. Bands on a gel corresponding to cleaved immunoglobulin chain variable domains are identifiable by having a molecular weight lower than that of the whole constituent immunoglobulin chain variable domain, by comparison to molecular weight marker bands.

In one embodiment, the labile peptide linker of the construct of the invention does not comprise a polypeptide disclosed in WO2009/021754. More specifically, in one embodiment the labile peptide linker of the construct of the invention does not comprise the sequence GGGGSDDDDKGGGGS (SEQ ID NO: 4).

Polypeptides, Antigen-Binding Polypeptides, Antibodies and Antibody Fragments Including Immunoglobulin Chain Variable Domains (ICVD) Such as the VH and VHH Polypeptides are organic polymers consisting of a number of amino acid residues bonded together in a chain. As used herein, 'polypeptide' is used interchangeably with 'protein' and 'peptide'. Polypeptides are said to be antigen-binding when they contain one or more stretches of amino acid residues which form an antigen-binding site, capable of binding to an epitope on a target antigen with an affinity (suitably expressed as a Kd value, a Ka value, a $k_{on}$-rate and/or a $k_{off}$-rate, as further described herein). Antigen-binding polypeptides include polypeptides such as antibodies, antibody fragments and antigen-binding fragments. A polypeptide may comprise a region which is capable of binding a target with high affinity (suitably expressed as a Kd value, a Ka value, a $k_{on}$-rate and/or a $k_{off}$-rate, as further described herein). Such polypeptides include DARPins (Binz et al. Journal of Molecular Biology 332(2):489-503), Affimers™, Fynomers™, Centyrins, Nanofitins® and cyclic peptides.

A conventional antibody or immunoglobulin (Ig) is a protein comprising four polypeptide chains: two heavy (H) chains and two light (L) chains. Each chain is divided into a constant region and a variable domain. The heavy chain variable domains are abbreviated herein as VHC, and the light (L) chain variable domains are abbreviated herein as VLC. These domains, domains related thereto and domains derived therefrom, are referred to herein as immunoglobulin chain variable domains. The VHC and VLC domains can be further subdivided into regions of hypervariability, termed "complementarity determining regions" ("CDRs"), interspersed with regions that are more conserved, termed "framework regions" ("FRs"). The framework and complementarity determining regions have been precisely defined (Kabat et al 1991 Sequences of Proteins of Immunological Interest, Fifth Edition U.S. Department of Health and Human Services, NIH Publication Number 91-3242, herein incorporated by reference in its entirety). In a conventional antibody, each VHC and VLC is composed of three CDRs and four FRs, arranged from amino-terminus to carboxyterminus in the following order: FR1, CDR1, FR2, CDR2, FR3, CDR3, FR4. The conventional antibody tetramer of two heavy immunoglobulin chains and two light immunoglobulin chains is formed with the heavy and the light immunoglobulin chains inter-connected by e.g. disulfide bonds, and the heavy chains similarity connected. The heavy chain constant region includes three domains, CH1, CH2 and CH3. The light chain constant region is comprised of one domain, CL. The variable domain of the heavy chains and the variable domain of the light chains are binding domains that interact with an antigen. The constant regions of the antibodies typically mediate the binding of the antibody to host tissues or factors, including various cells of the immune system (e.g. effector cells) and the first component (C1q) of the classical complement system. The term antibody includes immunoglobulins of types IgA, IgG, IgE, IgD, IgM (as well as subtypes thereof), wherein the light chains of the immunoglobulin may be kappa or lambda types. The overall structure of immunoglobulin-gamma (IgG) antibodies assembled from two identical heavy (H)-chain and two identical light (L)-chain polypeptides is well established and highly conserved in mammals (Padlan 1994 *Mol Immunol* 31:169-217).

An exception to conventional antibody structure is found in sera of Camelidae. In addition to conventional antibodies, these sera possess special IgG antibodies. These IgG antibodies, known as heavy-chain antibodies (HCAbs), are devoid of the L chain polypeptide and lack the first constant domain (CH1). At its N-terminal region, the H chain of the homodimeric protein contains a dedicated immunoglobulin chain variable domain, referred to as the VHH, which serves to associate with its cognate antigen (Muyldermans 2013 *Annu Rev Biochem* 82:775-797, Hamers-Casterman et al 1993 *Nature* 363(6428):446-448, Muyldermans et al 1994 *Protein Eng* 7(9):1129-1135, herein incorporated by reference in their entirety).

An antigen-binding fragment (or "antibody fragment" or "immunoglobulin fragment") as used herein refers to a portion of an antibody that specifically binds to a target (e.g. a molecule in which one or more immunoglobulin chains is not full length, but which specifically binds to a target). Examples of binding fragments encompassed within the term antigen-binding fragment include:

(i) a Fab fragment (a monovalent fragment consisting of the VLC, VHC, CL and CH1 domains);
(ii) a F(ab')2 fragment (a bivalent fragment comprising two Fab fragments linked by a disulfide bridge at the hinge region);
(iii) a Fd fragment (consisting of the VHC and CH1 domains);
(iv) a Fv fragment (consisting of the VLC and VHC domains of a single arm of an antibody);
(v) an scFv fragment (consisting of VLC and VHC domains joined, using recombinant methods, by a synthetic linker that enables them to be made as a single protein chain in which the VLC and VHC regions pair to form monovalent molecules);
(vi) a VH (an immunoglobulin chain variable domain consisting of a VHC domain (Ward et al *Nature* 1989 341:544-546);
(vii) a VL (an immunoglobulin chain variable domain consisting of a VLC domain);
(viii) a V-NAR (an immunoglobulin chain variable domain consisting of a VHC domain from chondrichthyes IgNAR (Roux et al 1998 *Proc Natl Acad Sci USA* 95:11804-11809 and Griffiths et al 2013 Antibodies 2:66-81, herein incorporated by reference in their entirety)

(ix) a VHH.

The total number of amino acid residues in a VHH or VH may be in the region of 110-130, is suitably 112-120, and is most suitably 115.

Constructs of the invention comprising polypeptides and labile peptide linkers may for example be obtained by preparing a nucleic acid encoding two or more polypeptides and a labile peptide linker using techniques for nucleic acid synthesis, followed by expression of the nucleic acid thus obtained (as detailed further herein). According to a specific embodiment, a construct according to the invention does not have an amino acid sequence which is exactly the same as (i.e. shares 100% sequence identity with) the amino acid sequence of a naturally occurring polypeptide.

Suitably the first and/or second polypeptide of the construct of the invention is an antigen-binding polypeptide, more suitably the first and/or second antigen-binding polypeptide is an immunoglobulin chain variable domain, an antibody or an antigen-binding fragment thereof. More suitably the antigen-binding fragment is selected from the group consisting of: VLs, V-NARs, scFvs, Fab fragments, F(ab')2 fragments or immunoglobulin chain variable domains such as VHHs and VHs.

Specificity, Affinity and Avidity

Specificity refers to the number of different types of antigens or antigenic determinants to which a particular antigen-binding polypeptide can bind. The specificity of an antigen-binding polypeptide is the ability of the antigen-binding polypeptide to recognise a particular antigen as a unique molecular entity and distinguish it from another.

Affinity, represented by the equilibrium constant for the dissociation of an antigen with an antigen-binding polypeptide (Kd), is a measure of the binding strength between an antigenic determinant and an antigen-binding site on an antigen-binding polypeptide: the lesser the value of the Kd, the stronger the binding strength between an antigenic determinant and the antigen-binding polypeptide (alternatively, the affinity can also be expressed as the affinity constant (Ka), which is 1/Kd). Affinity can be determined by known methods, depending on the specific antigen of interest.

Avidity is the measure of the strength of binding between an antigen-binding polypeptide and the pertinent antigen. Avidity is related to both the affinity between an antigenic determinant and its antigen-binding site on the antigen-binding polypeptide and the number of pertinent binding sites present on the antigen-binding polypeptide.

Suitably, antigen-binding polypeptides bind with a dissociation constant (Kd) of $10^{-6}$ to $10^{-12}$ M, more suitably $10^{-7}$ to $10^{-12}$ M, more suitably $10^{-8}$ to $10^{-12}$ M and more suitably $10^{-9}$ to $10^{-12}$ M.

Any Kd value less than $10^{-6}$ is considered to indicate binding. Specific binding of an antigen-binding polypeptide to an antigen or antigenic determinant can be determined in any suitable known manner, including, for example, Scatchard analysis and/or competitive binding assays, such as radioimmunoassays (RIA), enzyme immunoassays (EIA) and sandwich competition assays, and the different variants thereof known in the art.

Polypeptide and Polynucleotide Sequences

The construct of the invention, the labile peptide linker and the first and second polypeptides comprised within the construct all comprise amino acid residues.

Suitably the first and second polypeptides each comprise or more suitably consists of a sequence selected from the group consisting of SEQ ID NO: 18 and SEQ ID NO: 19

Suitably the construct comprises or more suitably consists of a sequence selected from the group consisting of SEQ ID NOs: 7 to 17. Suitably the construct comprises or more suitably consists of a sequence selected from the group consisting of SEQ ID NOs: 8 to 11 and 13 to 16.

Suitably the labile peptide linker comprises or more suitably consists of a sequence selected from the group consisting of SEQ ID NOs: 1 to 6. Suitably the labile peptide linker comprises or more suitably consists of a sequence selected from the group consisting of SEQ ID NOs: 2 to 5.

An amino acid residue in regions of the construct other than the labile peptide linker can be replaced with another amino acid residue of similar chemical structure and which is expected to have little influence on the function, activity or other biological properties of the polypeptide. Such a substitution is a "conservative" substitution Such conservative substitutions suitably are substitutions in which one amino acid within the following groups is substituted by another amino acid residue from within the same group:

| Group | Amino acid residue |
| --- | --- |
| Non-polar aliphatic | Glycine |
|  | Alanine |
|  | Valine |
|  | Leucine |
|  | Isoleucine |
| Aromatic | Phenylalanine |
|  | Tyrosine |
|  | Tryptophan |
| Polar uncharged | Serine |
|  | Threonine |
|  | Asparagine |
|  | Glutamine |
| Negatively charged | Aspartate |
|  | Glutamate |
| Positively charged | Lysine |
|  | Arginine |

The construct, excluding the labile peptide linker, may suitably include one or more conservative substitutions.

In one aspect of the invention there is provided a nucleic acid encoding the construct of the invention.

For the avoidance of doubt, the single-letter amino acid code is as follows:

G—Glycine (Gly), P—Proline (Pro), A—Alanine (Ala), V—Valine (Val), L—Leucine (Leu), I—Isoleucine (Ile), M—Methionine (Met), C—Cysteine (Cys), F—Phenylalanine (Phe), Y—Tyrosine (Tyr), W—Tryptophan (Trp), H—Histidine (His), K—Lysine (Lys), R—Arginine (Arg), Q—Glutamine (Gin), N—Asparagine (Asn), E—Glutamic Acid (Glu), D—Aspartic Acid (Asp), S—Serine (Ser), T—Threonine (Thr).

Multimers

A construct according to the invention comprises a first polypeptide and a second polypeptide. The inventive construct is therefore multimeric and may suitably be multivalent. Such a construct may comprise a first polypeptide and a second polypeptide which are identical. A construct consisting of two identical polypeptides is a "homobihead". In one aspect of the invention there is provided a construct comprising two identical polypeptides. Alternatively, a construct may consist of a first polypeptide and a second polypeptide which are different from one another (a "heterobihead").

Constructs can be multivalent and/or multispecific. A multivalent construct (such as a bivalent construct) comprises two or more binding polypeptides and therefore provides two or more sites at which attachment to antigens can occur suitably before or after cleavage of the labile peptide linker. An example of a multivalent construct could be a homobihead or a heterobihead. A multispecific construct such as a bispecific construct comprises two different binding polypeptides which present two sites at which either (a) attachment to two different antigens can occur or (b) attachment to two different epitopes on the same antigen can occur, suitably before or after cleavage of the labile peptide linker. An example of a multispecific construct could be a heterobihead. A multispecific construct is multivalent.

A construct of the invention may comprise an additional third polypeptide (connected to the first polypeptide by a peptide linker) and may also comprise or consist of an additional fourth polypeptide (connected to the second polypeptide by a peptide linker), wherein the third and fourth polypeptides are substantially resistant to the one or more proteases present in the intestinal tract and are as defined herein in respect of the first and second polypeptides. A construct of the invention consisting of four polypeptides is known as a 'quadrahead'. Suitably, the peptide linkers are substantially resistant to the one or more proteases present in the intestinal tract or alternatively the peptide linkers are labile peptide linkers as defined herein.

Suitably the first, second, third and/or fourth polypeptide has a molecular weight of no greater than 300 kDa, such as 250 kDa, such as 200 kDa, such as 180 kDa, such as 160 kDa, such as 140 kDa, such as 120 kDa, such as 100 kDa, such as 80 kDa, such as 60 kDa.

The Gastrointestinal Tract and Digestive Enzymes

The gastrointestinal tract (GIT) is an organ system responsible for consuming and digesting foodstuffs, absorbing nutrients, and expelling waste. In humans and other mammals, the GIT consists of the oesophagus, stomach, small intestine (duodenum, jejunum and ileum) and large intestine (cecum, colon, rectum and anal canal). Various pathogens may colonise and various diseases may manifest in different areas of the GIT. The intestinal tract (as opposed to the gastrointestinal tract) consists of the small and large intestine.

The different parts of the gastrointestinal tract each contain a complex mixture of digestive enzymes. These digestive enzymes include proteases, lipases, amylases and nucleases. Proteases include serine proteases, threonine proteases, cysteine proteases, aspartate proteases, glutamic acid proteases and metalloproteases. Proteases are involved in digesting polypeptide chains into shorter fragments by splitting the peptide bonds that link amino acid residues (proteolysis). Some detach the terminal amino acids from the protein chain (exopeptidases), others attack internal peptide bonds of a protein (endopeptidases).

Proteolysis can be highly promiscuous such that a wide range of protein substrates are hydrolysed. This is the case for proteases which cleave the wide array of ingested polypeptides in the intestinal tract into smaller polypeptide fragments.

Many proteases typically bind to a single amino acid (a labile site) on the substrate and so only have specificity for that residue. The proteases present in the intestinal tract include trypsin, trypsin-like proteases, chymotrypsin, chymotrypsin-like proteases, carboxypeptidase, elastase, aminopeptidase, carboxypeptidase and enteropeptidase. Trypsin-like proteases cleave peptide bonds following lysine or arginine residues. Chymotrypsin-like proteases cleave peptide bonds following hydrophobic residues, such as tyrosine, phenylalanine, tryptophan, leucine and methionine. Particularly tyrosine, phenylalanine and tryptophan.

Suitably the labile peptide linker is labile to one or more proteases present in the intestinal tract and wherein the first and second polypeptides are substantially resistant to said one or more proteases, wherein said one or more proteases are present in the small or large intestine, more suitably the jejunum, the ileum and/or the cecum. Suitably the one or more proteases are serine proteases. Suitably the one or more proteases are selected from the group consisting of enteropeptidase, trypsin, trypsin-like proteases, chymotrypsin and chymotrypsin-like proteases.

Suitably the first and second polypeptides of the construct of the invention are substantially resistant to all proteases present in the intestinal tract. Such proteases include proteases sourced from gastrointestinal tract commensal microflora or pathogenic bacteria, for example wherein the proteases are cell membrane-attached proteases, secreted proteases and proteases released on cell lysis. Suitably the intestinal tract is a mammalian intestinal tract, such as a human, simian, murine, bovine, ovine or porcine intestinal tract.

Diseases of the GIT

Diseases of the GIT refer to diseases involving the gastrointestinal tract, namely the oesophagus, stomach, small intestine (duodenum, jejunum and ileum) and large intestine (cecum, colon, rectum and anal canal). The construct of the invention may be used in the treatment or prevention of such diseases. Exemplary diseases of the GIT are described below.

Autoimmune Diseases and/or Inflammatory Diseases of the GIT

Autoimmune diseases develop when the immune system responds adversely to normal body tissues. Autoimmune disorders may result in damage to body tissues, abnormal organ growth and/or changes in organ function. The disorder may affect only one organ or tissue type or may affect multiple organs and tissues. Organs and tissues commonly affected by autoimmune disorders include blood components such as red blood cells, blood vessels, connective tissues, endocrine glands such as the thyroid or pancreas, muscles, joints and skin. An inflammatory disease is a disease characterised by inflammation. Many inflammatory diseases are autoimmune diseases and vice-versa.

The chronic inflammatory bowel diseases (IBD) Crohn's disease and ulcerative colitis, which afflict both children and adults, are examples of autoimmune and inflammatory diseases of the GIT (Hendrickson et al 2002 *Clin Microbiol Rev* 15(1):79-94, herein incorporated by reference in its entirety). Ulcerative colitis is defined as a condition where the inflammatory response and morphologic changes remain confined to the colon. The rectum is involved in 95% of patients. Inflammation is largely limited to the mucosa and consists of continuous involvement of variable severity with ulceration, edema, and hemorrhage along the length of the colon (Hendrickson et al 2002 *Clin. Microbiol Rev* 15(1): 79-94, herein incorporated by reference in its entirety). Ulcerative colitis is usually manifested by the presence of blood and mucus mixed with stool, along with lower abdominal cramping which is most severe during the passage of bowel movements. Clinically, the presence of diarrhoea with blood and mucus differentiates ulcerative colitis from irritable bowel syndrome, in which blood is absent. Unlike ulcerative colitis, the presentation of Crohn's disease is usually subtle, which leads to a later diagnosis. Factors such as the location, extent, and severity of involvement determine the extent of gastrointestinal symptoms. Patients who have ileocolonic involvement usually have postprandial abdominal pain, with tenderness in the right lower quadrant and an occasional inflammatory mass.

Suitably the pharmaceutical composition or construct of the invention is for use in the treatment of an autoimmune and/or inflammatory disease of the GIT selected from the list consisting of Crohn's disease, ulcerative colitis, irritable bowel syndrome, diabetes type II, glomerulonephritis, autoimmune hepatitis, Sjogren's syndrome, celiac disease and drug- or radiation-induced mucositis (most suitably Crohn's disease).

Infection of the GIT

Viral, bacterial, parasitic and other pathogenic infections can occur in the GIT. These may be confined to the GIT or initiated in the GIT before spreading to other parts of the body. The construct of the invention may be used for the treatment or prevention of bacterial infection including infection by common bacterial GIT pathogens including *Escherichia coli, Salmonella, Campylobacter, Vibrio cholerae, Shigella, Clostridium perfringens, Clostridium difficile, Bacillus cereus, Vibrio parahaemolyticus, Yersinia enerocolitica*. The construct of the invention may be used for the treatment or prevention of viral infection including common viral GIT pathogens which include rotavirus, norovirus and small round viruses. Suitably the construct of the invention is for use in the treatment or prevention of nosocomial infection. Suitably the construct of the invention is for use in the treatment or prevention of *C. difficile* infection.

Suitably, the first and/or second polypeptide of the construct of the invention binds to a target accessible via the intestinal tract such as a target within the intestinal tract. Suitably the target is a deleterious agent originating from an intestinal tract resident pathogenic microbe. Suitably the target is selected from the group consisting of: an interleukin (such as IL-1, IL-1ra, IL-4, IL-5, IL-6, IL-7, IL-8, IL-9, IL-10, IL-11, IL-12, IL-13, IL-15, IL-17, IL-18 and IL-23), an interleukin receptor (such as IL-6R and IL-7R), a transcription factor (such as NF-kB), a cytokine (such as TNF-alpha, IFN-gamma TGF-beta and TSLP), a transmembrane protein (such as gp130 and CD3), a surface glycoprotein (such as CD4, CD20, CD40), a soluble protein (such as CD40L), an integrin (such as a4b7 and AlphaEbeta7), an adhesion molecule (such as MAdCAM), a chemokine (such as IP10 and CCL20), a chemokine receptor (such as CCR2 and CCR9), an inhibitory protein (SMAD7), a kinase (such as JAK3), a G protein-coupled receptor (such as sphingosine-1-P receptor) and a toxin (such as *C. difficile* toxin A and *C. difficile* toxin B); more suitably the target is selected from the group consisting of: TNF-alpha, *C. difficile* toxin A, *C. difficile* toxin B, CD3 and IL-6R; more suitably TNF-alpha or *C. difficile* toxin A. Suitably the target of the first and second polypeptides are identical or different.

In one embodiment the first and/or second polypeptide of the construct of the invention (such as the first and/or second immunoglobulin chain variable domain) does not bind to an interleukin (such as IL-1, IL-1ra, IL-4, IL-5, IL-6, IL-7, IL-8, IL-9, IL-10, IL-11, IL-12, IL-13, IL-15, IL-17, IL-18 and IL-23).

In a further embodiment the first and/or second polypeptide of the construct of the invention (such as the first and/or second immunoglobulin chain variable domain) does not bind to an interleukin receptor (such as IL-6R and IL-7R).

In a further embodiment the first and/or second polypeptide of the construct of the invention (such as the first and/or second immunoglobulin chain variable domain) does not bind to a transcription factor (such as NF-kB).

In a further embodiment the first and/or second polypeptide of the construct of the invention (such as the first and/or second immunoglobulin chain variable domain) does not bind to a cytokine (such as TNF-alpha, IFN-gamma TGF-beta and TSLP).

In a further embodiment the first and/or second polypeptide of the construct of the invention (such as the first and/or second immunoglobulin chain variable domain) does not bind to a transmembrane protein (such as gp130 and CD3).

In a further embodiment the first and/or second polypeptide of the construct of the invention (such as the first and/or second immunoglobulin chain variable domain) does not bind to a surface glycoprotein (such as CD4, CD20 and CD40).

In a further embodiment the first and/or second polypeptide of the construct of the invention (such as the first and/or second immunoglobulin chain variable domain) does not bind to a soluble protein (such as CD40L).

In a further embodiment the first and/or second polypeptide of the construct of the invention (such as the first and/or second immunoglobulin chain variable domain) does not bind to an integrin (such as a4b7 and AlphaEbeta7).

In a further embodiment the first and/or second polypeptide of the construct of the invention (such as the first and/or second immunoglobulin chain variable domain) does not bind to an adhesion molecule (such as MAdCAM)

In a further embodiment the first and/or second polypeptide of the construct of the invention (such as the first and/or second immunoglobulin chain variable domain) does not bind to a chemokine (such as IP10 and CCL20).

In a further embodiment the first and/or second polypeptide of the construct of the invention (such as the first and/or second immunoglobulin chain variable domain) does not bind to a chemokine receptor (such as CCR2 and CCR9).

In a further embodiment the first and/or second polypeptide of the construct of the invention (such as the first and/or second immunoglobulin chain variable domain) does not bind to an inhibitory protein (SMAD7).

In a further embodiment the first and/or second polypeptide of the construct of the invention (such as the first and/or second immunoglobulin chain variable domain) does not bind to a kinase (such as JAK3).

In a further embodiment the first and/or second polypeptide of the construct of the invention (such as the first and/or second immunoglobulin chain variable domain) does not bind to a G protein-coupled receptor (such as sphingosine-1-P receptor).

In a further embodiment the first and/or second polypeptide of the construct of the invention (such as the first and/or second immunoglobulin chain variable domain) does not bind to a toxin (such as *C. difficile* toxin A and *C. difficile* toxin B).

Therapeutic Use and Delivery

Suitably the construct or composition of the invention is for use as a medicament, suitably administered by oral administration, suitably for use in the treatment or prevention of diseases of the GIT (see intra). The construct or composition of the invention may also be used in the treatment or prevention of other medical conditions by oral administration such as metabolic disorders, such as obesity. In one embodiment, the construct or composition of the invention is intended to have local effect in the intestinal tract. In one embodiment, the construct or composition of the invention is not for use in the treatment or prevention of diseases by delivery into the circulation in therapeutically effective quantities.

In one aspect of the invention there is provided a method of treating autoimmune disease or *C. difficile* infection comprising administering to a person in need thereof a therapeutically effective amount of the inventive construct or composition.

A therapeutically effective amount of a construct of the invention is an amount which is effective, upon single or multiple dose administration to a subject, in neutralising the biological effects of a chosen target to a significant extent in a subject. A therapeutically effective amount may vary according to factors such as the disease state, age, sex, and weight of the individual, and the ability of the construct to elicit a desired response in the individual. A therapeutically effective amount is also one in which any toxic or detrimental effects of the construct are outweighed by the therapeutically beneficial effects. The construct of the invention can be incorporated into pharmaceutical compositions suitable for oral administration to a subject. The construct of the invention can be in the form of a pharmaceutically acceptable salt.

In one aspect of the invention there is provided a method of treating a disease with a monomeric antibody or a monomeric antigen binding fragment thereof, comprising administering to a subject the inventive construct. There is also provided a method of treating a disease with two or more monomeric antibodies or monomeric antigen binding fragments thereof, comprising administering to a subject the inventive construct.

A pharmaceutical composition of the invention is formulated for oral delivery. The pharmaceutical compositions of the invention may be in a variety of forms. These include, for example, liquid, semi-solid and solid dosage forms, such as liquid solutions, dispersions or suspensions, tablets, pills and powders. Solid dosage forms are preferred. The pharmaceutical composition may comprise a pharmaceutically acceptable excipient, and suitably may be used in the form of ingestible tablets, buccal tablets, troches, capsules, elixirs, suspensions, syrups, wafers, and the like.

Typically, the pharmaceutical composition comprises a construct of the invention and a pharmaceutically acceptable excipient such as a carrier. Examples of pharmaceutically acceptable carriers include one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the polypeptide or construct of the invention. Pharmaceutical compositions may include antiadherents, binders, coatings, disintegrants, flavours, colours, lubricants, sorbents, preservatives, sweeteners, freeze dry excipients (including lyoprotectants) or compression aids. Suitably, the construct of the invention is lyophilised before being incorporated into a pharmaceutical composition.

Suitably, the first and second polypeptides of the construct are substantially resistant to all proteases present in the intestinal tract by virtue of the inherent properties of the polypeptides or construct itself.

A polypeptide of the invention may also be provided with an enteric coating. An enteric coating is a polymer barrier applied on oral medication which protects the polypeptide from the low pH of the stomach. Materials used for enteric coatings include fatty acids, waxes, shellac, plastics, and plant fibers. Suitable enteric coating components include methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), methyl methacrylate-methacrylic acid copolymers, sodium alginate and stearic acid. Suitable enteric coatings include pH-dependent release polymers. These are polymers which are insoluble at the highly acidic pH found in the stomach, but which dissolve rapidly at a less acidic pH. Thus, suitably, the enteric coating will not dissolve in the acidic juices of the stomach (pH~3), but will do so in the higher pH environment present in the small intestine (pH above 6) or in the colon (pH above 7.0). The pH-dependent release polymer is selected such that the construct of the invention will be released at about the time that the dosage reaches the target region of the intestinal tract.

The pharmaceutical composition or construct of the invention may be formulated in a buffer, in order to stabilise the pH of the composition, at a concentration between 5-50, or more suitably 15-40 or more suitably 25-30 g/litre. Examples of suitable buffer components include physiological salts such as sodium citrate and/or citric acid. Suitably buffers contain 100-200, more suitably 125-175 mM physiological salts such as sodium chloride. Suitably the buffer is selected to have a pKa close to the pH of the composition or the physiological pH of the patient.

Exemplary construct concentrations in a pharmaceutical composition may range from about 1 mg/mL to about 200 mg/ml or from about 50 mg/mL to about 200 mg/mL, or from about 150 mg/mL to about 200 mg/mL.

An aqueous formulation of the construct or pharmaceutical composition of the invention may be prepared in a pH-buffered solution, e.g., at pH ranging from about 4.0 to about 7.0, or from about 5.0 to about 6.0, or alternatively about 5.5. Examples of suitable buffers include phosphate-, histidine-, citrate-, succinate-, acetate-buffers and other organic acid buffers. The buffer concentration can be from about 1 mM to about 100 mM, or from about 5 mM to about 50 mM, depending, for example, on the buffer and the desired tonicity of the formulation.

The tonicity of the pharmaceutical composition may be altered by including a tonicity modifier. Such tonicity modifiers can be charged or uncharged chemical species. Typical uncharged tonicity modifiers include sugars or sugar alcohols or other polyols, preferably trehalose, sucrose, mannitol, glycerol, 1,2-propanediol, raffinose, sorbitol or lactitol (especially trehalose, mannitol, glycerol or 1,2-propanediol). Typical charged tonicity modifiers include salts such as a combination of sodium, potassium or calcium ions, with chloride, sulfate, carbonate, sulfite, nitrate, lactate, succinate, acetate or maleate ions (especially sodium chloride or sodium sulphate); or amino acids such as arginine or histidine. Suitably, the aqueous formulation is isotonic, although hypertonic or hypotonic solutions may be suitable. The term "isotonic" denotes a solution having the same tonicity as some other solution with which it is compared, such as physiological salt solution or serum. Tonicity agents may be used in an amount of about 5 mM to about 350 mM, e.g., in an amount of 1 mM to 500 nM. Suitably, at least one isotonic agent is included in the composition.

A surfactant may also be added to the pharmaceutical composition to reduce aggregation of the formulated construct and/or minimize the formation of particulates in the formulation and/or reduce adsorption. Exemplary surfactants include polyoxyethylensorbitan fatty acid esters (Tween), polyoxyethylene alkyl ethers (Brij), alkylphenylpolyoxyethylene ethers (Triton-X), polyoxyethylenepolyoxypropylene copolymer (Poloxamer, Pluronic), and sodium dodecyl sulfate (SDS). Examples of suitable polyoxyethylenesorbitan-fatty acid esters are polysorbate 20, and polysorbate 80. Exemplary concentrations of surfactant may range from about 0.001% to about 10% w/v.

A lyoprotectant may also be added in order to protect the construct of the invention against destabilizing conditions during the lyophilization process. For example, known lyoprotectants include sugars (including glucose, sucrose, mannose and trehalose); polyols (including mannitol, sorbitol and glycerol); and amino acids (including alanine, glycine and glutamic acid). Lyoprotectants can be included in an amount of about 10 mM to 500 mM.

The dosage ranges for administration of the pharmaceutical composition or construct of the invention are those to produce the desired therapeutic effect. The dosage range required depends on the precise nature of the pharmaceutical composition or construct, the target region of the intestinal tract, the nature of the formulation, the age of the patient, the nature, extent or severity of the patients condition, contraindications, if any, and the judgement of the attending physician. Variations in these dosage levels can be adjusted using standard empirical routines for optimisation.

Suitable daily dosages of pharmaceutical composition or construct of the invention are in the range of 50 ng-50 mg per kg, such as 50 ug-40 mg per kg, such as 5-30 mg per kg of body weight. The unit dosage can vary from less than 100 mg, but typically will be in the region of 250-2000 mg per dose, which may be administered daily or more frequently, for example 2, 3 or 4 times per day or less frequently for example every other day or once per week.

Treatment of diseases also embraces treatment of exacerbations thereof and also embraces treatment of patients in remission from disease symptoms to prevent relapse of disease symptoms.

Combination Therapy

A pharmaceutical composition of the invention may also comprise one or more active agents (e.g. active agents suitable for treating diseases such as those mentioned herein). It is within the scope of the invention to use the pharmaceutical composition of the invention in therapeutic methods for the treatment of bacterial infection, autoimmune and/or inflammatory diseases as an adjunct to, or in conjunction with, other established therapies normally used in the treatment of bacterial, autoimmune and/or inflammatory diseases.

For the treatment of irritable bowel disease (such as Crohn's disease or ulcerative colitis), possible combinations include combinations with, for example, one or more active agents selected from the list comprising: 5-aminosalicylic acid, or a prodrug thereof (such as sulfasalazine, olsalazine or bisalazide); corticosteroids (e.g. prednisolone, methylprednisolone, or budesonide); immunosuppressants (e.g. cyclosporin, tacrolimus, methotrexate, azathioprine or 6-mercaptopurine); anti-TNF-alpha antibodies (e.g., infliximab, adalimumab, certolizumab pegol or golimumab); anti-IL12/IL23 antibodies (e.g., ustekinumab); anti-IL6R antibodies or small molecule IL12/IL23 inhibitors (e.g., apilimod); Anti-alpha-4-beta-7 antibodies (e.g., vedolizumab); MAdCAM-1 blockers (e.g., PF-00547659); antibodies against the cell adhesion molecule alpha-4-integrin (e.g., natalizumab); antibodies against the IL2 receptor alpha subunit (e.g., daclizumab or basiliximab); JAK3 inhibitors (e.g., tofacitinib or R348); Syk inhibitors and prodrugs thereof (e.g., fostamatinib and R-406); Phosphodiesterase-4 inhibitors (e.g., tetomilast); HMPL-004; probiotics; Dersalazine; semapimod/CPSI-2364; and protein kinase C inhibitors (e.g. AEB-071). The most suitable combination agents are infliximab, adalimumab, certolizumab pegol or golimumab.

For the treatment of bacterial infections, such as *Clostridium difficile* infection, possible combinations include combinations with, for example, one or more active agents selected from the list comprising *C. difficile* toxoid vaccine, ampicillin, amoxicillin, vancomycin, metronidazole, fidaxomicin, linezolid, nitazoxanide, rifaximin, ramoplanin, difimicin, clindamycin, cephalosporins (such as second and third generation cephalosporins), fluoroquinolones (such as gatifloxacin or moxifloxacin), macrolides (such as erythromycin, clarithromycin, azithromycin), penicillins, aminoglycosides, trimethoprim-sulfamethoxazole, chloramphenicol, tetracycline, imipenem, meropenem, antibacterial agents, bactericides, or bacteriostats. Possible combinations also include combinations with one or more active agents which are probiotics, for example *Saccharomyces boulardii* or *Lactobacillus rhamnosus* GG.

Hence another aspect of the invention provides a pharmaceutical composition of the invention in combination with one or more further active agents, for example one or more active agents described above. In a further aspect of the invention, the pharmaceutical composition or construct is administered sequentially, simultaneously or separately with at least one active agent selected from the list above.

Similarly, another aspect of the invention provides a combination product comprising:

(A) a pharmaceutical composition or construct of the present invention; and
(B) one or more other active agents, wherein each of components (A) and (B) is formulated in admixture with a pharmaceutically-acceptable adjuvant, diluent or carrier. In this aspect of the invention, the combination product may be either a single (combination) formulation or a kit-of-parts. Thus, this aspect of the invention encompasses a combination formulation including a pharmaceutical composition or construct of the present invention and another therapeutic agent, in admixture with a pharmaceutically acceptable adjuvant, diluent or carrier.

The invention also encompasses a kit of parts comprising components:

(i) a pharmaceutical composition or construct of the present invention in admixture with a pharmaceutically acceptable adjuvant, diluent or carrier; and
(ii) a formulation including one or more other active agents, in admixture with a pharmaceutically-acceptable adjuvant, diluent or carrier, which components (i) and (ii) are each provided in a form that is suitable for administration in conjunction with the other.

Component (i) of the kit of parts is thus component (A) above in admixture with a pharmaceutically acceptable adjuvant, diluent or carrier. Similarly, component (ii) is component (B) above in admixture with a pharmaceutically acceptable adjuvant, diluent or carrier. The one or more other active agents (i.e. component (B) above) may be, for example, any of the agents mentioned above in connection with the treatment of bacterial infection such as *Clostridium difficile* infection, autoimmune and/or inflammatory diseases such as IBD (e.g. Crohn's disease and/or ulcerative colitis). If component (B) is more than one further active agent, these further active agents can be formulated with each other or formulated with component (A) or they may be formulated separately. In one embodiment component (B) is one other therapeutic agent. In another embodiment component (B) is two other therapeutic agents. The combination product (either a combined preparation or kit-of-parts) of this aspect of the invention may be used in the treatment or prevention of an autoimmune disease (e.g. the autoimmune diseases mentioned herein).

Vectors and Hosts

The term "vector", as used herein, is intended to refer to a nucleic acid molecule capable of transporting another nucleic acid to which it has been linked. One type of vector is a plasmid, which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian and yeast vectors). Other vectors (e.g. non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g. replication defective retroviruses. adenoviruses and adeno-associated viruses), which serve equivalent functions, and also bacteriophage and phagemid systems. The invention also relates to nucleotide sequences that encode constructs of the invention. The term "recombinant host cell" (or simply "host cell"), as used herein, is intended to refer to a cell into which a recombinant expression vector has been introduced. Such terms are intended to refer not only to the particular subject cell but to the progeny of such a cell.

In one aspect of the invention there is provided a vector comprising the polynucleotide encoding the construct of the invention or cDNA comprising said polynucleotide. In a further aspect of the invention there is provided a host cell transformed with said vector, which is capable of expressing the construct of the invention. Suitably the host cell is a yeast such as a yeast belonging to the genera *Aspergillus, Saccharomyces, Kluyveromyces, Hansenula* or *Pichia*, such as *Saccharomyces cerevisiae, Escherichia coli* or *Pichia pastoris*.

It is particularly advantageous for production and convenience purposes if the labile peptide linker is cleaved by proteases present in the intestinal tract, but if the labile peptide linker is also substantially resistant to proteases of the host organism in which the construct is produced. Therefore, in one embodiment of the invention, the labile peptide linker is substantially resistant to proteases of the host organism in which the construct is produced.

Preparative Methods

Constructs of the invention can be obtained and manipulated using the techniques disclosed for example in Green and Sambrook 2012 *Molecular Cloning: A Laboratory Manual* 4$^{th}$ Edition Cold Spring Harbour Laboratory Press.

In particular, artificial gene synthesis may be used to produce a construct according to the invention (Nambiar et al 1984 *Science* 223:1299-1301, Sakamar and Khorana 1988 *Nucl. Acids Res* 14:6361-6372, Wells et al 1985 *Gene* 34:315-323 and Grundstrom et al 1985 *Nucl. Acids Res* 13:3305-3316, herein incorporated by reference in their entirety). A gene encoding a construct of the invention can be synthetically produced by, for example, solid-phase DNA synthesis. Entire genes may be synthesized de novo, without the need for precursor template DNA. To obtain the desired oligonucleotide, the building blocks are sequentially coupled to the growing oligonucleotide chain in the order required by the sequence of the product. Upon the completion of the chain assembly, the product is released from the solid phase to solution, deprotected, and collected. Products can be isolated by high-performance liquid chromatography (HPLC) to obtain the desired oligonucleotides in high purity (Verma and Eckstein 1998 *Annu Rev Biochem* 67:99-134).

The constructs of the invention may be fused genetically at the DNA level i.e. a polynucleotide construct which encodes the complete polypeptide construct comprising one or more polypeptides such as antigen-binding polypeptides. One way of joining multiple polypeptides via the genetic route is by linking the polypeptide coding sequences via a labile peptide linker coding sequence. For example, the carboxy-terminal end of the first polypeptide may be linked to the amino-terminal end of the next polypeptide via a labile peptide linker coding sequence. This linking mode can be extended in order to link polypeptides for the construction of tri-, tetra-, etc. functional constructs. A method for producing multivalent (such as bivalent) VHH polypeptide constructs is disclosed in WO96/34103 (herein incorporated by reference in its entirety).

Mutations can be made to the DNA or cDNA that encode constructs which are silent as to the amino acid sequence of the polypeptide, but which provide preferred codons for translation in a particular host. The preferred codons for translation of a nucleic acid in, e.g., *E. coli* and *S. cerevisiae*, are known.

Mutation of constructs can be achieved for example by substitutions, additions or deletions to a nucleic acid encoding the construct. The substitutions, additions or deletions to a nucleic acid encoding the construct can be introduced by many methods, including for example error-prone PCR, shuffling, oligonucleotide-directed mutagenesis, assembly PCR, PCR mutagenesis, in vivo mutagenesis, cassette mutagenesis, recursive ensemble mutagenesis, exponential ensemble mutagenesis, site-specific mutagenesis (Ling et al 1997 *Anal Biochem* 254(2):157-178, herein incorporated by reference in its entirety), gene reassembly, Gene Site Saturation Mutagenesis (GSSM), synthetic ligation reassembly (SLR) or a combination of these methods. The modifications, additions or deletions to a nucleic acid can also be introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, ensemble mutagenesis, chimeric nucleic acid multimer creation, or a combination thereof.

Expression of constructs comprising immunoglobulin chain variable domains such as VHs and VHHs can be achieved using a suitable expression vector such as a prokaryotic cell such as bacteria, for example *E. coli* (for example according to the protocols disclosed in WO94/04678 and WO96/34103, which are incorporated herein by reference). Expression of immunoglobulin chain variable domains such as VHs and VHHs can also be achieved using eukaryotic cells, for example insect cells, CHO cells, Vero cells or suitably yeast cells such as yeasts belonging to the genera *Aspergillus, Saccharomyces, Kluyveromyces, Hansenula* or *Pichia*. Suitably *S. cerevisiae* is used (for example according to the protocols disclosed in WO94/025591, which is incorporated herein by reference).

Suitably, the construct of the invention can be produced in a fungus such as a yeast (for example, *S. cerevisiae*) comprising growth of the fungus on a medium comprising a carbon source wherein 50-100 wt % of said carbon source is ethanol, according to the methods disclosed in WO02/48382.

In one aspect of the invention there is provided a process for the preparation of the construct of the invention comprising the following steps:
  i) cloning into a vector, such as a plasmid, the polynucleotide of the invention,
  ii) transforming a cell, such as a bacterial cell or a yeast cell capable of producing the construct of the invention, with said vector in conditions allowing the production of the construct,
  iii) recovering the construct, such as by affinity chromatography.

Clauses

A set of clauses defining the invention and its preferred aspects is as follows:
1. A construct suitable for oral administration comprising a first polypeptide and a second polypeptide connected by a labile peptide linker, wherein the labile peptide linker is labile to one or more proteases present in the intestinal tract and wherein the first and second polypeptides are substantially resistant to said one or more proteases.
2. The construct according to clause 1, wherein the first polypeptide is an antigen-binding polypeptide.
3. The construct according to clause 2, wherein the antigen-binding polypeptide is an antibody or an antigen-binding fragment thereof.
4. The construct according to any one of clauses 1 to 3, wherein the second polypeptide is an antigen-binding polypeptide.
5. The construct according to clause 4, wherein the second antigen-binding polypeptide is an antibody or an antigen-binding fragment thereof.
6. The construct according to any one of clauses 1 to 5 wherein the first and second polypeptides are substantially resistant to all proteases present in the intestinal tract.
7. The construct according to any one of clauses 1 to 6 wherein the intestinal tract is a mammalian intestinal tract, such as a human, simian, murine, bovine, ovine or porcine intestinal tract.
8. The construct according to any one of clauses 1 to 7, wherein the one or more proteases are present in the small or large intestine.
9. The construct according to clause 8, wherein the one or more proteases are present in the jejunum, the ileum and/or the cecum.
10. The construct according to either clause 8 or 9, wherein the one or more proteases are serine proteases.
11. The construct according to any one of clauses 1 to 10, wherein the labile peptide linker is substantially resistant to proteases of the host organism in which the construct is produced.
12. The construct according to any one of clauses 1 to 11, wherein the labile peptide linker comprises a cleavage site for trypsin or a trypsin-like protease.
13. The construct according to clause 12, wherein the labile peptide linker comprises at least 1, such as at least 2, such as at least 3, such as at least 4, such as at least 5, such as at least 6, such as at least 7, such as at least 8, such as at least 9, such as at least 10 K residues.
14. The construct according to any one of clauses 1 to 13, wherein the labile peptide linker comprises at least 1, such as at least 2, such as at least 3, such as at least 4, such as at least 5, such as at least 6, such as at least 7, such as at least 8, such as at least 9, such as at least 10 R residues.
15. The construct according to any one of clauses 1 to 14, wherein the labile peptide linker does not comprise any P residues.
16. The construct according to any one of clauses 1 to 15, wherein all K or R residues comprised within the labile peptide linker have at least 1, such as at least 2, such as at least 3, such as at least 4, such as at least 5 shielding residues on their N-terminal side, wherein the shielding residues are selected from the list consisting of: D and E.
17. The construct according to any one of clauses 1 to 16, wherein all K or R residues comprised within the labile peptide linker have at least 1, such as at least 2, such as at least 3, such as at least 4, such as at least 5 shielding residues on their C-terminal side, wherein the shielding residues are selected from the list consisting of: D and E.
18. The construct according to either clause 16 or 17, wherein all K and R residues have at least one shielding residue adjacent to them.
19. The construct according to any one of clauses 1 to 18, wherein the labile peptide linker does not comprise any D or E residues.
20. The construct according to any one of clauses 1 to 18, wherein the labile peptide linker consists of residues selected from the list consisting of C, A, S, N, G, L, I, V, T, M, F, Y, H, K, R, W and Q.
21. The construct according to clause 20, wherein the labile peptide linker consists of residues selected from the list consisting of A, G, L, I, V, M, S, T, K and R residues.
22. The construct according to clause 21, wherein the labile peptide linker consists of residues selected from the list consisting of S, G, K and R.
23. The construct according to any one of clauses 1 to 15, wherein all K or R residues comprised within the labile peptide linker have at least 1, such as at least 2, such as at least 3, such as at least 4, such as at least 5 non-shielding residues on their N-terminal side, wherein the non-shielding residues are selected from the list consisting of: C, A, S, N, G, L, I, V, T, M, F, Y, H, W and Q.
24. The construct according to any one of clauses 1 to 15 and 23, wherein all K or R residues comprised within the labile peptide linker have at least 1, such as at least 2, such as at least 3, such as at least 4, such as at least 5 non-shielding residues on their C-terminal side, wherein the non-shielding residues are selected from the list consisting of: C, A, S, N, G, L, I, V, T, M, F, Y, H, W and Q.
25. The construct according to either clause 23 or 24, wherein all K and R residues have at least one non-shielding residue adjacent to them.
26. The construct according to any one of clauses 23 to 25, wherein the non-shielding residues are selected from the list consisting of: A, G, L, I, V, M, S and T.
27. The construct according to clause 26, wherein the non-shielding residues are selected from the list consisting of: A, G, L, I, V and S.

28. The construct according to clause 27, wherein the non-shielding residues are selected from the list consisting of: G and S.
29. The construct according to any one of clauses 1 to 11, wherein the labile peptide linker comprises a cleavage site for chymotrypsin or a chymotrypsin-like protease.
30. The construct according to clause 29, wherein the labile peptide linker comprises at least 1, such as at least 2, such as at least 3, such as at least 4, such as at least 5, such as at least 6, such as at least 7, such as at least 8, such as at least 9, such as at least 10 residues selected from the list consisting of W, F, Y, L and M.
31. The construct according to clause 30, wherein the labile peptide linker comprises at least 1, such as at least 2, such as at least 3, such as at least 4, such as at least 5, such as at least 6, such as at least 7, such as at least 8, such as at least 9, such as at least 10 residues selected from the list consisting of W, F and Y.
32. The construct according to any one of clauses 29 to 31, wherein the labile peptide linker consists of residues selected from the list consisting of S, G, W, F, Y, L and M;
such as S, G, W, F and Y.
33. The construct according to any one of clauses 1 to 32, wherein the labile peptide linker has a length of at least 3 residues, such as at least 5 residues, such as at least 10 residues.
34. The construct according to any one of clauses 1 to 33, wherein the labile peptide linker has a length of no greater than 40 residues, such as no greater than 25 residues, such as no greater than 15 residues.
35. The construct according to clause 1, wherein the labile peptide linker comprises or more suitably consists of a polypeptide sequence of the format:

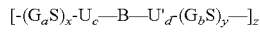

wherein
a is 1 to 10;
b is 1 to 10;
U is D or E;
U' is D or E;
c is 0 to 7;
d is 0 to 7;
x is 1 to 10;
y is 1 to 10
z is 1 to 10 and
B is K or R.
36. The construct according to clause 35, wherein the labile peptide linker comprises or more suitably consists of a polypeptide sequence of the format:

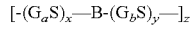

wherein
a is 1 to 10;
b is 1 to 10;
x is 1 to 10;
y is 1 to 10
z is 1 to 10 and
B is K or R.
37. The construct according to clause 36, wherein the labile peptide linker comprises or more suitably consists of a polypeptide sequence of the format:

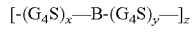

wherein
x is 1 to 10;
y is 1 to 10
z is 1 to 10 and
B is K or R.
38. The construct according to clause 1, wherein the labile peptide linker comprises or more suitably consists of a polypeptide sequence of the format:

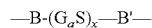

wherein
a is 1 to 10;
x is 1 to 10;
B is K or R and
B' is K or R.
39. The construct according to clause 1, wherein the labile peptide linker comprises or more suitably consists of a polypeptide sequence of the format:

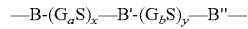

wherein
a is 1 to 10;
b is 1 to 10;
x is 1 to 10;
y is 1 to 10;
B is K or R
B' is K or R and
B" is K or R.
40. The construct according to any one of clauses 35 to 39, wherein a is 2 to 5.
41. The construct according to clause 40, wherein a is 4.
42. The construct according to any one of clauses 35 to 41, wherein b is 2 to 5.
43. The construct according to clause 42, wherein b is 4.
44. The construct according to any one of clauses 35 to 43, wherein x is 1 to 5.
45. The construct according to clause 44, wherein x is 2.
46. The construct according to clause 44, wherein x is 1.
47. The construct according to any one of clauses 35 to 46, wherein y is 1 to 5.
48. The construct according to clause 47, wherein y is 1.
49. The construct according to clause 47, wherein y is 2.
50. The construct according to any one of clauses 35 to 49, wherein z is 1 to 3.
51. The construct according to clause 50, wherein z is 1.
52. The construct according to any one of clauses 35 to 51, wherein B is K.
53. The construct according to any one of clauses 35 to 52, wherein U is D.
54. The construct according to any one of clauses 35 to 53, wherein U' is D.
55. The construct according to any one of clauses 35 to 54, wherein c is 1.
56. The construct according to any one of clauses 35 to 55, wherein d is 1.
57. The construct according to any one of clauses 35 to 54, wherein c is 0.
58. The construct according to any one of clauses 35 to 55 or 57, wherein d is 0.
59. The construct according to any one of clauses 35 to 54, wherein c is 4 and d is 0.
60. The construct according to any one of clauses 35 to 59, wherein B' is K.
61. The construct according to any one of clauses 35 to 60, wherein B" is K.

62. The construct according to clause 1, wherein the labile peptide linker comprises or more suitably consists of a polypeptide sequence of the format:

$$[-(G_aS)_x\text{-}J\text{-}(G_bS)_y-]_z$$

wherein
a is 1 to 10;
b is 1 to 10;
x is 1 to 10;
y is 1 to 10
z is 1 to 10 and
J is W, F, Y, L or M.

63. The construct according to clause 62, wherein the labile peptide linker comprises or more suitably consists of a polypeptide sequence of the format:

$$[-(G_4S)_x\text{-}J\text{-}(G_4S)_y-]_z$$

wherein
x is 1 to 10;
y is 1 to 10
z is 1 to 10 and
J is W, F, Y, L or M.

64. The construct according to clause 1, wherein the labile peptide linker comprises or more suitably consists of a polypeptide sequence of the format:

$$\text{-}J\text{-}(G_aS)_x\text{-}J'\text{-}$$

wherein
a is 1 to 10;
x is 1 to 10;
J is W, F, Y, L or M and
J' is W, F, Y, L or M.

65. The construct according to clause 1, wherein the labile peptide linker comprises or more suitably consists of a polypeptide sequence of the format:

$$\text{-}J\text{-}(G_aS)_x\text{-}J'\text{-}(G_bS)_y\text{-}J''\text{-}$$

wherein
a is 1 to 10;
b is 1 to 10;
x is 1 to 10;
y is 1 to 10;
J is W, F, Y, L or M
J' is W, F, Y, L or M and
J" is W, F, Y, L or M.

66. The construct according to any one of clauses 62 to 65, wherein a is 2 to 5.
67. The construct according to clause 66, wherein a is 4.
68. The construct according to any one of clauses 62 to 67, wherein b is 2 to 5.
69. The construct according to clause 68, wherein b is 4.
70. The construct according to any one of clauses 62 to 69, wherein x is 1 to 5.
71. The construct according to clause 70, wherein x is 2.
72. The construct according to clause 70, wherein x is 1.
73. The construct according to any one of clauses 62 to 72, wherein y is 1 to 5.
74. The construct according to clause 73, wherein y is 1.
75. The construct according to clause 73, wherein y is 2.
76. The construct according to any one of clauses 62 to 75, wherein z is 1 to 3.
77. The construct according to clause 76, wherein z is 1.
78. The construct according to any one of clauses 62 to 77, wherein J is W, F or Y.
79. The construct according to any one of clauses 62 to 78, wherein J' is W, F or Y.
80. The construct according to any one of clauses 62 to 79, wherein J" is W, F or Y.

The construct according to any one of clauses 1 to 80, wherein the first antibody or antigen binding fragment thereof binds to a first target accessible via the intestinal tract, such as a target within the intestinal tract.

82. The construct according to clause 81, wherein the first target is a first deleterious agent originating from an intestinal tract resident pathogenic microbe.
83. The construct according to clause 81, wherein the first target is selected from the group consisting of: TNF-alpha, *C. difficile* toxin A, *C. difficile* toxin B, CD3 or IL-6R.
84. The construct according to clause 83, wherein the first target is selected from the group consisting of: TNF-alpha or *C. difficile* toxin A.
85. The construct according to clause 81, wherein the second antibody or antigen binding fragment thereof binds to a second target accessible via the intestinal tract, such as a target within the intestinal tract.
86. The construct according to clause 85, wherein second target is a second deleterious agent originating from an intestinal tract resident pathogenic microbe.
87. The construct according to clause 85, wherein the second target is selected from the group consisting of: TNF-alpha, *C. difficile* toxin A, *C. difficile* toxin B, CD3 or IL-6R.
88. The construct according to clause 87, wherein the second target is selected from the group consisting of: TNF-alpha or *C. difficile* toxin A.
89. The construct according to any one of clauses 81 to 88, wherein the first and second targets are identical.
90. The construct according to any one of clauses 81 to 88, wherein the first and second targets are different.
91. The construct according to any one of clauses 1 to 90, wherein the antigen-binding fragments are selected from the group consisting of: VLs, V-NARs, scFvs, Fab fragments, F(ab')2 fragments or immunoglobulin chain variable domains such as VHHs and VHs.
92. The construct according to clause 91, wherein the antigen-binding fragments are VHHs.
93. The construct according to clause 91, wherein the antigen-binding fragments are VHs.
94. The construct according to any one of clauses 1 to 93, wherein at least 20%, such as at least 40%, such as at least 60%, such as at least 80%, such as at least 90%, such as at least 100% by mass of the construct remains uncleaved after at least 10, such as at least 20, such as at least 30 minutes after mixing in the Faecal Protease Assay and/or Trypsin Protease Assay and/or Chymotrypsin Protease Assay.
95. The construct according to clause 1, wherein the first and second polypeptides each comprise a sequence selected from the group consisting of SEQ ID NO: 18 and SEQ ID NO: 19.
96. The construct according to clause 95 wherein the first and second polypeptides each consist of a sequence selected from the group consisting of SEQ ID NO: 18 and SEQ ID NO: 19.
97. The construct according to clause 1 wherein the construct comprises a sequence selected from the group consisting of SEQ ID NOs: 7 to 17.
98. The construct according to clause 97 wherein the construct consists of a sequence selected from the group consisting of SEQ ID NOs: 7 to 17.

99. The construct according to clause 1 wherein the labile peptide linker comprises a sequence selected from the group consisting of SEQ ID NOs: 1 to 6.
100. The construct according to clause 99 wherein the labile peptide linker consists of a sequence selected from the group consisting of SEQ ID NOs: 1 to 6.
101. The construct according to any one of clauses 1 to 94, wherein the construct comprises an additional third polypeptide connected by a peptide linker to the first polypeptide, wherein the third polypeptide is substantially resistant to the one or more proteases present in the intestinal tract.
102. The construct according to clause 101, wherein the construct comprises or consists of an additional fourth polypeptide connected by a peptide linker to the second polypeptide, wherein the fourth polypeptide is substantially resistant to the one or more proteases present in the intestinal tract.
103. The construct according to clause 101 or 102, wherein the peptide linkers are substantially resistant to the one or more proteases present in the intestinal tract.
104. The construct according to clause 101 or 102, wherein the peptide linkers are labile peptide linkers.
105. The construct according to any one of clauses 1 to 104, wherein the construct is enterically-coated.
106. A pharmaceutical composition comprising a construct according to any one of clauses 1 to 105 and a pharmaceutically acceptable excipient.
107. The construct or composition according to any one of clauses 1 to 106 for use as a medicament.
108. The construct or composition according to clause 107 wherein the medicament is administered by oral administration.
109. The construct or composition according to clause 108 for use in the treatment of diseases of the GIT.
110. The construct or composition according to clause 109 for use in the treatment of autoimmune and/or inflammatory disease.
111. The construct or composition according to clause 110 for use in the treatment of inflammatory bowel disease such as Crohn's disease and/or ulcerative colitis.
112. The construct or composition according to clause 109 for use in the treatment of bacterial infection such as *C. difficile* infection.
113. A nucleic acid comprising a sequence encoding the construct according to any one of clauses 1 to 104.
114. A method of treating autoimmune disease comprising administering to a person in need thereof a therapeutically effective amount of a construct or composition according to any one of clauses 1 to 106.
115. A method of treating bacterial infection such as *C. difficile* infection comprising administering to a person in need thereof a therapeutically effective amount of a construct or composition according to any one of clauses 1 to 106.
116. A method of treating a disease with a monomeric polypeptide, comprising administering to a subject the construct or composition of any one of clauses 1 to 106.
117. A method of treating a disease with two or more monomeric polypeptides, comprising administering to a subject the construct or composition of any one of clauses 1 to 106.
118. A method of treating two or more diseases with two or more monomeric polypeptides, comprising administering to a subject the construct or composition of any one of clauses 1 to 106.
119. The method of any one of clauses 114 to 118 wherein the disease is an autoimmune disease and/or inflammatory disease or GIT infection.
120. A method of assaying the lability of a construct according to any one of clauses 1 to 104, comprising the steps of: (a) incubating the construct in a solution comprising trypsin, a solution comprising chymotrypsin, faecal supernatant, small intestinal fluid, or a solution comprising enteropeptidase, such as by performing the Trypsin Protease Assay of Example 1, the Chymotrypsin Protease Assay of Example 2 or the Faecal Protease Assay of Example 3, then (b) ascertaining the proportion of cleaved construct after one or more periods of incubation.
121. The method according to clause 120, wherein the level of lability is the percentage of the construct remaining uncleaved after at least 10, such as at least 20, such as at least 30 minutes after mixing in the Trypsin Protease Assay of Example 1, the Chymotrypsin Protease Assay of Example 2 or the Faecal Protease Assay of Example 3.
122. A method of delivering a monomeric antibody or a monomeric antigen binding fragment thereof to a targeted region of the intestinal tract, comprising the steps of: (a) performing the method according to either clauses 120 or 121 then (b) selecting a construct with an appropriate level of lability for the targeted region of the intestinal tract, (c) producing the selected construct with an enterically coated packaging then (d) administering the packaged selected construct to a subject.
123. A method of delivering a monomeric polypeptide to the intestinal tract, comprising administering to a subject the construct or composition of any one of clauses 1 to 106.
124. The method of any one of clauses 116 to 119 or 122 to 123 wherein the subject is a mammal such as a human.
125. A method of preparing a product comprising a construct according to any one of clauses 1 to 104 which has been selected, the method comprising adding the selected construct into the product, wherein the selected construct is selected and produced by a method comprising the steps of: (a) performing the method according to either clause 120 or 121 then (b) selecting a construct with an appropriate level of lability for the targeted region of the intestinal tract.
126. A polypeptide comprising SEQ ID NO: 1, SEQ ID NO: 2, SEQ ID NO: 3, SEQ ID NO: 4, SEQ ID NO: 5, SEQ ID NO: 6.
127. A polynucleotide comprising SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36.

Further Clauses

A set of further clauses defining the invention and its preferred aspects is as follows:
1. A construct suitable for oral administration comprising a first polypeptide and a second polypeptide connected by a labile peptide linker, wherein the labile peptide linker is labile to one or more proteases present in the intestinal tract and wherein the first and second polypeptides are substantially resistant to said one or more proteases.

2. The construct according to clause 1, wherein the first polypeptide is an antigen-binding polypeptide and the second polypeptide is an antigen-binding polypeptide.
3. The construct according to either clause 1 or 2 wherein the first and second polypeptides are substantially resistant to all proteases present in the intestinal tract.
4. The construct according to any one of clauses 1 to 3, wherein the labile peptide linker comprises at least 1, such as at least 2, such as at least 3, such as at least 4, such as at least 5, such as at least 6, such as at least 7, such as at least 8, such as at least 9, such as at least 10 K and/or R residues.
5. The construct according to any one of clauses 1 to 4, wherein all K or R residues comprised within the labile peptide linker have at least 1, such as at least 2, such as at least 3, such as at least 4, such as at least 5 shielding residues on their N-terminal and/or C-terminal side, wherein the shielding residues are selected from the list consisting of: D and E.
6. The construct according to any one of clauses 1 to 4, wherein all K or R residues comprised within the labile peptide linker have at least 1, such as at least 2, such as at least 3, such as at least 4, such as at least 5 non-shielding residues on their N-terminal and/or C-terminal side, wherein the non-shielding residues are selected from the list consisting of: C, A, S, N, G, L, I, V, T, M, F, Y, H, W and Q.
7. The construct according to clause 1, wherein the labile peptide linker comprises a polypeptide sequence of the format:

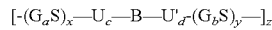

wherein
a is 1 to 10;
b is 1 to 10;
U is D or E;
U' is D or E;
c is 0 to 7;
d is 0 to 7;
x is 1 to 10;
y is 1 to 10
z is 1 to 10 and
B is K or R.
8. The construct according to clause 7, wherein c and d are both 0.
9. The construct according to clause 1, wherein the labile peptide linker comprises a polypeptide sequence of the format:

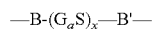

wherein
a is 1 to 10;
x is 1 to 10;
B is K or R and
B' is K or R.
10. The construct according to clause 1, wherein the labile peptide linker comprises a polypeptide sequence of the format:

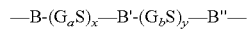

wherein
a is 1 to 10;
b is 1 to 10;
x is 1 to 10;
y is 1 to 10;
B is K or R;
B' is K or R and
B" is K or R.
11. The construct according to clause 1, wherein the labile peptide linker comprises a polypeptide sequence of the format:

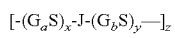

wherein
a is 1 to 10;
b is 1 to 10;
x is 1 to 10;
y is 1 to 10
z is 1 to 10 and
J is W, F, Y, L or M; such as W, F or Y.
12. The construct according to any one of clauses 7 to 11, wherein a is 4, b is 4 and z is 1.
13. The construct according to any one of clauses 1 to 12, wherein the antigen-binding fragments are selected from the group consisting of: VLs, V-NARs, scFvs, Fab fragments, F(ab')2 fragments or immunoglobulin chain variable domains such as VHHs and VHs.
14. A pharmaceutical composition comprising the construct according to any one of clauses 1 to 13 for use as a medicament for the treatment of diseases of the GIT administered by oral administration.
15. A polypeptide comprising SEQ ID NO: 1, SEQ ID NO: 2, SEQ ID NO: 3, SEQ ID NO: 4, SEQ ID NO: 5 or SEQ ID NO: 6.

The present invention will now be further described by means of the following non-limiting examples.

EXAMPLES

Example 1: The Trypsin Protease Assay

To test the lability of labile peptide linkers, the Trypsin Protease Assay was developed. This assay is performed as follows.

A buffered (10 mM acetic acid, pH 3.2, containing 0.01% thimerosal) aqueous suspension of L-1-tosylamido-2-phenylethyl chloromethyl ketone (TPCK)-treated Trypsin-agarose beads (trypsin from bovine pancreas; T4019; Sigma Aldrich) is used for the assay. The beads are washed 3 times with water (250 µl beads+1.25 ml water) followed by washing 5 times with Trypsin buffer (TRYP buffer; 1 mM Tris-HCl, 20 mM CaCl$_2$) [pH 8.0]). Finally, the resin is resuspended in TRYP buffer as a 50% (v/v) suspension.

100 µl of a 2 mg/ml construct solution is mixed with 225 µl 50% (v/v) immobilized TPCK-treated Trypsin in TRYP buffer. After time intervals such as 0, 10, 15, 30, 45 and 60 minutes of incubation at 37° C. in a shaker, samples are taken as follows: resin is pelleted by a 1 min centrifugation step at 500×g, and a 40 µl sample is taken from the supernatant and mixed with 2× sample loading buffer (such as Laemmli buffer). The remaining suspension is mixed again, and put back at 37° C. in the shaker.

For analysis, 15 µl of each sample is mixed with 5 µl 4× loading dye, boiled for 10 mins and 15 µl is loaded per lane on a polyacrylamide gel (such as NuPAGE 10% acrylamide Bis-Tris gel). Gels are run in SDS-MES buffer at 200 V for 35 mins. Gels are fixed in 40% methanol, 7% acetic acid for 30 mins and stained in colloidal Coomassie Brilliant Blue stain overnight. Gels are destained in water before imaging (such as using ImageQuant LAS4000 with 7 secs exposure). The quantity of intact constructs relative to cleaved constituent polypeptides can be assessed by comparing the corresponding bands in each time point lane.

Example 2: The Chymotrypsin Protease Assay

The Trypsin Protease Assay protocol can be used wherein Trypsin beads are substituted with Chymotrypsin beads.

Example 3: The Faecal Extract Protease Assay

To test the lability of labile peptide linkers, the Faecal Extract Protease Assay was developed. Faecal extract is a physiologically relevant matrix in particular for polypeptides targeted to the large intestine. This assay is performed as follows.

Human faecal samples from multiple individuals are turned into slurries with addition of 1×PBS at a ratio of 1, 2 or 3 mLs 1×PBS per gram of faeces. The slurries are then pooled (such that one pool represents the combined protease output from the faeces of multiple individuals), centrifuged and the supernatants removed, aliquoted and stored at −70 degrees C. This process removes the faecal matrix, including any cellular material. For digestion, constructs are incubated at a concentration of 160.16 µg/ml at 37° C. in pooled human faecal supernatant for 60 mins in the absence of BSA carrier. Aliquots are taken after time intervals such as 0, 10, 30 and 60 minutes and are mixed 1:1 in Protease Stop Solution (1×PBS+2× protease inhibitor cocktail (Sigma)+1% PMSF) and immediately frozen at −80° C.

For analysis, samples are defrosted and 15 µl of each sample is mixed with 5 µl 4× loading dye, boiled for 10 mins and 15 µl is loaded per lane on a polyacrylamide gel (such as NuPAGE 10% acrylamide Bis-Tris gel). Gels are run in SDS-MES buffer at 200 V for 35 mins. Gels are fixed in 40% methanol, 7% acetic acid for 30 mins and stained in colloidal Coomassie Brilliant Blue stain overnight. Gels were destained in water before imaging (such as using ImageQuant LAS4000 with 7 secs exposure). The quantity of intact constructs relative to cleaved constituent polypeptides can be assessed by comparing the corresponding higher and lower molecular weight bands in each time point lane.

Example 4: Production of Constructs

Homobihead constructs containing a range of different linker sequences linking either (a) two anti-TcdA (*Clostridium difficile* toxin A) ICVDs were expressed in *S. cerevisiae* and (b) two anti-TNF-alpha ICVDs were designed and expressed in *E. coli*. The anti-TcdA constructs were homobiheads of ICVD ID1A, separated by different linkers. The anti-TNF-alpha constructs were homobiheads of ICVD ID5F, encoded by polynucleotides which also included Flag-6His tags.

Anti-TcdA Constructs

Homobihead constructs ID3A, ID4A and ID25A to ID28A were expressed from *S. cerevisiae*. These constructs do not carry any protein tags at either terminus. ID25A to ID28A, containing the labile peptide linkers, were generated by overlap PCR using ID1A encoding DNA as a template and cloned into the SacI/HindIII sites of shuttle vector pUR4547 (BAC) capable of replication in *E. coli* and *S. cerevisiae*. Expression, and full secretion into the supernatant, from *S. cerevisiae* was achieved from the shuttle vector via galactose induction. Finally, the constructs were purified using Capto S cation exchange resin (GE) and dialysed into 1×PBS.

Expression in *S. cerevisiae* and subsequent storage was carried out according to the Yeast Expression Protocol as detailed above.

Anti-TNF-alpha Constructs

ID55F to ID60F were cloned directly into the SfiI/BsteII sites of vector pMEK222 (QVQ). ID55F to ID60F carry C-terminal Flag-6His tags. The resulting plasmids were transformed into *E. coli* BL21 DE3 (Novagen) for expression and transport to the periplasm. Following overnight growth in Autoinduction medium Terrific broth (Formedium), cells were pelleted, frozen at −80 degrees C. and re-suspended in 1/10 the original volume of 1×PBS to disrupt the outer membrane. ID55F to ID60F were purified from the supernatant by AKTA Prime FPLC using a Ni-NTA column to bind the His tags, followed by imidazole elution and dialysis into 1×PBS.

The sequences of the linkers are given in Table 1 below.

TABLE 1

| Construct Name | ICVD Target | Linker Sequence | Linker SEQ ID Number | Construct SEQ ID Number |
|---|---|---|---|---|
| ID3A | TcdA | GGGGSGGGGSGGGGSGGGGS | 1 | 7 |
| ID25A | TcdA | GGGGSKGGGGS | 2 | 8 |
| ID26A | TcdA | GGGGSDKDGGGGS | 3 | 9 |
| ID27A | TcdA | GGGGSDDDDKGGGGS | 4 | 10 |
| ID28A | TcdA | KGGGGSGGGGSK | 5 | 11 |
| ID4A | TcdA | RGGGGSRGGGGSR | 6 | 38 |
| ID55F | Human TNF-alpha | GGGGSGGGGSGGGGSGGGGS | 1 | 12 |
| ID57F | Human TNF-alpha | GGGGSKGGGGS | 2 | 13 |
| ID58F | Human TNF-alpha | GGGGSDKDGGGGS | 3 | 14 |

TABLE 1-continued

| Construct Name | ICVD Target | Linker Sequence | Linker SEQ ID Number | Construct SEQ ID Number |
|---|---|---|---|---|
| ID59F | Human TNF-alpha | GGGGSDDDDKGGGGS | 4 | 15 |
| ID60F | Human TNF-alpha | KGGGGSGGGGSK | 5 | 16 |
| ID56F | Human TNF-alpha | RGGGGSRGGGGSR | 6 | 17 |

Example 5: Assaying the Lability of Anti-TcdA Constructs Using the Trypsin Protease Assay The lability of the constructs of Example 4 targeting TcdA were assayed using The Trypsin Protease Assay described in Example 1. The results of the assay are shown in SDS-PAGE gels in FIGS. 1 to 3 wherein M=molecular weight marker; lane 1=ICVD before addition of trypsin beads, lane 2=0 min digestion, lane 3=10 min digestion, lane 4=25 min digestion, lane 5=60 min digestion, lane 6=105 min digestion and lane 7=160 min digestion with trypsin beads.

It can be seen that ID3A remained substantially intact over all time periods tested (FIG. 1). ID25A (FIG. 2) was completely cleaved very quickly after between 0 and 10 minutes of incubation. The shielding D residues in ID26A (FIG. 2) resulted in gradual cleavage of the linker from between 0 to 10 minutes to complete cleavage after 105 minutes. The labile residues situated at either terminus of the ID28A linker (FIG. 3) and the additional N-side shielding D residues in ID27A (FIG. 3) both resulted in slower cleavage, still ongoing after 160 minutes of incubation. The constructs in order of least to most labile were ID3A>ID28A>ID27A>ID26A>ID25A.

Figure 2:
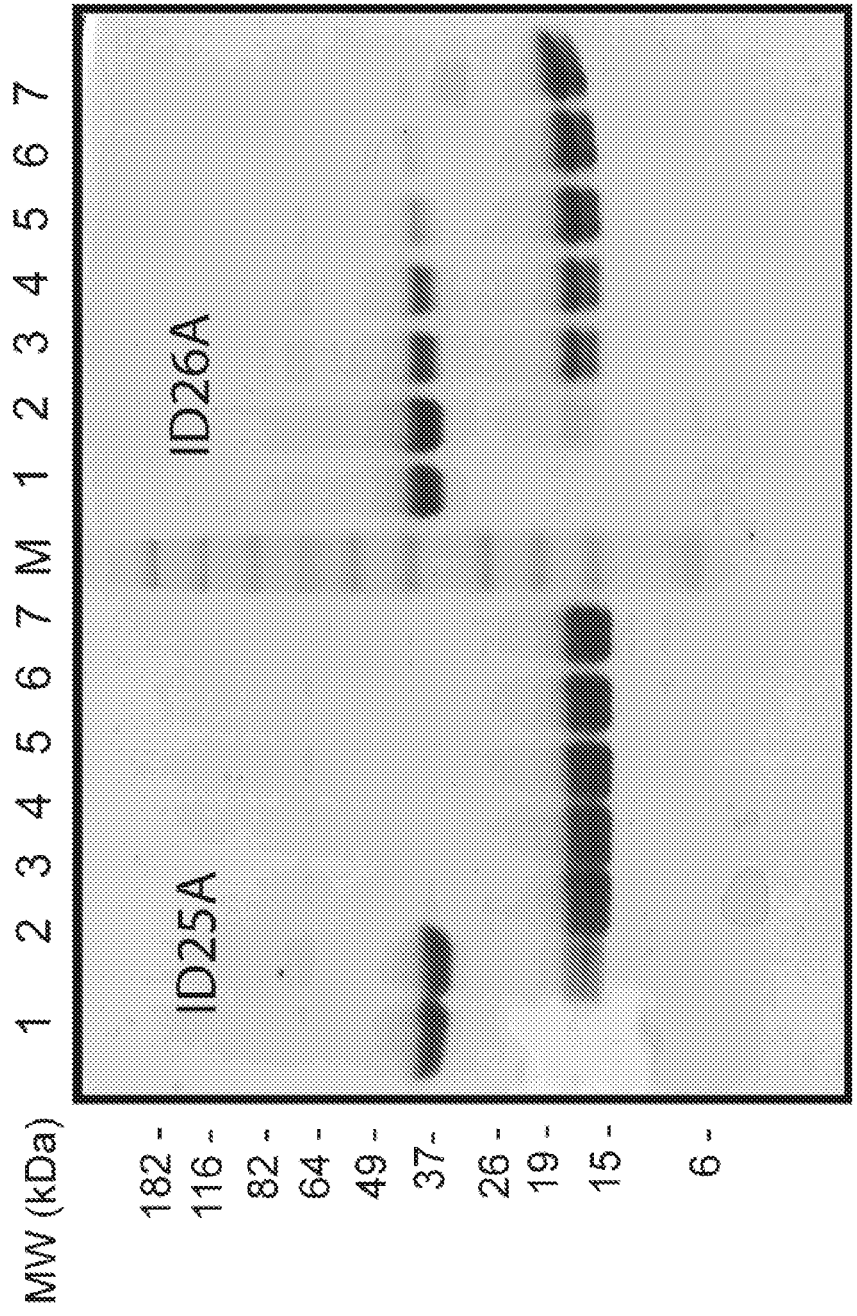
Figure 3:
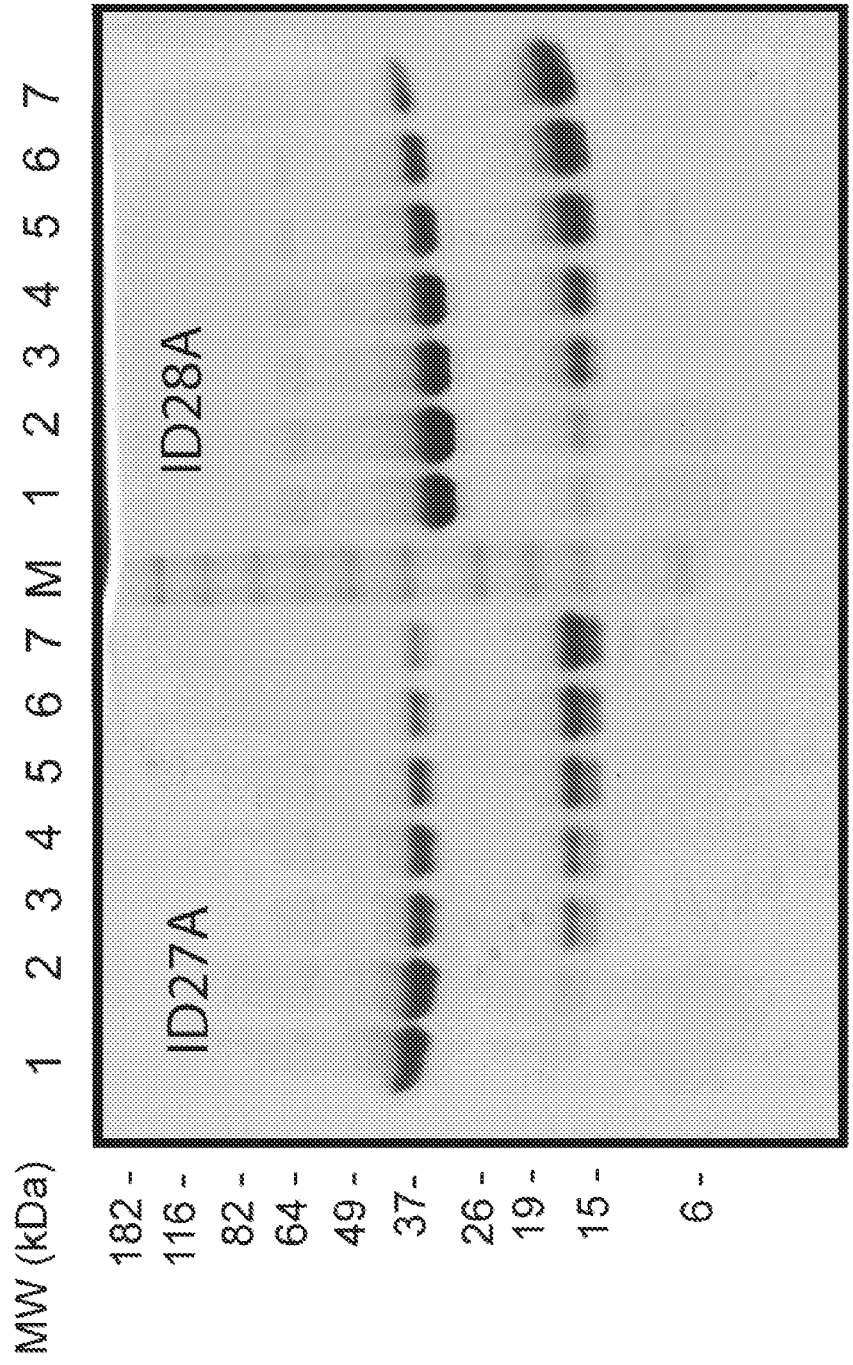

Uncleaved constructs running at molecular weights of approximately 35 kDa are visible in lanes corresponding to early time points (FIGS. 2 and 3). The cleaved constructs (i.e. constituent monomer ICVDs) are visible in lanes corresponding to later time points running at molecular weights of approximately 18 kDa. It is clear therefore from visual inspection of these gels that greater than 50% by mass of constructs ID25A, ID26A, ID27A and ID28A was cleaved into first and second immunoglobulin chain variable domains after 160 minutes (or earlier in some instances) after mixing in the Trypsin Protease Assay (lane 7). These are constructs of the invention comprising labile peptide linkers.

It is also clear from visual inspection of the gel in FIG. 1 that the only significant bands visible are those corresponding to the intact ID3A construct (running at a molecular weight of approximately 37 kDa). Therefore, ID3A was not cleaved into first and second immunoglobulin chain variable domains at any time point including after 160 minutes (lane 7) after mixing in the Trypsin Protease Assay. ID3A does not comprise a labile peptide linker and is not a construct according to the invention.

Furthermore, it is clear from visual inspection of the gels in FIGS. 2 and 3 that the first immunoglobulin chain variable domain and the second immunoglobulin chain variable domain in these constructs are themselves substantially resistant to one or more proteases present in the intestinal tract. It can be seen that there are no significant bands visible which correspond to fragments of ICVD monomers (the intact monomers running at a molecular weight of approximately 18 kDa) and thus at least 70% by mass of the immunoglobulin chain variable domains have clearly remained uncleaved after all time points tested including 160 minutes after mixing in the Trypsin Protease Assay.

Example 6: Assaying the Lability of Anti-TcdA and Anti-TNF-Alpha Constructs Using the Faecal Protease Assay The lability of the constructs of Example 4 targeting TcdA and targeting TNF-alpha were assayed using The Faecal Protease Assay described in Example 3. The results of the assay are shown in SDS-PAGE gels in FIG. 4 (anti-TcdA constructs) and FIG. 5 (anti-TNF-alpha constructs). Lanes are labelled according to the construct tested and the period of incubation in minutes. 'X' indicates lane containing no ICVD (only faecal extract). In FIG. 5, 'B' indicates bihead and 'M' indicates cleaved monomers.

Anti-TcdA Constructs

Figure 4:
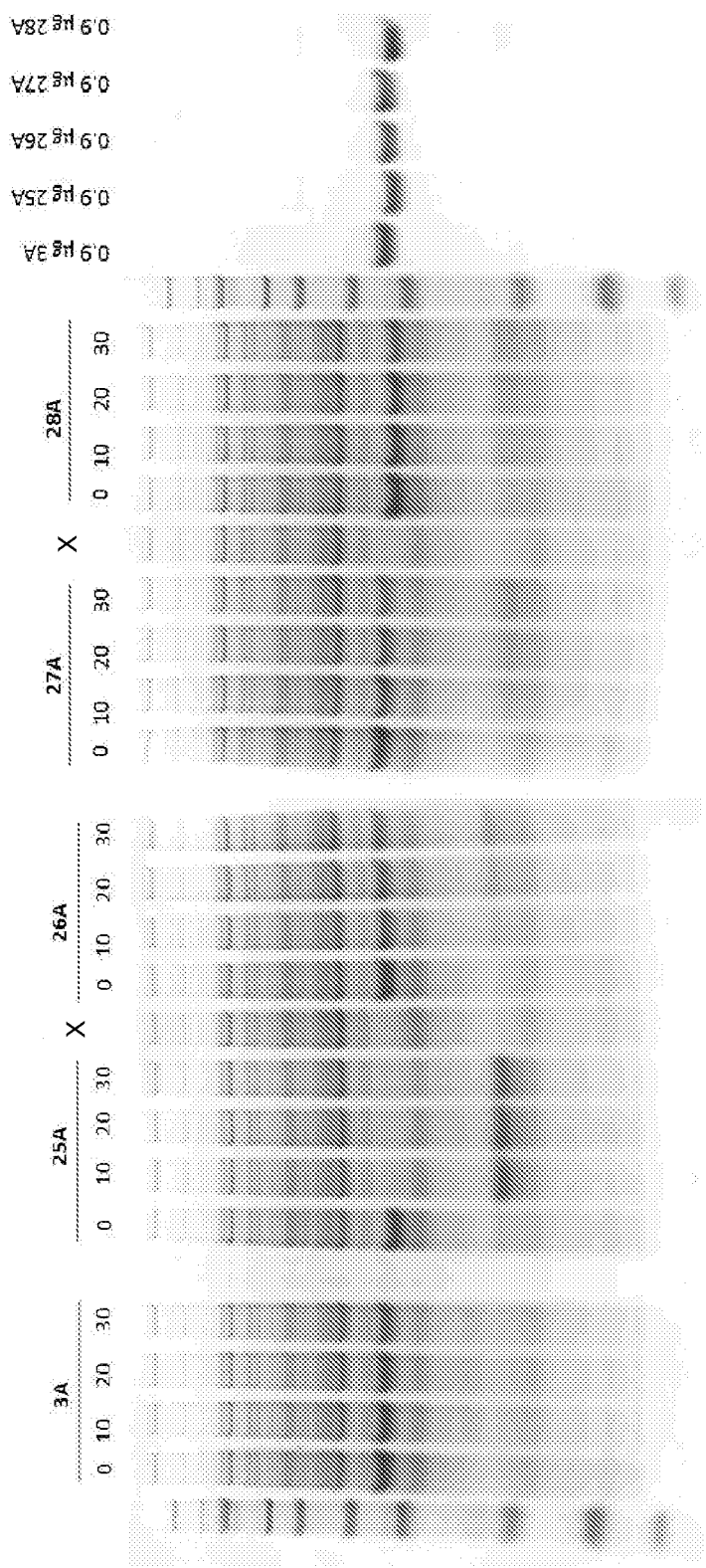
Figure 5:
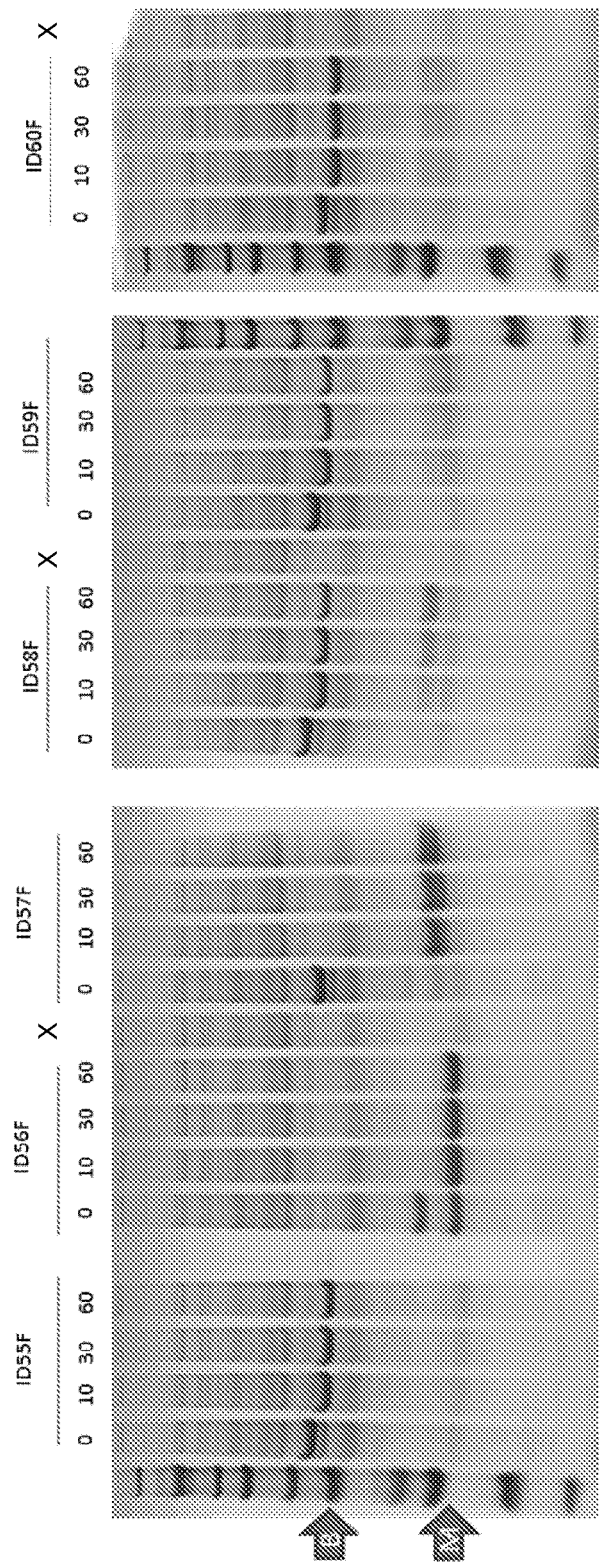

It can be seen from FIG. 4 that ID3A remained substantially intact over all time periods tested. ID25A was completely cleaved very quickly after between 0 and 10 minutes of incubation. The shielding D residues in ID26A, the additional N-side shielding D residues in ID27A and the labile residues situated at either terminus of the ID28A linker all resulted in slower cleavage relative to ID25A. Digestion of ID26A, ID27A and ID28A was still ongoing after 30 minutes of incubation.

Anti-TNF-Alpha Constructs

It can be seen from FIG. 5 that ID55F remained substantially intact over all time periods tested. ID56F underwent instant total cleavage. ID57F was completely cleaved very quickly after between 0 and 10 minutes of incubation. The shielding D residues in ID58F, the labile residues situated at either terminus of the ID60F linker and the additional N-side shielding D restudies in ID59F all resulted in slower cleavage relative to ID57F. Digestion of ID58F, ID59F and ID60F was still ongoing after 60 minutes of incubation.

Faecal Protease Assay Summary

It is apparent that lysine residues in the central region (but not peripheral regions) of the labile peptide linker increase lability to faecal proteases. Lability is reduced by shielding the lysine residues using flanking aspartate residues. The lability of the tested constructs in the Faecal Protease Assay is summarised in Tables 2 and 3 below.

TABLE 2

| Anti-TcdA Construct Name | Linker Sequence | Lability | Linker SEQ ID Number |
|---|---|---|---|
| ID3A | GGGGSGGGGSGGGGSGGGGS | Substantially no cleavage | 1 |
| ID28A | KGGGGSGGGGSK | Minor cleavage | 5 |
| ID26A | GGGGSDKDGGGGS | Some cleavage | 3 |
| ID27A | GGGGSDDDDKGGGGS | Substantial cleavage | 4 |
| ID25A | GGGGSKGGGGS | Total cleavage | 2 |

TABLE 3

| Anti-TNF-alpha Construct Name | Linker Sequence | Lability | Linker SEQ ID Number |
|---|---|---|---|
| ID55F | GGGGGGGGSGGGGSGGGGS | Substantially no cleavage | 1 |
| ID59F | GGGGSDDDDKGGGGS | Minimal cleavage | 4 |
| ID60F | KGGGGSGGGGSK | Minor cleavage | 5 |
| ID58F | GGGGSDKDGGGGS | Some cleavage | 3 |
| ID57F | GGGGSKGGGGS | Total cleavage | 2 |
| ID56F | RGGGGSRGGGGSR | Instant cleavage | 6 |

Example 7: Stability of Anti-TcdA Constructs During Storage

The anti-TcdA constructs (ID3A, ID25A, ID25A, ID27A and ID28A) were tested for their stability over time during storage. Samples were taken after 0, 2, 4 or 9 days of refrigeration at 4° C. (FIGS. 6 and 7). It can be seen that the SDS-PAGE gels contain bands corresponding to uncleaved bihead constructs and do not contain bands for cleaved monomers. Accordingly, the constructs are stable for at least 9 days under these conditions.

These uncleaved constructs ran with a molecular weight of approximately 35 kDa and constituent monomers would be expected to have an approximate molecular weight of 18 kDa. It is clear from visual inspection of the gels in FIGS. 6 and 7 that no significant bands are visible at a lower molecular weight than the 35 kDa bands corresponding to the intact constructs themselves and thus clearly no more than 10% by mass of these constructs is cleaved into first and second immunoglobulin chain variable domains after producing the constructs using the Yeast Expression Protocol (with 0 days storage) and also after a storage period of 2, 4 or 9 days.

Furthermore, it is clear that the constituent immunoglobulin chain variable domains are substantially resistant to yeast proteases because no significant bands running at a lower molecular weight than that of a single ICVD monomer (running at approximately 18 kDa) are visible in FIG. 6 or 7. Accordingly, it is clear that no more than 10% by mass of the first or second immunoglobulin chain variable domain is cleaved after producing the first or second immunoglobulin chain variable domain using the Yeast Expression Protocol (with 0 days storage) and also after a storage period of 2, 4 or 9 days.

Example 8: Production of Constructs Incorporating Chymotrypsin-Labile Linkers Homobihead or heterobihead constructs containing a range of different linker sequences containing chymotrypsin-labile sites (W, F, Y, L or M; particularly W, F or Y) may be designed and expressed in a suitable host such as *S. cerevisiae*, using the methods analogous to those detailed in Example 4 above. A suitable construct is provided in Table 4.

TABLE 4

| ICVD Target | Linker Sequence | Linker SEQ ID Number |
|---|---|---|
| TcdA | GGGGSYGGGGS | 37 |

The lability of such constructs is then assayed using the Chymotrypsin Protease Assay and the Faecal Protease Assay.

Example 9: Testing the Stability of ID4A During Production and Storage

Anti-TcdA construct ID4A was expressed in *S. cerevisiae* using The Yeast Expression Protocol. ID4A is a homobihead of ICVD ID1A and does not carry any protein tag at either terminus. The sequence of the linker is given in Table 1 above.

ID4A was tested for its stability over time during production and storage. Samples were taken after 0, 2, 4 or 9 days of refrigeration at 4° C. (FIG. 8). It can be seen that every lane of the SDS-PAGE gel contains bands corresponding to cleaved monomers, all running at an approximate molecular weight of 10 kDa and no lane clearly contains a band corresponding to uncleaved bihead. It appears that the linker used in ID4A was cleaved by yeast proteases during production.

It is therefore clear from visual inspection of the gel in FIG. 8 that more than 10% (in fact, 100%) by mass of ID4A is cleaved into first and second immunoglobulin chain variable domains after producing the construct using the Yeast Expression Protocol (with 0 days storage). Constructs of the invention are stable to yeast proteases and therefore ID4A is not a construct of the invention.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications mentioned throughout the specification of the present invention are herein incorporated in their entirety by reference. The invention embraces all combinations of preferred and more preferred groups and suitable and more suitable groups and embodiments of groups recited above.

```
                        SEQUENCE LISTING

<160> NUMBER OF SEQ ID NOS: 42

<210> SEQ ID NO 1
<211> LENGTH: 20
<212> TYPE: PRT
<213> ORGANISM: Artificial Sequence
<220> FEATURE:
<223> OTHER INFORMATION: Polypeptide sequence of linker used in
      constructs ID3A and ID55F

<400> SEQUENCE: 1

Gly Gly Gly Gly Ser Gly Gly Gly Gly Ser Gly Gly Gly Gly Ser Gly
1               5                   10                  15

Gly Gly Gly Ser
            20

<210> SEQ ID NO 2
<211> LENGTH: 11
<212> TYPE: PRT
<213> ORGANISM: Artificial Sequence
<220> FEATURE:
<223> OTHER INFORMATION: Polypeptide sequence of linker used in
      constructs ID25A and ID57F

<400> SEQUENCE: 2

Gly Gly Gly Gly Ser Lys Gly Gly Gly Gly Ser
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Polypeptide sequence of linker used in
      constructs ID26A and ID58F

<400> SEQUENCE: 3

Gly Gly Gly Gly Ser Asp Lys Asp Gly Gly Gly Gly Ser
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Polypeptide sequence of linker used in
      constructs ID27A and ID59F

<400> SEQUENCE: 4

Gly Gly Gly Gly Ser Asp Asp Asp Asp Lys Gly Gly Gly Gly Ser
1               5                   10                  15
```

```
<210> SEQ ID NO 5
<211> LENGTH: 12
<212> TYPE: PRT
<213> ORGANISM: Artificial Sequence
<220> FEATURE:
<223> OTHER INFORMATION: Polypeptide sequence of linker used in
      constructs ID28A and ID60F

<400> SEQUENCE: 5

Lys Gly Gly Gly Gly Ser Gly Gly Gly Gly Ser Lys
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Polypeptide sequence of linker used in
      construct ID56F

<400> SEQUENCE: 6

Arg Gly Gly Gly Gly Ser Arg Gly Gly Gly Gly Ser Arg
1               5                   10

<210> SEQ ID NO 7
<211> LENGTH: 242
<212> TYPE: PRT
<213> ORGANISM: Artificial Sequence
<220> FEATURE:
<223> OTHER INFORMATION: Polypeptide sequence of ID3A construct

<400> SEQUENCE: 7

Asp Val Gln Leu Gln Glu Ser Gly Gly Gly Leu Val Gln Pro Gly Gly
1               5                   10                  15

Ser Leu Arg Leu Ser Cys Val Ile Ser Gly Met Asp Phe Ser His Lys
            20                  25                  30

Pro Ala Gly Trp Phe Arg Gln Ala Pro Gly Lys Glu Arg Glu Phe Val
        35                  40                  45

Ala Ser Ile Thr Thr Arg Ala Ser Thr His Tyr Ala Asp Ser Val Lys
    50                  55                  60

Gly Arg Phe Thr Ile Ser Arg Asp Asn Ala Lys Asn Thr Val Tyr Leu
65                  70                  75                  80

Glu Met Asn Ser Leu Lys Pro Glu Asp Thr Ala Val Tyr Ser Cys Asn
                85                  90                  95

Ser Glu Tyr Tyr Trp Gly Gln Gly Thr Gln Val Thr Val Ser Ser Gly
            100                 105                 110

Gly Gly Gly Ser Gly Gly Gly Gly Ser Gly Gly Gly Ser Gly Gly
        115                 120                 125

Gly Gly Ser Asp Val Gln Leu Gln Glu Ser Gly Gly Gly Leu Val Gln
    130                 135                 140

Pro Gly Gly Ser Leu Arg Leu Ser Cys Val Ile Ser Gly Met Asp Phe
145                 150                 155                 160

Ser His Lys Pro Ala Gly Trp Phe Arg Gln Ala Pro Gly Lys Glu Arg
                165                 170                 175

Glu Phe Val Ala Ser Ile Thr Thr Arg Ala Ser Thr His Tyr Ala Asp
            180                 185                 190

Ser Val Lys Gly Arg Phe Thr Ile Ser Arg Asp Asn Ala Lys Asn Thr
        195                 200                 205

Val Tyr Leu Glu Met Asn Ser Leu Lys Pro Glu Asp Thr Ala Val Tyr
    210                 215                 220
```

Ser Cys Asn Ser Glu Tyr Tyr Trp Gly Gln Gly Thr Gln Val Thr Val
225                 230                 235                 240

Ser Ser

<210> SEQ ID NO 8
<211> LENGTH: 233
<212> TYPE: PRT
<213> ORGANISM: Artificial Sequence
<220> FEATURE:
<223> OTHER INFORMATION: Polypeptide sequence of ID25A construct

<400> SEQUENCE: 8

Asp Val Gln Leu Gln Glu Ser Gly Gly Gly Leu Val Gln Pro Gly Gly
1               5                   10                  15

Ser Leu Arg Leu Ser Cys Val Ile Ser Gly Met Asp Phe Ser His Lys
            20                  25                  30

Pro Ala Gly Trp Phe Arg Gln Ala Pro Gly Lys Glu Arg Glu Phe Val
        35                  40                  45

Ala Ser Ile Thr Thr Arg Ala Ser Thr His Tyr Ala Asp Ser Val Lys
    50                  55                  60

Gly Arg Phe Thr Ile Ser Arg Asp Asn Ala Lys Asn Thr Val Tyr Leu
65                  70                  75                  80

Glu Met Asn Ser Leu Lys Pro Glu Asp Thr Ala Val Tyr Ser Cys Asn
                85                  90                  95

Ser Glu Tyr Tyr Trp Gly Gln Gly Thr Gln Val Thr Val Ser Ser Gly
            100                 105                 110

Gly Gly Gly Ser Lys Gly Gly Gly Ser Asp Val Gln Leu Gln Glu
        115                 120                 125

Ser Gly Gly Gly Leu Val Gln Pro Gly Gly Ser Leu Arg Leu Ser Cys
130                 135                 140

Val Ile Ser Gly Met Asp Phe Ser His Lys Pro Ala Gly Trp Phe Arg
145                 150                 155                 160

Gln Ala Pro Gly Lys Glu Arg Glu Phe Val Ala Ser Ile Thr Thr Arg
                165                 170                 175

Ala Ser Thr His Tyr Ala Asp Ser Val Lys Gly Arg Phe Thr Ile Ser
            180                 185                 190

Arg Asp Asn Ala Lys Asn Thr Val Tyr Leu Glu Met Asn Ser Leu Lys
        195                 200                 205

Pro Glu Asp Thr Ala Val Tyr Ser Cys Asn Ser Glu Tyr Tyr Trp Gly
    210                 215                 220

Gln Gly Thr Gln Val Thr Val Ser Ser
225                 230

<210> SEQ ID NO 9
<211> LENGTH: 235
<212> TYPE: PRT
<213> ORGANISM: Artificial Sequence
<220> FEATURE:
<223> OTHER INFORMATION: Polypeptide sequence of ID26A construct

<400> SEQUENCE: 9

Asp Val Gln Leu Gln Glu Ser Gly Gly Gly Leu Val Gln Pro Gly Gly
1               5                   10                  15

Ser Leu Arg Leu Ser Cys Val Ile Ser Gly Met Asp Phe Ser His Lys
            20                  25                  30

Pro Ala Gly Trp Phe Arg Gln Ala Pro Gly Lys Glu Arg Glu Phe Val
        35                  40                  45

Ala Ser Ile Thr Thr Arg Ala Ser Thr His Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Glu Met Asn Ser Leu Lys Pro Glu Asp Thr Ala Val Tyr Ser Cys Asn
                 85                  90                  95

Ser Glu Tyr Tyr Trp Gly Gln Gly Thr Gln Val Thr Val Ser Ser Gly
             100                 105                 110

Gly Gly Gly Ser Asp Lys Asp Gly Gly Gly Ser Asp Val Gln Leu
         115                 120                 125

Gln Glu Ser Gly Gly Gly Leu Val Gln Pro Gly Gly Ser Leu Arg Leu
130                 135                 140

Ser Cys Val Ile Ser Gly Met Asp Phe Ser His Lys Pro Ala Gly Trp
145                 150                 155                 160

Phe Arg Gln Ala Pro Gly Lys Glu Arg Glu Phe Val Ala Ser Ile Thr
                165                 170                 175

Thr Arg Ala Ser Thr His Tyr Ala Asp Ser Val Lys Gly Arg Phe Thr
            180                 185                 190

Ile Ser Arg Asp Asn Ala Lys Asn Thr Val Tyr Leu Glu Met Asn Ser
        195                 200                 205

Leu Lys Pro Glu Asp Thr Ala Val Tyr Ser Cys Asn Ser Glu Tyr Tyr
210                 215                 220

Trp Gly Gln Gly Thr Gln Val Thr Val Ser Ser
225                 230                 235

<210> SEQ ID NO 10
<211> LENGTH: 237
<212> TYPE: PRT
<213> ORGANISM: Artificial Sequence
<220> FEATURE:
<223> OTHER INFORMATION: Polypeptide sequence of ID27A construct

<400> SEQUENCE: 10

Asp Val Gln Leu Gln Glu Ser Gly Gly Gly Leu Val Gln Pro Gly Gly
1               5                   10                  15

Ser Leu Arg Leu Ser Cys Val Ile Ser Gly Met Asp Phe Ser His Lys
             20                  25                  30

Pro Ala Gly Trp Phe Arg Gln Ala Pro Gly Lys Glu Arg Glu Phe Val
         35                  40                  45

Ala Ser Ile Thr Thr Arg Ala Ser Thr His Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Glu Met Asn Ser Leu Lys Pro Glu Asp Thr Ala Val Tyr Ser Cys Asn
                 85                  90                  95

Ser Glu Tyr Tyr Trp Gly Gln Gly Thr Gln Val Thr Val Ser Ser Gly
             100                 105                 110

Gly Gly Gly Ser Asp Asp Asp Lys Gly Gly Gly Ser Asp Val
         115                 120                 125

Gln Leu Gln Glu Ser Gly Gly Gly Leu Val Gln Pro Gly Gly Ser Leu
130                 135                 140

Arg Leu Ser Cys Val Ile Ser Gly Met Asp Phe Ser His Lys Pro Ala
145                 150                 155                 160

Gly Trp Phe Arg Gln Ala Pro Gly Lys Glu Arg Glu Phe Val Ala Ser
                165                 170                 175

```
Ile Thr Thr Arg Ala Ser Thr His Tyr Ala Asp Ser Val Lys Gly Arg
            180                 185                 190

Phe Thr Ile Ser Arg Asp Asn Ala Lys Asn Thr Val Tyr Leu Glu Met
            195                 200                 205

Asn Ser Leu Lys Pro Glu Asp Thr Ala Val Tyr Ser Cys Asn Ser Glu
            210                 215                 220

Tyr Tyr Trp Gly Gln Gly Thr Gln Val Thr Val Ser Ser
225                 230                 235

<210> SEQ ID NO 11
<211> LENGTH: 234
<212> TYPE: PRT
<213> ORGANISM: Artificial Sequence
<220> FEATURE:
<223> OTHER INFORMATION: Polypeptide sequence of ID28A construct

<400> SEQUENCE: 11

Asp Val Gln Leu Gln Glu Ser Gly Gly Gly Leu Val Gln Pro Gly Gly
1               5                   10                  15

Ser Leu Arg Leu Ser Cys Val Ile Ser Gly Met Asp Phe Ser His Lys
            20                  25                  30

Pro Ala Gly Trp Phe Arg Gln Ala Pro Gly Lys Glu Arg Glu Phe Val
            35                  40                  45

Ala Ser Ile Thr Thr Arg Ala Ser Thr His Tyr Ala Asp Ser Val Lys
    50                  55                  60

Gly Arg Phe Thr Ile Ser Arg Asp Asn Ala Lys Asn Thr Val Tyr Leu
65                  70                  75                  80

Glu Met Asn Ser Leu Lys Pro Glu Asp Thr Ala Val Tyr Ser Cys Asn
                85                  90                  95

Ser Glu Tyr Tyr Trp Gly Gln Gly Thr Gln Val Thr Val Ser Ser Lys
            100                 105                 110

Gly Gly Gly Gly Ser Gly Gly Gly Ser Lys Asp Val Gln Leu Gln
            115                 120                 125

Glu Ser Gly Gly Gly Leu Val Gln Pro Gly Gly Ser Leu Arg Leu Ser
    130                 135                 140

Cys Val Ile Ser Gly Met Asp Phe Ser His Lys Pro Ala Gly Trp Phe
145                 150                 155                 160

Arg Gln Ala Pro Gly Lys Glu Arg Glu Phe Val Ala Ser Ile Thr Thr
                165                 170                 175

Arg Ala Ser Thr His Tyr Ala Asp Ser Val Lys Gly Arg Phe Thr Ile
            180                 185                 190

Ser Arg Asp Asn Ala Lys Asn Thr Val Tyr Leu Glu Met Asn Ser Leu
            195                 200                 205

Lys Pro Glu Asp Thr Ala Val Tyr Ser Cys Asn Ser Glu Tyr Tyr Trp
            210                 215                 220

Gly Gln Gly Thr Gln Val Thr Val Ser Ser
225                 230

<210> SEQ ID NO 12
<211> LENGTH: 268
<212> TYPE: PRT
<213> ORGANISM: Artificial Sequence
<220> FEATURE:
<223> OTHER INFORMATION: Polypeptide sequence of ID55F construct

<400> SEQUENCE: 12

Glu Val Gln Leu Val Glu Ser Gly Gly Gly Leu Val Glu Ser Gly Ala
```

```
            1               5                  10                 15
        Ser Leu Arg Leu Ser Cys Val Thr Ser Gly His Ile Phe Lys Leu Tyr
                    20                  25                  30
        Gly Met Gly Trp Phe Arg Gln Ala Pro Gly Lys Asp Arg Glu Phe Val
                    35                  40                  45
        Ala Ala Val Thr Trp Asn Gly Pro Ser Thr Glu Tyr Ala Asp Ser Val
                    50                  55                  60
        Lys Gly Arg Phe Thr Ile Ser Lys Asp Asn Asp Arg Asn Thr Leu Tyr
        65                  70                  75                  80
        Leu Gln Met Asn Ser Leu Lys Pro Glu Asp Thr Ala Val Tyr Tyr Cys
                            85                  90                  95
        Ala Arg Ser Ser Ile Met Gly Ile Tyr Thr Thr Pro Asp Arg Tyr Glu
                            100                 105                 110
        Tyr Trp Gly Gln Gly Thr Gln Val Thr Val Ser Ser Gly Gly Gly Gly
                    115                 120                 125
        Ser Gly Gly Gly Gly Ser Gly Gly Gly Ser Gly Gly Gly Gly Ser
                    130                 135                 140
        Glu Val Gln Leu Val Glu Ser Gly Gly Gly Leu Val Glu Ser Gly Ala
        145                 150                 155                 160
        Ser Leu Arg Leu Ser Cys Val Thr Ser Gly His Ile Phe Lys Leu Tyr
                            165                 170                 175
        Gly Met Gly Trp Phe Arg Gln Ala Pro Gly Lys Asp Arg Glu Phe Val
                            180                 185                 190
        Ala Ala Val Thr Trp Asn Gly Pro Ser Thr Glu Tyr Ala Asp Ser Val
                            195                 200                 205
        Lys Gly Arg Phe Thr Ile Ser Lys Asp Asn Asp Arg Asn Thr Leu Tyr
                    210                 215                 220
        Leu Gln Met Asn Ser Leu Lys Pro Glu Asp Thr Ala Val Tyr Tyr Cys
        225                 230                 235                 240
        Ala Arg Ser Ser Ile Met Gly Ile Tyr Thr Thr Pro Asp Arg Tyr Glu
                            245                 250                 255
        Tyr Trp Gly Gln Gly Thr Gln Val Thr Val Ser Ser
                    260                 265

<210> SEQ ID NO 13
<211> LENGTH: 259
<212> TYPE: PRT
<213> ORGANISM: Artificial Sequence
<220> FEATURE:
<223> OTHER INFORMATION: Polypeptide sequence of ID57F construct

<400> SEQUENCE: 13

Glu Val Gln Leu Val Glu Ser Gly Gly Gly Leu Val Glu Ser Gly Ala
        1               5                   10                  15
        Ser Leu Arg Leu Ser Cys Val Thr Ser Gly His Ile Phe Lys Leu Tyr
                            20                  25                  30
        Gly Met Gly Trp Phe Arg Gln Ala Pro Gly Lys Asp Arg Glu Phe Val
                            35                  40                  45
        Ala Ala Val Thr Trp Asn Gly Pro Ser Thr Glu Tyr Ala Asp Ser Val
                    50                  55                  60
        Lys Gly Arg Phe Thr Ile Ser Lys Asp Asn Asp Arg Asn Thr Leu Tyr
        65                  70                  75                  80
        Leu Gln Met Asn Ser Leu Lys Pro Glu Asp Thr Ala Val Tyr Tyr Cys
                            85                  90                  95
        Ala Arg Ser Ser Ile Met Gly Ile Tyr Thr Thr Pro Asp Arg Tyr Glu
```

```
                100                 105                 110
Tyr Trp Gly Gln Gly Thr Gln Val Thr Val Ser Ser Gly Gly Gly
            115                 120                 125
Ser Lys Gly Gly Gly Ser Glu Val Gln Leu Val Glu Ser Gly Gly
            130                 135                 140
Gly Leu Val Glu Ser Gly Ala Ser Leu Arg Leu Ser Cys Val Thr Ser
145                 150                 155                 160
Gly His Ile Phe Lys Leu Tyr Gly Met Gly Trp Phe Arg Gln Ala Pro
                165                 170                 175
Gly Lys Asp Arg Glu Phe Val Ala Ala Val Thr Trp Asn Gly Pro Ser
                180                 185                 190
Thr Glu Tyr Ala Asp Ser Val Lys Gly Arg Phe Thr Ile Ser Lys Asp
                195                 200                 205
Asn Asp Arg Asn Thr Leu Tyr Leu Gln Met Asn Ser Leu Lys Pro Glu
                210                 215                 220
Asp Thr Ala Val Tyr Tyr Cys Ala Arg Ser Ser Ile Met Gly Ile Tyr
225                 230                 235                 240
Thr Thr Pro Asp Arg Tyr Glu Tyr Trp Gly Gln Gly Thr Gln Val Thr
                245                 250                 255
Val Ser Ser

<210> SEQ ID NO 14
<211> LENGTH: 261
<212> TYPE: PRT
<213> ORGANISM: Artificial Sequence
<220> FEATURE:
<223> OTHER INFORMATION: Polypeptide sequence of ID58F construct

<400> SEQUENCE: 14

Glu Val Gln Leu Val Glu Ser Gly Gly Gly Leu Val Glu Ser Gly Ala
1               5                   10                  15
Ser Leu Arg Leu Ser Cys Val Thr Ser Gly His Ile Phe Lys Leu Tyr
                20                  25                  30
Gly Met Gly Trp Phe Arg Gln Ala Pro Gly Lys Asp Arg Glu Phe Val
            35                  40                  45
Ala Ala Val Thr Trp Asn Gly Pro Ser Thr Glu Tyr Ala Asp Ser Val
        50                  55                  60
Lys Gly Arg Phe Thr Ile Ser Lys Asp Asn Asp Arg Asn Thr Leu Tyr
65                  70                  75                  80
Leu Gln Met Asn Ser Leu Lys Pro Glu Asp Thr Ala Val Tyr Tyr Cys
                85                  90                  95
Ala Arg Ser Ser Ile Met Gly Ile Tyr Thr Thr Pro Asp Arg Tyr Glu
                100                 105                 110
Tyr Trp Gly Gln Gly Thr Gln Val Thr Val Ser Ser Gly Gly Gly
            115                 120                 125
Ser Asp Lys Asp Gly Gly Gly Ser Glu Val Gln Leu Val Glu Ser
            130                 135                 140
Gly Gly Gly Leu Val Glu Ser Gly Ala Ser Leu Arg Leu Ser Cys Val
145                 150                 155                 160
Thr Ser Gly His Ile Phe Lys Leu Tyr Gly Met Gly Trp Phe Arg Gln
                165                 170                 175
Ala Pro Gly Lys Asp Arg Glu Phe Val Ala Ala Val Thr Trp Asn Gly
                180                 185                 190
Pro Ser Thr Glu Tyr Ala Asp Ser Val Lys Gly Arg Phe Thr Ile Ser
                195                 200                 205
```

```
Lys Asp Asn Asp Arg Asn Thr Leu Tyr Leu Gln Met Asn Ser Leu Lys
    210                 215                 220

Pro Glu Asp Thr Ala Val Tyr Tyr Cys Ala Arg Ser Ser Ile Met Gly
225                 230                 235                 240

Ile Tyr Thr Thr Pro Asp Arg Tyr Glu Tyr Trp Gly Gln Gly Thr Gln
                245                 250                 255

Val Thr Val Ser Ser
            260

<210> SEQ ID NO 15
<211> LENGTH: 263
<212> TYPE: PRT
<213> ORGANISM: Artificial Sequence
<220> FEATURE:
<223> OTHER INFORMATION: Polypeptide sequence of ID59F construct

<400> SEQUENCE: 15

Glu Val Gln Leu Val Glu Ser Gly Gly Gly Leu Val Glu Ser Gly Ala
1               5                   10                  15

Ser Leu Arg Leu Ser Cys Val Thr Ser Gly His Ile Phe Lys Leu Tyr
            20                  25                  30

Gly Met Gly Trp Phe Arg Gln Ala Pro Gly Lys Asp Arg Glu Phe Val
        35                  40                  45

Ala Ala Val Thr Trp Asn Gly Pro Ser Thr Glu Tyr Ala Asp Ser Val
    50                  55                  60

Lys Gly Arg Phe Thr Ile Ser Lys Asp Asn Asp Arg Asn Thr Leu Tyr
65                  70                  75                  80

Leu Gln Met Asn Ser Leu Lys Pro Glu Asp Thr Ala Val Tyr Tyr Cys
                85                  90                  95

Ala Arg Ser Ser Ile Met Gly Ile Tyr Thr Thr Pro Arg Tyr Glu
            100                 105                 110

Tyr Trp Gly Gln Gly Thr Gln Val Thr Val Ser Ser Gly Gly Gly Gly
        115                 120                 125

Ser Asp Asp Asp Asp Lys Gly Gly Gly Gly Ser Glu Val Gln Leu Val
    130                 135                 140

Glu Ser Gly Gly Gly Leu Val Glu Ser Gly Ala Ser Leu Arg Leu Ser
145                 150                 155                 160

Cys Val Thr Ser Gly His Ile Phe Lys Leu Tyr Gly Met Gly Trp Phe
                165                 170                 175

Arg Gln Ala Pro Gly Lys Asp Arg Glu Phe Val Ala Ala Val Thr Trp
            180                 185                 190

Asn Gly Pro Ser Thr Glu Tyr Ala Asp Ser Val Lys Gly Arg Phe Thr
        195                 200                 205

Ile Ser Lys Asp Asn Asp Arg Asn Thr Leu Tyr Leu Gln Met Asn Ser
    210                 215                 220

Leu Lys Pro Glu Asp Thr Ala Val Tyr Tyr Cys Ala Arg Ser Ser Ile
225                 230                 235                 240

Met Gly Ile Tyr Thr Thr Pro Asp Arg Tyr Glu Tyr Trp Gly Gln Gly
                245                 250                 255

Thr Gln Val Thr Val Ser Ser
            260

<210> SEQ ID NO 16
<211> LENGTH: 260
<212> TYPE: PRT
<213> ORGANISM: Artificial Sequence
```

<220> FEATURE:
<223> OTHER INFORMATION: Polypeptide sequence of ID60F construct

<400> SEQUENCE: 16

Glu Val Gln Leu Val Glu Ser Gly Gly Gly Leu Val Glu Ser Gly Ala
1               5                   10                  15

Ser Leu Arg Leu Ser Cys Val Thr Ser Gly His Ile Phe Lys Leu Tyr
            20                  25                  30

Gly Met Gly Trp Phe Arg Gln Ala Pro Gly Lys Asp Arg Glu Phe Val
        35                  40                  45

Ala Ala Val Thr Trp Asn Gly Pro Ser Thr Glu Tyr Ala Asp Ser Val
    50                  55                  60

Lys Gly Arg Phe Thr Ile Ser Lys Asp Asn Asp Arg Asn Thr Leu Tyr
65                  70                  75                  80

Leu Gln Met Asn Ser Leu Lys Pro Glu Asp Thr Ala Val Tyr Tyr Cys
                85                  90                  95

Ala Arg Ser Ser Ile Met Gly Ile Tyr Thr Thr Pro Asp Arg Tyr Glu
            100                 105                 110

Tyr Trp Gly Gln Gly Thr Gln Val Thr Val Ser Ser Lys Gly Gly Gly
        115                 120                 125

Gly Ser Gly Gly Gly Ser Lys Glu Val Gln Leu Val Glu Ser Gly
    130                 135                 140

Gly Gly Leu Val Glu Ser Gly Ala Ser Leu Arg Leu Ser Cys Val Thr
145                 150                 155                 160

Ser Gly His Ile Phe Lys Leu Tyr Gly Met Gly Trp Phe Arg Gln Ala
                165                 170                 175

Pro Gly Lys Asp Arg Glu Phe Val Ala Ala Val Thr Trp Asn Gly Pro
            180                 185                 190

Ser Thr Glu Tyr Ala Asp Ser Val Lys Gly Arg Phe Thr Ile Ser Lys
        195                 200                 205

Asp Asn Asp Arg Asn Thr Leu Tyr Leu Gln Met Asn Ser Leu Lys Pro
    210                 215                 220

Glu Asp Thr Ala Val Tyr Tyr Cys Ala Arg Ser Ser Ile Met Gly Ile
225                 230                 235                 240

Tyr Thr Thr Pro Asp Arg Tyr Glu Tyr Trp Gly Gln Gly Thr Gln Val
                245                 250                 255

Thr Val Ser Ser
            260

<210> SEQ ID NO 17
<211> LENGTH: 261
<212> TYPE: PRT
<213> ORGANISM: Artificial Sequence
<220> FEATURE:
<223> OTHER INFORMATION: Polypeptide sequence of ID56F construct

<400> SEQUENCE: 17

Glu Val Gln Leu Val Glu Ser Gly Gly Gly Leu Val Glu Ser Gly Ala
1               5                   10                  15

Ser Leu Arg Leu Ser Cys Val Thr Ser Gly His Ile Phe Lys Leu Tyr
            20                  25                  30

Gly Met Gly Trp Phe Arg Gln Ala Pro Gly Lys Asp Arg Glu Phe Val
        35                  40                  45

Ala Ala Val Thr Trp Asn Gly Pro Ser Thr Glu Tyr Ala Asp Ser Val
    50                  55                  60

Lys Gly Arg Phe Thr Ile Ser Lys Asp Asn Asp Arg Asn Thr Leu Tyr

```
                65                  70                  75                  80
Leu Gln Met Asn Ser Leu Lys Pro Glu Asp Thr Ala Val Tyr Tyr Cys
                    85                  90                  95

Ala Arg Ser Ser Ile Met Gly Ile Tyr Thr Thr Pro Asp Arg Tyr Glu
                100                 105                 110

Tyr Trp Gly Gln Gly Thr Gln Val Thr Val Ser Ser Arg Gly Gly Gly
                115                 120                 125

Gly Ser Arg Gly Gly Gly Ser Arg Glu Val Gln Leu Val Glu Ser
130                 135                 140

Gly Gly Gly Leu Val Glu Ser Gly Ala Ser Leu Arg Leu Ser Cys Val
145                 150                 155                 160

Thr Ser Gly His Ile Phe Lys Leu Tyr Gly Met Gly Trp Phe Arg Gln
                165                 170                 175

Ala Pro Gly Lys Asp Arg Glu Phe Val Ala Ala Val Thr Trp Asn Gly
                180                 185                 190

Pro Ser Thr Glu Tyr Ala Asp Ser Val Lys Gly Arg Phe Thr Ile Ser
                195                 200                 205

Lys Asp Asn Asp Arg Asn Thr Leu Tyr Leu Gln Met Asn Ser Leu Lys
                210                 215                 220

Pro Glu Asp Thr Ala Val Tyr Tyr Cys Ala Arg Ser Ser Ile Met Gly
225                 230                 235                 240

Ile Tyr Thr Thr Pro Asp Arg Tyr Glu Tyr Trp Gly Gln Gly Thr Gln
                245                 250                 255

Val Thr Val Ser Ser
                260

<210> SEQ ID NO 18
<211> LENGTH: 111
<212> TYPE: PRT
<213> ORGANISM: Artificial Sequence
<220> FEATURE:
<223> OTHER INFORMATION: Polypeptide sequence of ID1A ICVD

<400> SEQUENCE: 18

Asp Val Gln Leu Gln Glu Ser Gly Gly Gly Leu Val Gln Pro Gly Gly
1               5                   10                  15

Ser Leu Arg Leu Ser Cys Val Ile Ser Gly Met Asp Phe Ser His Lys
                20                  25                  30

Pro Ala Gly Trp Phe Arg Gln Ala Pro Gly Lys Glu Arg Glu Phe Val
                35                  40                  45

Ala Ser Ile Thr Thr Arg Ala Ser Thr His Tyr Ala Asp Ser Val Lys
50                  55                  60

Gly Arg Phe Thr Ile Ser Arg Asp Asn Ala Lys Asn Thr Val Tyr Leu
65                  70                  75                  80

Glu Met Asn Ser Leu Lys Pro Glu Asp Thr Ala Val Tyr Ser Cys Asn
                85                  90                  95

Ser Glu Tyr Tyr Trp Gly Gln Gly Thr Gln Val Thr Val Ser Ser
                100                 105                 110

<210> SEQ ID NO 19
<211> LENGTH: 124
<212> TYPE: PRT
<213> ORGANISM: Artificial Sequence
<220> FEATURE:
<223> OTHER INFORMATION: Polypeptide sequence of ID5F ICVD

<400> SEQUENCE: 19
```

Asp Val Gln Leu Gln Glu Ser Gly Gly Leu Val Glu Ser Gly Ala
1               5                   10                  15

Ser Leu Arg Leu Ser Cys Val Thr Ser Gly His Ile Phe Lys Leu Tyr
            20                  25                  30

Gly Met Gly Trp Phe Arg Gln Ala Pro Gly Lys Asp Arg Glu Phe Val
        35                  40                  45

Ala Ala Val Thr Trp Asn Gly Pro Ser Thr Glu Tyr Ala Asp Ser Val
    50                  55                  60

Lys Gly Arg Phe Thr Ile Ser Lys Asp Asn Asp Arg Asn Thr Leu Tyr
65                  70                  75                  80

Leu Gln Met Asn Ser Leu Lys Pro Glu Asp Thr Ala Val Tyr Tyr Cys
                85                  90                  95

Ala Arg Ser Ser Ile Met Gly Ile Tyr Thr Thr Pro Asp Arg Tyr Glu
            100                 105                 110

Tyr Trp Gly Gln Gly Thr Gln Val Thr Val Ser Ser
        115                 120

<210> SEQ ID NO 20
<211> LENGTH: 732
<212> TYPE: DNA
<213> ORGANISM: Artificial Sequence
<220> FEATURE:
<223> OTHER INFORMATION: Polynucleotide sequence encoding ID3A construct

<400> SEQUENCE: 20
gatgtgcagc tgcaggagtc tgggggaggc ttggtgcagc ctggggggtc tctgagactc    60
tcctgtgtaa tctctggaat ggacttcagt cacaaacccg cgggctggtt ccgccaggct   120
ccaggaaaag agcgcgagtt cgtcgcttcg attacgactc gtgctagcac gcactatgca   180
gactccgtga agggccgatt caccatctcc agagacaacg ccaagaacac ggtatatcta   240
gaaatgaaca gcctgaaacc tgaggacacg gccgtctatt cttgtaactc gaatactac   300 tggggccagg gacccaggt caccgtctcc tcaggtggag gcggttcagg cggaggtggc   360
tctggcggtg gcggaagtgg tggaggcggt tcagatgtgc agctgcagga gtctggggga   420
ggcttggtgc agcctggggg gtctctgaga ctctcctgtg taatctctgg aatggacttc   480
agtcacaaac ccgcgggctg gttccgccag gctccaggaa aagagcgcga gttcgtcgct   540
tcgattacga ctcgtgctag cacgcactat gcagactccg tgaagggccg attcaccatc   600
tccagagaca acgccaagaa cacggtatat ctagaaatga acagcctgaa acctgaggac   660
acggccgtct attcttgtaa ctccgaatac tactggggcc aggggaccca ggtcaccgtc   720
tcctcataat ga                                                       732

<210> SEQ ID NO 21
<211> LENGTH: 705
<212> TYPE: DNA
<213> ORGANISM: Artificial Sequence
<220> FEATURE:
<223> OTHER INFORMATION: Polynucleotide sequence encoding ID25A
      construct

<400> SEQUENCE: 21
gatgtgcagc tgcaggagtc tgggggaggc ttggtgcagc ctggggggtc tctgagactc    60
tcctgtgtaa tctctggaat ggacttcagt cacaaacccg cgggctggtt ccgccaggct   120
ccaggaaaag agcgcgagtt cgtcgcttcg attacgactc gtgctagcac gcactatgca   180
gactccgtga agggccgatt caccatctcc agagacaacg ccaagaacac ggtatatcta   240

|  |  |  |  |  |
|---|---|---|---|---|
| gaaatgaaca | gcctgaaacc | tgaggacacg | gccgtctatt | cttgtaactc cgaatactac | 300 |
| tggggccagg | ggacccaggt | caccgtctcc | tcaggtggag | gcggttcaaa aggcggaggt | 360 |
| ggctctgatg | tgcagctgca | ggagtctggg | ggaggcttgg | tgcagcctgg ggggtctctg | 420 |
| agactctcct | gtgtaatctc | tggaatggac | ttcagtcaca | aacccgcggg ctggttccgc | 480 |
| caggctccag | gaaaagagcg | cgagttcgtc | gcttcgatta | cgactcgtgc tagcacgcac | 540 |
| tatgcagact | ccgtgaaggg | ccgattcacc | atctccagag | acaacgccaa gaacacggta | 600 |
| tatctagaaa | tgaacagcct | gaaacctgag | gacacggccg | tctattcttg taactccgaa | 660 |
| tactactggg | gccaggggac | ccaggtcacc | gtctcctcat | aatga | 705 |

<210> SEQ ID NO 22
<211> LENGTH: 711
<212> TYPE: DNA
<213> ORGANISM: Artificial Sequence
<220> FEATURE:
<223> OTHER INFORMATION: Polynucleotide sequence encoding ID26A construct

<400> SEQUENCE: 22

|  |  |  |  |  |  |
|---|---|---|---|---|---|
| gatgtgcagc | tgcaggagtc | tgggggaggc | ttggtgcagc | ctgggggtc tctgagactc | 60 |
| tcctgtgtaa | tctctggaat | ggacttcagt | cacaaacccg | cgggctggtt ccgccaggct | 120 |
| ccaggaaaag | agcgcgagtt | cgtcgcttcg | attacgactc | gtgctagcac gcactatgca | 180 |
| gactccgtga | agggccgatt | caccatctcc | agagacaacg | ccaagaacac ggtatatcta | 240 |
| gaaatgaaca | gcctgaaacc | tgaggacacg | gccgtctatt | cttgtaactc cgaatactac | 300 |
| tggggccagg | ggacccaggt | caccgtctcc | tcaggtggag | gcggttcaga taaagacggc | 360 |
| ggaggtggct | ctgatgtgca | gctgcaggag | tctgggggag | gcttggtgca gcctgggggg | 420 |
| tctctgagac | tctcctgtgt | aatctctgga | atggacttca | gtcacaaacc cgcgggctgg | 480 |
| ttccgccagg | ctccaggaaa | agagcgcgag | ttcgtcgctt | cgattacgac tcgtgctagc | 540 |
| acgcactatg | cagactccgt | gaagggccga | ttcaccatct | ccagagacaa cgccaagaac | 600 |
| acggtatatc | tagaaatgaa | cagcctgaaa | cctgaggaca | cggccgtcta ttcttgtaac | 660 |
| tccgaatact | actggggcca | ggggacccag | gtcaccgtct | cctcataatg a | 711 |

<210> SEQ ID NO 23
<211> LENGTH: 717
<212> TYPE: DNA
<213> ORGANISM: Artificial Sequence
<220> FEATURE:
<223> OTHER INFORMATION: Polynucleotide sequence encoding ID27A construct

<400> SEQUENCE: 23

|  |  |  |  |  |  |
|---|---|---|---|---|---|
| gatgtgcagc | tgcaggagtc | tgggggaggc | ttggtgcagc | ctgggggtc tctgagactc | 60 |
| tcctgtgtaa | tctctggaat | ggacttcagt | cacaaacccg | cgggctggtt ccgccaggct | 120 |
| ccaggaaaag | agcgcgagtt | cgtcgcttcg | attacgactc | gtgctagcac gcactatgca | 180 |
| gactccgtga | agggccgatt | caccatctcc | agagacaacg | ccaagaacac ggtatatcta | 240 |
| gaaatgaaca | gcctgaaacc | tgaggacacg | gccgtctatt | cttgtaactc cgaatactac | 300 |
| tggggccagg | ggacccaggt | caccgtctcc | tcaggtggag | gcggttcaga tgacgacgat | 360 |
| aaaggcggag | gtggctctga | tgtgcagctg | caggagtctg | ggggaggctt ggtgcagcct | 420 |
| gggggtctc | tgagactctc | ctgtgtaatc | tctggaatgg | acttcagtca caaacccgcg | 480 |
| ggctggttcc | gccaggctcc | aggaaaagag | cgcgagttcg | tcgcttcgat tacgactcgt | 540 |

```
gctagcacgc actatgcaga ctccgtgaag ggccgattca ccatctccag agacaacgcc    600
aagaacacgg tatatctaga aatgaacagc ctgaaacctg aggacacggc cgtctattct    660
tgtaactccg aatactactg gggccagggg acccaggtca ccgtctcctc ataatga       717
```

<210> SEQ ID NO 24
<211> LENGTH: 708
<212> TYPE: DNA
<213> ORGANISM: Artificial Sequence
<220> FEATURE:
<223> OTHER INFORMATION: Polynucleotide sequence encoding ID28A
      construct

<400> SEQUENCE: 24

```
gatgtgcagc tgcaggagtc tgggggaggc ttggtgcagc ctgggggtc tctgagactc      60 tcctgtgtaa tctctggaat ggacttcagt cacaaacccg cgggctggtt ccgccaggct    120
ccaggaaaag agcgcgagtt cgtcgcttcg attacgactc gtgctagcac gcactatgca    180
gactccgtga agggccgatt caccatctcc agagacaacc caagaacac ggtatatcta    240 gaaatgaaca gcctgaaacc tgaggacacg gccgtctatt cttgtaactc gaatactac    300 tggggccagg gacccaggt caccgtctcc tcaaaaggtg gaggcggttc aggcggaggt    360
ggctctaagg atgtgcagct gcaggagtct gggggaggct tggtgcagcc tggggggtct    420
ctgagactct cctgtgtaat ctctggaatg gacttcagtc acaaacccgc gggctggttc    480
cgccaggctc aggaaaaga gcgcgagttc gtcgcttcga ttacgactcg tgctagcacg    540
cactatgcag actccgtgaa gggccgattc accatctcca gagacaacgc caagaacacg    600
gtatatctag aaatgaacag cctgaaacct gaggacacgg ccgtctattc ttgtaactcc    660
gaatactact ggggccaggg gacccaggtc accgtctcct cataatga                 708
```

<210> SEQ ID NO 25
<211> LENGTH: 810
<212> TYPE: DNA
<213> ORGANISM: Artificial Sequence
<220> FEATURE:
<223> OTHER INFORMATION: Polynucleotide sequence encoding ID55F
      construct

<400> SEQUENCE: 25

```
gaggtgcagc tggtggagtc tgggggagga ttggttgaga gtggggcctc tctgagactc     60
tcctgtgtaa cctctggaca tatcttcaag ttgtatggca tgggctggtt ccggcaggct    120
cccgggaagg accgtgagtt cgtagcggct gttacatgaa acggtccgag cacagagtac    180
gcagactccg tgaagggccg attcaccatc tccaaggaca cgacaggaa cacgctgtat    240 ctgcaaatga acagcctgaa acctgaggac acggccgttt attactgtgc acgaagttcc    300
ataatgggaa tatatactac ccccgacaga tacgaatact ggggccaggg acccaagtc    360 accgtctcct caggtggagg cggttcaggc ggaggtggct ctggcggtgg cggaagtggt    420
ggcggtggat cagaggtgca gctggtggag tctgggggag gattggttga gagtggggcc    480
tctctgagac tctcctgtgt aacctctgga catatcttca agttgtatgg catgggctgg    540
ttccggcagg ctcccgggaa ggaccgtgag ttcgtagcgg ctgttacatg aacggtccg     600 agcacagagt acgcagactc cgtgaagggc cgattcacca tctccaagga caacgacagg    660
aacacgctgt atctgcaaat gaacagcctg aaacctgagg acacggccgt ttattactgt    720
gcacgaagtt ccataatggg aatatatact accccccgaca gatacgaata ctggggccag    780
```

```
gggacccagg tcaccgtctc ctcataatga                                        810
```

<210> SEQ ID NO 26
<211> LENGTH: 783
<212> TYPE: DNA
<213> ORGANISM: Artificial Sequence
<220> FEATURE:
<223> OTHER INFORMATION: Polynucleotide sequence encoding ID57F
      construct

<400> SEQUENCE: 26

```
gaggtgcagc tggtggagtc tgggggagga ttggttgaga gtggggcctc tctgagactc        60
tcctgtgtaa cctctggaca tatcttcaag ttgtatggca tgggctggtt ccggcaggct       120
cccgggaagg accgtgagtt cgtagcggct gttacatgga acggtccgag cacagagtac       180
gcagactccg tgaagggccg attcaccatc tccaaggaca cgacaggaa cacgctgtat        240
ctgcaaatga acagcctgaa acctgaggac acggccgttt attactgtgc acgaagttcc       300
ataatgggaa tatatactac ccccgacaga tacgaatact ggggccaggg gacccaagtc       360
accgtctcct caggtggagg cggttcaaaa ggcggaggtg ctctgaggt gcagctggtg        420
gagtctgggg gaggattggt tgagagtggg gcctctctga ctctcctg tgtaacctct         480
ggacatatct tcaagttgta tggcatgggc tggttccggc aggctcccgg aaggaccgt        540
gagttcgtag cggctgttac atggaacggt ccgagcacag agtacgcaga ctccgtgaag       600
ggccgattca ccatctccaa ggacaacgac aggaacacgc tgtatctgca aatgaacagc       660
ctgaaacctg aggacacggc cgtttattac tgtgcacgaa gttccataat gggaatatat       720
actaccccg acagatacga atactggggc caggggaccc aggtcaccgt ctcctcataa        780
tga                                                                    783
```

<210> SEQ ID NO 27
<211> LENGTH: 789
<212> TYPE: DNA
<213> ORGANISM: Artificial Sequence
<220> FEATURE:
<223> OTHER INFORMATION: Polynucleotide sequence encoding ID58F
      construct

<400> SEQUENCE: 27

```
gaggtgcagc tggtggagtc tgggggagga ttggttgaga gtggggcctc tctgagactc        60
tcctgtgtaa cctctggaca tatcttcaag ttgtatggca tgggctggtt ccggcaggct       120
cccgggaagg accgtgagtt cgtagcggct gttacatgga acggtccgag cacagagtac       180
gcagactccg tgaagggccg attcaccatc tccaaggaca cgacaggaa cacgctgtat        240
ctgcaaatga acagcctgaa acctgaggac acggccgttt attactgtgc acgaagttcc       300
ataatgggaa tatatactac ccccgacaga tacgaatact ggggccaggg gacccaagtc       360
accgtctcct caggtggagg cggttcagat aaagatggcg gaggtggctc tgaggtgcag       420
ctggtggagt ctgggggagg attggttgag agtggggcct ctctgagact ctcctgtgta       480
acctctggac atatcttcaa gttgtatggc atgggctggt tccggcaggc tcccgggaag       540
gaccgtgagt tcgtagcggc tgttacatgg aacggtccga gcacagagta cgcagactcc       600
gtgaagggcc gattcaccat ctccaaggac aacgacagga acacgctgta tctgcaaatg       660
aacagcctga aacctgagga cacggccgtt tattactgtg cacgaagttc cataatggga       720
atatatacta ccccccgacag atacgaatac tggggccagg gacccaggt caccgtctcc       780
tcataatga                                                              789
```

<210> SEQ ID NO 28
<211> LENGTH: 795
<212> TYPE: DNA
<213> ORGANISM: Artificial Sequence
<220> FEATURE:
<223> OTHER INFORMATION: Polynucleotide sequence encoding ID59F
      construct

<400> SEQUENCE: 28

| | | | | | |
|---|---|---|---|---|---|
| gaggtgcagc | tggtggagtc | tgggggagga | ttggttgaga | gtggggcctc | tctgagactc | 60 |
| tcctgtgtaa | cctctggaca | tatcttcaag | ttgtatggca | tgggctggtt | ccggcaggct | 120 |
| cccgggaagg | accgtgagtt | cgtagcggct | gttacatgga | acggtccgag | cacagagtac | 180 |
| gcagactccg | tgaagggccg | attcaccatc | tccaaggaca | cgacaggaa | cacgctgtat | 240 |
| ctgcaaatga | acagcctgaa | acctgaggac | acggccgttt | attactgtgc | acgaagttcc | 300 |
| ataatgggaa | tatatactac | ccccgacaga | tacgaatact | ggggccaggg | gacccaagtc | 360 |
| accgtctcct | caggtggagg | cggttcagac | gatgacgata | aaggcggagg | tggctctgag | 420 |
| gtgcagctgg | tggagtctgg | gggaggattg | gttgagagtg | gggcctctct | gagactctcc | 480 |
| tgtgtaacct | ctggacatat | cttcaagttg | tatggcatgg | gctggttccg | gcaggctccc | 540 |
| gggaaggacc | gtgagttcgt | agcggctgtt | acatggaacg | gtccgagcac | agagtacgca | 600 |
| gactccgtga | agggccgatt | caccatctcc | aaggacaacg | acaggaacac | gctgtatctg | 660 |
| caaatgaaca | gcctgaaacc | tgaggacacg | gccgtttatt | actgtgcacg | aagttccata | 720 |
| atgggaatat | atactacccc | cgacagatac | gaatactggg | gccaggggac | ccaggtcacc | 780 |
| gtctcctcat | aatga | | | | | 795 |

<210> SEQ ID NO 29
<211> LENGTH: 786
<212> TYPE: DNA
<213> ORGANISM: Artificial Sequence
<220> FEATURE:
<223> OTHER INFORMATION: Polynucleotide sequence encoding ID60F
      construct

<400> SEQUENCE: 29

| | | | | | |
|---|---|---|---|---|---|
| gaggtgcagc | tggtggagtc | tgggggagga | ttggttgaga | gtggggcctc | tctgagactc | 60 |
| tcctgtgtaa | cctctggaca | tatcttcaag | ttgtatggca | tgggctggtt | ccggcaggct | 120 |
| cccgggaagg | accgtgagtt | cgtagcggct | gttacatgga | acggtccgag | cacagagtac | 180 |
| gcagactccg | tgaagggccg | attcaccatc | tccaaggaca | cgacaggaa | cacgctgtat | 240 |
| ctgcaaatga | acagcctgaa | acctgaggac | acggccgttt | attactgtgc | acgaagttcc | 300 |
| ataatgggaa | tatatactac | ccccgacaga | tacgaatact | ggggccaggg | gacccaagtc | 360 |
| accgtctcct | caaaaggtgg | aggcggttca | ggcggaggtg | gctctaaaga | ggtgcagctg | 420 |
| gtggagtctg | ggggaggatt | ggttgagagt | ggggcctctc | tgagactctc | ctgtgtaacc | 480 |
| tctggacata | tcttcaagtt | gtatggcatg | ggctggttcc | ggcaggctcc | cgggaaggac | 540 |
| cgtgagttcg | tagcggctgt | tacatggaac | ggtccgagca | cagagtacgc | agactccgtg | 600 |
| aagggccgat | tcaccatctc | caaggacaac | gacaggaaca | cgctgtatct | gcaaatgaac | 660 |
| agcctgaaac | ctgaggacac | ggccgtttat | tactgtgcac | gaagttccat | aatgggaata | 720 |
| tatactaccc | ccgacagata | cgaatactgg | ggccagggga | cccaggtcac | cgtctcctca | 780 |
| taatga | | | | | | 786 |

<210> SEQ ID NO 30
<211> LENGTH: 795
<212> TYPE: DNA
<213> ORGANISM: Artificial Sequence
<220> FEATURE:
<223> OTHER INFORMATION: Polynucleotide sequence encoding ID56F
      construct

<400> SEQUENCE: 30
gaggtgcagc tggtggagtc tgggggagga ttggttgaga gtggggcctc tctgagactc      60
tcctgtgtaa cctctggaca tatcttcaag ttgtatggca tgggctggtt ccggcaggct     120
cccgggaagg accgtgagtt cgtagcggct gttacatgga acgtccgag cacagagtac      180 gcagactccg tgaagggccg attcaccatc tccaaggaca cgacaggaa cacgctgtat      240 ctgcaaatga acagcctgaa acctgaggac acggccgttt attactgtgc acgaagttcc     300
ataatgggaa tatatactac ccccgacaga tacgaatact ggggccaggg acccaagtc      360 accgtctcct caggtggagg cggttcagac gatgacgata aggcggagg tggctctgag      420 gtgcagctgg tggagtctgg gggaggattg gttgagagtg gggcctctct gagactctcc     480
tgtgtaacct ctggacatat cttcaagttg tatggcatgg gctggttccg gcaggctccc    540
gggaaggacc gtgagttcgt agcggctgtt acatggaacg tccgagcac agagtacgca    600 gactccgtga agggccgatt caccatctcc aaggacaacg acaggaacac gctgtatctg    660
caaatgaaca gcctgaaacc tgaggacacg gccgtttatt actgtgcacg aagttccata    720
atgggaatat atactacccc cgacagatac gaatactggg gccaggggac ccaggtcacc    780
gtctcctcat aatga                                                      795

<210> SEQ ID NO 31
<211> LENGTH: 60
<212> TYPE: DNA
<213> ORGANISM: Artificial Sequence
<220> FEATURE:
<223> OTHER INFORMATION: Polynucleotide sequence encoding linker used in
      constructs ID3A and ID55F

<400> SEQUENCE: 31
ggtggtggtg gttctggtgg tggtggttct ggtggtggtg gttctggtgg tggtggttct      60

<210> SEQ ID NO 32
<211> LENGTH: 33
<212> TYPE: DNA
<213> ORGANISM: Artificial Sequence
<220> FEATURE:
<223> OTHER INFORMATION: Polynucleotide sequence encoding linker used in
      constructs ID25A and ID57F

<400> SEQUENCE: 32
ggtggtggtg gttctaaagg tggtggtggt tct                                   33

<210> SEQ ID NO 33
<211> LENGTH: 39
<212> TYPE: DNA
<213> ORGANISM: Artificial Sequence
<220> FEATURE:
<223> OTHER INFORMATION: Polynucleotide sequence encoding linker used in
      constructs ID26A and ID58F

<400> SEQUENCE: 33
ggtggtggtg gttctgataa agatggtggt ggtggttct                             39

-continued

```
<210> SEQ ID NO 34
<211> LENGTH: 45
<212> TYPE: DNA
<213> ORGANISM: Artificial Sequence
<220> FEATURE:
<223> OTHER INFORMATION: Polynucleotide sequence encoding linker used in
      constructs ID27A and ID59F

<400> SEQUENCE: 34
ggtggtggtg gttctgatga tgatgataaa ggtggtggtg gttct            45

<210> SEQ ID NO 35
<211> LENGTH: 36
<212> TYPE: DNA
<213> ORGANISM: Artificial Sequence
<220> FEATURE:
<223> OTHER INFORMATION: Polynucleotide sequence encoding linker used in
      constructs ID28A and ID60F

<400> SEQUENCE: 35
aaaggtggtg gtggttctgg tggtggtggt tctaaa                      36

<210> SEQ ID NO 36
<211> LENGTH: 39
<212> TYPE: DNA
<213> ORGANISM: Artificial Sequence
<220> FEATURE:
<223> OTHER INFORMATION: Polynucleotide sequence encoding linker used in
      construct ID56F

<400> SEQUENCE: 36
agaggtggtg gtggttctag aggtggtggt ggttctaga                   39

<210> SEQ ID NO 37
<211> LENGTH: 11
<212> TYPE: PRT
<213> ORGANISM: Artificial Sequence
<220> FEATURE:
<223> OTHER INFORMATION: Proposed chymotrypsin-labile linker

<400> SEQUENCE: 37

Gly Gly Gly Gly Ser Tyr Gly Gly Gly Gly Ser
1               5                   10

<210> SEQ ID NO 38
<211> LENGTH: 235
<212> TYPE: PRT
<213> ORGANISM: Artificial Sequence
<220> FEATURE:
<223> OTHER INFORMATION: Polypeptide sequence of ID4A construct

<400> SEQUENCE: 38

Asp Val Gln Leu Gln Glu Ser Gly Gly Gly Leu Val Gln Pro Gly Gly
1               5                   10                  15

Ser Leu Arg Leu Ser Cys Val Ile Ser Gly Met Asp Phe Ser His Lys
            20                  25                  30

Pro Ala Gly Trp Phe Arg Gln Ala Pro Gly Lys Glu Arg Glu Phe Val
        35                  40                  45

Ala Ser Ile Thr Thr Arg Ala Ser Thr His Tyr Ala Asp Ser Val Lys
    50                  55                  60

Gly Arg Phe Thr Ile Ser Arg Asp Asn Ala Lys Asn Thr Val Tyr Leu
65                  70                  75                  80

Glu Met Asn Ser Leu Lys Pro Glu Asp Thr Ala Val Tyr Ser Cys Asn
                85                  90                  95
```

```
Ser Glu Tyr Tyr Trp Gly Gln Gly Thr Gln Val Thr Val Ser Ser Arg
            100                 105                 110
Gly Gly Gly Gly Ser Arg Gly Gly Gly Ser Arg Asp Val Gln Leu
        115                 120                 125
Gln Glu Ser Gly Gly Leu Val Gln Pro Gly Gly Ser Leu Arg Leu
    130                 135                 140
Ser Cys Val Ile Ser Gly Met Asp Phe Ser His Lys Pro Ala Gly Trp
145                 150                 155                 160
Phe Arg Gln Ala Pro Gly Lys Glu Arg Glu Phe Val Ala Ser Ile Thr
                165                 170                 175
Thr Arg Ala Ser Thr His Tyr Ala Asp Ser Val Lys Gly Arg Phe Thr
            180                 185                 190
Ile Ser Arg Asp Asn Ala Lys Asn Thr Val Tyr Leu Glu Met Asn Ser
        195                 200                 205
Leu Lys Pro Glu Asp Thr Ala Val Tyr Ser Cys Asn Ser Glu Tyr Tyr
    210                 215                 220
Trp Gly Gln Gly Thr Gln Val Thr Val Ser Ser
225                 230                 235

<210> SEQ ID NO 39
<211> LENGTH: 2210
<212> TYPE: PRT
<213> ORGANISM: Artificial Sequence
<220> FEATURE:
<223> OTHER INFORMATION: Description of Artificial Sequence: Synthetic
      labile peptide linker
<220> FEATURE:
<221> NAME/KEY: MISC_FEATURE
<222> LOCATION: (1)..(10)
<223> OTHER INFORMATION: This region may encompass 1-10 residues
<220> FEATURE:
<221> NAME/KEY: MISC_FEATURE
<222> LOCATION: (12)..(21)
<223> OTHER INFORMATION: This region may encompass 1-10 residues
<220> FEATURE:
<221> NAME/KEY: MISC_FEATURE
<222> LOCATION: (23)..(32)
<223> OTHER INFORMATION: This region may encompass 1-10 residues
<220> FEATURE:
<221> NAME/KEY: MISC_FEATURE
<222> LOCATION: (34)..(43)
<223> OTHER INFORMATION: This region may encompass 1-10 residues
<220> FEATURE:
<221> NAME/KEY: MISC_FEATURE
<222> LOCATION: (45)..(54)
<223> OTHER INFORMATION: This region may encompass 1-10 residues
<220> FEATURE:
<221> NAME/KEY: MISC_FEATURE
<222> LOCATION: (56)..(65)
<223> OTHER INFORMATION: This region may encompass 1-10 residues
<220> FEATURE:
<221> NAME/KEY: MISC_FEATURE
<222> LOCATION: (67)..(76)
<223> OTHER INFORMATION: This region may encompass 1-10 residues
<220> FEATURE:
<221> NAME/KEY: MISC_FEATURE
<222> LOCATION: (78)..(87)
<223> OTHER INFORMATION: This region may encompass 1-10 residues
<220> FEATURE:
<221> NAME/KEY: MISC_FEATURE
<222> LOCATION: (89)..(98)
<223> OTHER INFORMATION: This region may encompass 1-10 residues
<220> FEATURE:
<221> NAME/KEY: MISC_FEATURE
<222> LOCATION: (100)..(109)
<223> OTHER INFORMATION: This region may encompass 1-10 residues
<220> FEATURE:
<221> NAME/KEY: MOD_RES
<222> LOCATION: (111)..(111)
<223> OTHER INFORMATION: K or R
```

```
<220> FEATURE:
<221> NAME/KEY: MISC_FEATURE
<222> LOCATION: (112)..(121)
<223> OTHER INFORMATION: This region may encompass 1-10 residues
<220> FEATURE:
<221> NAME/KEY: MISC_FEATURE
<222> LOCATION: (123)..(132)
<223> OTHER INFORMATION: This region may encompass 1-10 residues
<220> FEATURE:
<221> NAME/KEY: MISC_FEATURE
<222> LOCATION: (134)..(143)
<223> OTHER INFORMATION: This region may encompass 1-10 residues
<220> FEATURE:
<221> NAME/KEY: MISC_FEATURE
<222> LOCATION: (145)..(154)
<223> OTHER INFORMATION: This region may encompass 1-10 residues
<220> FEATURE:
<221> NAME/KEY: MISC_FEATURE
<222> LOCATION: (156)..(165)
<223> OTHER INFORMATION: This region may encompass 1-10 residues
<220> FEATURE:
<221> NAME/KEY: MISC_FEATURE
<222> LOCATION: (167)..(176)
<223> OTHER INFORMATION: This region may encompass 1-10 residues
<220> FEATURE:
<221> NAME/KEY: MISC_FEATURE
<222> LOCATION: (178)..(187)
<223> OTHER INFORMATION: This region may encompass 1-10 residues
<220> FEATURE:
<221> NAME/KEY: MISC_FEATURE
<222> LOCATION: (189)..(198)
<223> OTHER INFORMATION: This region may encompass 1-10 residues
<220> FEATURE:
<221> NAME/KEY: MISC_FEATURE
<222> LOCATION: (200)..(209)
<223> OTHER INFORMATION: This region may encompass 1-10 residues
<220> FEATURE:
<221> NAME/KEY: MISC_FEATURE
<222> LOCATION: (211)..(220)
<223> OTHER INFORMATION: This region may encompass 1-10 residues
<220> FEATURE:
<221> NAME/KEY: MISC_FEATURE
<222> LOCATION: (222)..(231)
<223> OTHER INFORMATION: This region may encompass 1-10 residues
<220> FEATURE:
<221> NAME/KEY: MISC_FEATURE
<222> LOCATION: (233)..(242)
<223> OTHER INFORMATION: This region may encompass 1-10 residues
<220> FEATURE:
<221> NAME/KEY: MISC_FEATURE
<222> LOCATION: (244)..(253)
<223> OTHER INFORMATION: This region may encompass 1-10 residues
<220> FEATURE:
<221> NAME/KEY: MISC_FEATURE
<222> LOCATION: (255)..(264)
<223> OTHER INFORMATION: This region may encompass 1-10 residues
<220> FEATURE:
<221> NAME/KEY: MISC_FEATURE
<222> LOCATION: (266)..(275)
<223> OTHER INFORMATION: This region may encompass 1-10 residues
<220> FEATURE:
<221> NAME/KEY: MISC_FEATURE
<222> LOCATION: (277)..(286)
<223> OTHER INFORMATION: This region may encompass 1-10 residues
<220> FEATURE:
<221> NAME/KEY: MISC_FEATURE
<222> LOCATION: (288)..(297)
<223> OTHER INFORMATION: This region may encompass 1-10 residues
<220> FEATURE:
<221> NAME/KEY: MISC_FEATURE
<222> LOCATION: (299)..(308)
<223> OTHER INFORMATION: This region may encompass 1-10 residues
<220> FEATURE:
<221> NAME/KEY: MISC_FEATURE
<222> LOCATION: (310)..(319)
<223> OTHER INFORMATION: This region may encompass 1-10 residues
<220> FEATURE:
<221> NAME/KEY: MISC_FEATURE
<222> LOCATION: (321)..(330)
```

```
<223> OTHER INFORMATION: This region may encompass 1-10 residues
<220> FEATURE:
<221> NAME/KEY: MOD_RES
<222> LOCATION: (332)..(332)
<223> OTHER INFORMATION: K or R
<220> FEATURE:
<221> NAME/KEY: MISC_FEATURE
<222> LOCATION: (333)..(342)
<223> OTHER INFORMATION: This region may encompass 1-10 residues
<220> FEATURE:
<221> NAME/KEY: MISC_FEATURE
<222> LOCATION: (344)..(353)
<223> OTHER INFORMATION: This region may encompass 1-10 residues
<220> FEATURE:
<221> NAME/KEY: MISC_FEATURE
<222> LOCATION: (355)..(364)
<223> OTHER INFORMATION: This region may encompass 1-10 residues
<220> FEATURE:
<221> NAME/KEY: MISC_FEATURE
<222> LOCATION: (366)..(375)
<223> OTHER INFORMATION: This region may encompass 1-10 residues
<220> FEATURE:
<221> NAME/KEY: MISC_FEATURE
<222> LOCATION: (377)..(386)
<223> OTHER INFORMATION: This region may encompass 1-10 residues
<220> FEATURE:
<221> NAME/KEY: MISC_FEATURE
<222> LOCATION: (388)..(397)
<223> OTHER INFORMATION: This region may encompass 1-10 residues
<220> FEATURE:
<221> NAME/KEY: MISC_FEATURE
<222> LOCATION: (399)..(408)
<223> OTHER INFORMATION: This region may encompass 1-10 residues
<220> FEATURE:
<221> NAME/KEY: MISC_FEATURE
<222> LOCATION: (410)..(419)
<223> OTHER INFORMATION: This region may encompass 1-10 residues
<220> FEATURE:
<221> NAME/KEY: MISC_FEATURE
<222> LOCATION: (421)..(430)
<223> OTHER INFORMATION: This region may encompass 1-10 residues
<220> FEATURE:
<221> NAME/KEY: MISC_FEATURE
<222> LOCATION: (432)..(441)
<223> OTHER INFORMATION: This region may encompass 1-10 residues
<220> FEATURE:
<221> NAME/KEY: MISC_FEATURE
<222> LOCATION: (443)..(452)
<223> OTHER INFORMATION: This region may encompass 1-10 residues
<220> FEATURE:
<221> NAME/KEY: MISC_FEATURE
<222> LOCATION: (454)..(463)
<223> OTHER INFORMATION: This region may encompass 1-10 residues
<220> FEATURE:
<221> NAME/KEY: MISC_FEATURE
<222> LOCATION: (465)..(474)
<223> OTHER INFORMATION: This region may encompass 1-10 residues
<220> FEATURE:
<221> NAME/KEY: MISC_FEATURE
<222> LOCATION: (476)..(485)
<223> OTHER INFORMATION: This region may encompass 1-10 residues
<220> FEATURE:
<221> NAME/KEY: MISC_FEATURE
<222> LOCATION: (487)..(496)
<223> OTHER INFORMATION: This region may encompass 1-10 residues
<220> FEATURE:
<221> NAME/KEY: MISC_FEATURE
<222> LOCATION: (498)..(507)
<223> OTHER INFORMATION: This region may encompass 1-10 residues
<220> FEATURE:
<221> NAME/KEY: MISC_FEATURE
<222> LOCATION: (509)..(518)
<223> OTHER INFORMATION: This region may encompass 1-10 residues
<220> FEATURE:
<221> NAME/KEY: MISC_FEATURE
<222> LOCATION: (520)..(529)
<223> OTHER INFORMATION: This region may encompass 1-10 residues
<220> FEATURE:
<221> NAME/KEY: MISC_FEATURE
```

```
<222> LOCATION: (531)..(540)
<223> OTHER INFORMATION: This region may encompass 1-10 residues
<220> FEATURE:
<221> NAME/KEY: MISC_FEATURE
<222> LOCATION: (542)..(551)
<223> OTHER INFORMATION: This region may encompass 1-10 residues
<220> FEATURE:
<221> NAME/KEY: MOD_RES
<222> LOCATION: (553)..(553)
<223> OTHER INFORMATION: K or R
<220> FEATURE:
<221> NAME/KEY: MISC_FEATURE
<222> LOCATION: (554)..(563)
<223> OTHER INFORMATION: This region may encompass 1-10 residues
<220> FEATURE:
<221> NAME/KEY: MISC_FEATURE
<222> LOCATION: (565)..(574)
<223> OTHER INFORMATION: This region may encompass 1-10 residues
<220> FEATURE:
<221> NAME/KEY: MISC_FEATURE
<222> LOCATION: (576)..(585)
<223> OTHER INFORMATION: This region may encompass 1-10 residues
<220> FEATURE:
<221> NAME/KEY: MISC_FEATURE
<222> LOCATION: (587)..(596)
<223> OTHER INFORMATION: This region may encompass 1-10 residues
<220> FEATURE:
<221> NAME/KEY: MISC_FEATURE
<222> LOCATION: (598)..(607)
<223> OTHER INFORMATION: This region may encompass 1-10 residues
<220> FEATURE:
<221> NAME/KEY: MISC_FEATURE
<222> LOCATION: (609)..(618)
<223> OTHER INFORMATION: This region may encompass 1-10 residues
<220> FEATURE:
<221> NAME/KEY: MISC_FEATURE
<222> LOCATION: (620)..(629)
<223> OTHER INFORMATION: This region may encompass 1-10 residues
<220> FEATURE:
<221> NAME/KEY: MISC_FEATURE
<222> LOCATION: (631)..(640)
<223> OTHER INFORMATION: This region may encompass 1-10 residues
<220> FEATURE:
<221> NAME/KEY: MISC_FEATURE
<222> LOCATION: (642)..(651)
<223> OTHER INFORMATION: This region may encompass 1-10 residues
<220> FEATURE:
<221> NAME/KEY: MISC_FEATURE
<222> LOCATION: (653)..(662)
<223> OTHER INFORMATION: This region may encompass 1-10 residues
<220> FEATURE:
<221> NAME/KEY: MISC_FEATURE
<222> LOCATION: (664)..(673)
<223> OTHER INFORMATION: This region may encompass 1-10 residues
<220> FEATURE:
<221> NAME/KEY: MISC_FEATURE
<222> LOCATION: (675)..(684)
<223> OTHER INFORMATION: This region may encompass 1-10 residues
<220> FEATURE:
<221> NAME/KEY: MISC_FEATURE
<222> LOCATION: (686)..(695)
<223> OTHER INFORMATION: This region may encompass 1-10 residues
<220> FEATURE:
<221> NAME/KEY: MISC_FEATURE
<222> LOCATION: (697)..(706)
<223> OTHER INFORMATION: This region may encompass 1-10 residues
<220> FEATURE:
<221> NAME/KEY: MISC_FEATURE
<222> LOCATION: (708)..(717)
<223> OTHER INFORMATION: This region may encompass 1-10 residues
<220> FEATURE:
<221> NAME/KEY: MISC_FEATURE
<222> LOCATION: (719)..(728)
<223> OTHER INFORMATION: This region may encompass 1-10 residues
<220> FEATURE:
<221> NAME/KEY: MISC_FEATURE
<222> LOCATION: (730)..(739)
<223> OTHER INFORMATION: This region may encompass 1-10 residues
<220> FEATURE:
```

```
<221> NAME/KEY: MISC_FEATURE
<222> LOCATION: (741)..(750)
<223> OTHER INFORMATION: This region may encompass 1-10 residues
<220> FEATURE:
<221> NAME/KEY: MISC_FEATURE
<222> LOCATION: (752)..(761)
<223> OTHER INFORMATION: This region may encompass 1-10 residues
<220> FEATURE:
<221> NAME/KEY: MISC_FEATURE
<222> LOCATION: (763)..(772)
<223> OTHER INFORMATION: This region may encompass 1-10 residues
<220> FEATURE:
<221> NAME/KEY: MOD_RES
<222> LOCATION: (774)..(774)
<223> OTHER INFORMATION: K or R
<220> FEATURE:
<221> NAME/KEY: MISC_FEATURE
<222> LOCATION: (775)..(784)
<223> OTHER INFORMATION: This region may encompass 1-10 residues
<220> FEATURE:
<221> NAME/KEY: MISC_FEATURE
<222> LOCATION: (786)..(795)
<223> OTHER INFORMATION: This region may encompass 1-10 residues
<220> FEATURE:
<221> NAME/KEY: MISC_FEATURE
<222> LOCATION: (797)..(806)
<223> OTHER INFORMATION: This region may encompass 1-10 residues
<220> FEATURE:
<221> NAME/KEY: MISC_FEATURE
<222> LOCATION: (808)..(817)
<223> OTHER INFORMATION: This region may encompass 1-10 residues
<220> FEATURE:
<221> NAME/KEY: MISC_FEATURE
<222> LOCATION: (819)..(828)
<223> OTHER INFORMATION: This region may encompass 1-10 residues
<220> FEATURE:
<221> NAME/KEY: MISC_FEATURE
<222> LOCATION: (830)..(839)
<223> OTHER INFORMATION: This region may encompass 1-10 residues
<220> FEATURE:
<221> NAME/KEY: MISC_FEATURE
<222> LOCATION: (841)..(850)
<223> OTHER INFORMATION: This region may encompass 1-10 residues
<220> FEATURE:
<221> NAME/KEY: MISC_FEATURE
<222> LOCATION: (852)..(861)
<223> OTHER INFORMATION: This region may encompass 1-10 residues
<220> FEATURE:
<221> NAME/KEY: MISC_FEATURE
<222> LOCATION: (863)..(872)
<223> OTHER INFORMATION: This region may encompass 1-10 residues
<220> FEATURE:
<221> NAME/KEY: MISC_FEATURE
<222> LOCATION: (874)..(883)
<223> OTHER INFORMATION: This region may encompass 1-10 residues
<220> FEATURE:
<221> NAME/KEY: MISC_FEATURE
<222> LOCATION: (885)..(894)
<223> OTHER INFORMATION: This region may encompass 1-10 residues
<220> FEATURE:
<221> NAME/KEY: MISC_FEATURE
<222> LOCATION: (896)..(905)
<223> OTHER INFORMATION: This region may encompass 1-10 residues
<220> FEATURE:
<221> NAME/KEY: MISC_FEATURE
<222> LOCATION: (907)..(916)
<223> OTHER INFORMATION: This region may encompass 1-10 residues
<220> FEATURE:
<221> NAME/KEY: MISC_FEATURE
<222> LOCATION: (918)..(927)
<223> OTHER INFORMATION: This region may encompass 1-10 residues
<220> FEATURE:
<221> NAME/KEY: MISC_FEATURE
<222> LOCATION: (929)..(938)
<223> OTHER INFORMATION: This region may encompass 1-10 residues
<220> FEATURE:
<221> NAME/KEY: MISC_FEATURE
<222> LOCATION: (940)..(949)
<223> OTHER INFORMATION: This region may encompass 1-10 residues
```

-continued

```
<220> FEATURE:
<221> NAME/KEY: MISC_FEATURE
<222> LOCATION: (951)..(960)
<223> OTHER INFORMATION: This region may encompass 1-10 residues
<220> FEATURE:
<221> NAME/KEY: MISC_FEATURE
<222> LOCATION: (962)..(971)
<223> OTHER INFORMATION: This region may encompass 1-10 residues
<220> FEATURE:
<221> NAME/KEY: MISC_FEATURE
<222> LOCATION: (973)..(982)
<223> OTHER INFORMATION: This region may encompass 1-10 residues
<220> FEATURE:
<221> NAME/KEY: MISC_FEATURE
<222> LOCATION: (984)..(993)
<223> OTHER INFORMATION: This region may encompass 1-10 residues
<220> FEATURE:
<221> NAME/KEY: MOD_RES
<222> LOCATION: (995)..(995)
<223> OTHER INFORMATION: K or R
<220> FEATURE:
<221> NAME/KEY: MISC_FEATURE
<222> LOCATION: (996)..(1005)
<223> OTHER INFORMATION: This region may encompass 1-10 residues
<220> FEATURE:
<221> NAME/KEY: MISC_FEATURE
<222> LOCATION: (1007)..(1016)
<223> OTHER INFORMATION: This region may encompass 1-10 residues
<220> FEATURE:
<221> NAME/KEY: MISC_FEATURE
<222> LOCATION: (1018)..(1027)
<223> OTHER INFORMATION: This region may encompass 1-10 residues
<220> FEATURE:
<221> NAME/KEY: MISC_FEATURE
<222> LOCATION: (1029)..(1038)
<223> OTHER INFORMATION: This region may encompass 1-10 residues
<220> FEATURE:
<221> NAME/KEY: MISC_FEATURE
<222> LOCATION: (1040)..(1049)
<223> OTHER INFORMATION: This region may encompass 1-10 residues
<220> FEATURE:
<221> NAME/KEY: MISC_FEATURE
<222> LOCATION: (1051)..(1060)
<223> OTHER INFORMATION: This region may encompass 1-10 residues
<220> FEATURE:
<221> NAME/KEY: MISC_FEATURE
<222> LOCATION: (1062)..(1071)
<223> OTHER INFORMATION: This region may encompass 1-10 residues
<220> FEATURE:
<221> NAME/KEY: MISC_FEATURE
<222> LOCATION: (1073)..(1082)
<223> OTHER INFORMATION: This region may encompass 1-10 residues
<220> FEATURE:
<221> NAME/KEY: MISC_FEATURE
<222> LOCATION: (1084)..(1093)
<223> OTHER INFORMATION: This region may encompass 1-10 residues
<220> FEATURE:
<221> NAME/KEY: MISC_FEATURE
<222> LOCATION: (1095)..(1104)
<223> OTHER INFORMATION: This region may encompass 1-10 residues
<220> FEATURE:
<221> NAME/KEY: MISC_FEATURE
<222> LOCATION: (1106)..(1115)
<223> OTHER INFORMATION: This region may encompass 1-10 residues
<220> FEATURE:
<221> NAME/KEY: MISC_FEATURE
<222> LOCATION: (1117)..(1126)
<223> OTHER INFORMATION: This region may encompass 1-10 residues
<220> FEATURE:
<221> NAME/KEY: MISC_FEATURE
<222> LOCATION: (1128)..(1137)
<223> OTHER INFORMATION: This region may encompass 1-10 residues
<220> FEATURE:
<221> NAME/KEY: MISC_FEATURE
<222> LOCATION: (1139)..(1148)
<223> OTHER INFORMATION: This region may encompass 1-10 residues
<220> FEATURE:
<221> NAME/KEY: MISC_FEATURE
<222> LOCATION: (1150)..(1159)
```

```
<223> OTHER INFORMATION: This region may encompass 1-10 residues
<220> FEATURE:
<221> NAME/KEY: MISC_FEATURE
<222> LOCATION: (1161)..(1170)
<223> OTHER INFORMATION: This region may encompass 1-10 residues
<220> FEATURE:
<221> NAME/KEY: MISC_FEATURE
<222> LOCATION: (1172)..(1181)
<223> OTHER INFORMATION: This region may encompass 1-10 residues
<220> FEATURE:
<221> NAME/KEY: MISC_FEATURE
<222> LOCATION: (1183)..(1192)
<223> OTHER INFORMATION: This region may encompass 1-10 residues
<220> FEATURE:
<221> NAME/KEY: MISC_FEATURE
<222> LOCATION: (1194)..(1203)
<223> OTHER INFORMATION: This region may encompass 1-10 residues
<220> FEATURE:
<221> NAME/KEY: MISC_FEATURE
<222> LOCATION: (1205)..(1214)
<223> OTHER INFORMATION: This region may encompass 1-10 residues
<220> FEATURE:
<221> NAME/KEY: MOD_RES
<222> LOCATION: (1216)..(1216)
<223> OTHER INFORMATION: K or R
<220> FEATURE:
<221> NAME/KEY: MISC_FEATURE
<222> LOCATION: (1217)..(1226)
<223> OTHER INFORMATION: This region may encompass 1-10 residues
<220> FEATURE:
<221> NAME/KEY: MISC_FEATURE
<222> LOCATION: (1228)..(1237)
<223> OTHER INFORMATION: This region may encompass 1-10 residues
<220> FEATURE:
<221> NAME/KEY: MISC_FEATURE
<222> LOCATION: (1239)..(1248)
<223> OTHER INFORMATION: This region may encompass 1-10 residues
<220> FEATURE:
<221> NAME/KEY: MISC_FEATURE
<222> LOCATION: (1250)..(1259)
<223> OTHER INFORMATION: This region may encompass 1-10 residues
<220> FEATURE:
<221> NAME/KEY: MISC_FEATURE
<222> LOCATION: (1261)..(1270)
<223> OTHER INFORMATION: This region may encompass 1-10 residues
<220> FEATURE:
<221> NAME/KEY: MISC_FEATURE
<222> LOCATION: (1272)..(1281)
<223> OTHER INFORMATION: This region may encompass 1-10 residues
<220> FEATURE:
<221> NAME/KEY: MISC_FEATURE
<222> LOCATION: (1283)..(1292)
<223> OTHER INFORMATION: This region may encompass 1-10 residues
<220> FEATURE:
<221> NAME/KEY: MISC_FEATURE
<222> LOCATION: (1294)..(1303)
<223> OTHER INFORMATION: This region may encompass 1-10 residues
<220> FEATURE:
<221> NAME/KEY: MISC_FEATURE
<222> LOCATION: (1305)..(1314)
<223> OTHER INFORMATION: This region may encompass 1-10 residues
<220> FEATURE:
<221> NAME/KEY: MISC_FEATURE
<222> LOCATION: (1316)..(1325)
<223> OTHER INFORMATION: This region may encompass 1-10 residues
<220> FEATURE:
<221> NAME/KEY: MISC_FEATURE
<222> LOCATION: (1327)..(1336)
<223> OTHER INFORMATION: This region may encompass 1-10 residues
<220> FEATURE:
<221> NAME/KEY: MISC_FEATURE
<222> LOCATION: (1338)..(1347)
<223> OTHER INFORMATION: This region may encompass 1-10 residues
<220> FEATURE:
<221> NAME/KEY: MISC_FEATURE
<222> LOCATION: (1349)..(1358)
<223> OTHER INFORMATION: This region may encompass 1-10 residues
<220> FEATURE:
<221> NAME/KEY: MISC_FEATURE
```

```
<222> LOCATION: (1360)..(1369)
<223> OTHER INFORMATION: This region may encompass 1-10 residues
<220> FEATURE:
<221> NAME/KEY: MISC_FEATURE
<222> LOCATION: (1371)..(1380)
<223> OTHER INFORMATION: This region may encompass 1-10 residues
<220> FEATURE:
<221> NAME/KEY: MISC_FEATURE
<222> LOCATION: (1382)..(1391)
<223> OTHER INFORMATION: This region may encompass 1-10 residues
<220> FEATURE:
<221> NAME/KEY: MISC_FEATURE
<222> LOCATION: (1393)..(1402)
<223> OTHER INFORMATION: This region may encompass 1-10 residues
<220> FEATURE:
<221> NAME/KEY: MISC_FEATURE
<222> LOCATION: (1404)..(1413)
<223> OTHER INFORMATION: This region may encompass 1-10 residues
<220> FEATURE:
<221> NAME/KEY: MISC_FEATURE
<222> LOCATION: (1415)..(1424)
<223> OTHER INFORMATION: This region may encompass 1-10 residues
<220> FEATURE:
<221> NAME/KEY: MISC_FEATURE
<222> LOCATION: (1426)..(1435)
<223> OTHER INFORMATION: This region may encompass 1-10 residues
<220> FEATURE:
<221> NAME/KEY: MOD_RES
<222> LOCATION: (1437)..(1437)
<223> OTHER INFORMATION: K or R
<220> FEATURE:
<221> NAME/KEY: MISC_FEATURE
<222> LOCATION: (1438)..(1447)
<223> OTHER INFORMATION: This region may encompass 1-10 residues
<220> FEATURE:
<221> NAME/KEY: MISC_FEATURE
<222> LOCATION: (1449)..(1458)
<223> OTHER INFORMATION: This region may encompass 1-10 residues
<220> FEATURE:
<221> NAME/KEY: MISC_FEATURE
<222> LOCATION: (1460)..(1469)
<223> OTHER INFORMATION: This region may encompass 1-10 residues
<220> FEATURE:
<221> NAME/KEY: MISC_FEATURE
<222> LOCATION: (1471)..(1480)
<223> OTHER INFORMATION: This region may encompass 1-10 residues
<220> FEATURE:
<221> NAME/KEY: MISC_FEATURE
<222> LOCATION: (1482)..(1491)
<223> OTHER INFORMATION: This region may encompass 1-10 residues
<220> FEATURE:
<221> NAME/KEY: MISC_FEATURE
<222> LOCATION: (1493)..(1502)
<223> OTHER INFORMATION: This region may encompass 1-10 residues
<220> FEATURE:
<221> NAME/KEY: MISC_FEATURE
<222> LOCATION: (1504)..(1513)
<223> OTHER INFORMATION: This region may encompass 1-10 residues
<220> FEATURE:
<221> NAME/KEY: MISC_FEATURE
<222> LOCATION: (1515)..(1524)
<223> OTHER INFORMATION: This region may encompass 1-10 residues
<220> FEATURE:
<221> NAME/KEY: MISC_FEATURE
<222> LOCATION: (1526)..(1535)
<223> OTHER INFORMATION: This region may encompass 1-10 residues
<220> FEATURE:
<221> NAME/KEY: MISC_FEATURE
<222> LOCATION: (1537)..(1546)
<223> OTHER INFORMATION: This region may encompass 1-10 residues
<220> FEATURE:
<221> NAME/KEY: MISC_FEATURE
<222> LOCATION: (1548)..(1557)
<223> OTHER INFORMATION: This region may encompass 1-10 residues
<220> FEATURE:
<221> NAME/KEY: MISC_FEATURE
<222> LOCATION: (1559)..(1568)
<223> OTHER INFORMATION: This region may encompass 1-10 residues
<220> FEATURE:
```

```
<221> NAME/KEY: MISC_FEATURE
<222> LOCATION: (1570)..(1579)
<223> OTHER INFORMATION: This region may encompass 1-10 residues
<220> FEATURE:
<221> NAME/KEY: MISC_FEATURE
<222> LOCATION: (1581)..(1590)
<223> OTHER INFORMATION: This region may encompass 1-10 residues
<220> FEATURE:
<221> NAME/KEY: MISC_FEATURE
<222> LOCATION: (1592)..(1601)
<223> OTHER INFORMATION: This region may encompass 1-10 residues
<220> FEATURE:
<221> NAME/KEY: MISC_FEATURE
<222> LOCATION: (1603)..(1612)
<223> OTHER INFORMATION: This region may encompass 1-10 residues
<220> FEATURE:
<221> NAME/KEY: MISC_FEATURE
<222> LOCATION: (1614)..(1623)
<223> OTHER INFORMATION: This region may encompass 1-10 residues
<220> FEATURE:
<221> NAME/KEY: MISC_FEATURE
<222> LOCATION: (1625)..(1634)
<223> OTHER INFORMATION: This region may encompass 1-10 residues
<220> FEATURE:
<221> NAME/KEY: MISC_FEATURE
<222> LOCATION: (1636)..(1645)
<223> OTHER INFORMATION: This region may encompass 1-10 residues
<220> FEATURE:
<221> NAME/KEY: MISC_FEATURE
<222> LOCATION: (1647)..(1656)
<223> OTHER INFORMATION: This region may encompass 1-10 residues
<220> FEATURE:
<221> NAME/KEY: MOD_RES
<222> LOCATION: (1658)..(1658)
<223> OTHER INFORMATION: K or R
<220> FEATURE:
<221> NAME/KEY: MISC_FEATURE
<222> LOCATION: (1659)..(1668)
<223> OTHER INFORMATION: This region may encompass 1-10 residues
<220> FEATURE:
<221> NAME/KEY: MISC_FEATURE
<222> LOCATION: (1670)..(1679)
<223> OTHER INFORMATION: This region may encompass 1-10 residues
<220> FEATURE:
<221> NAME/KEY: MISC_FEATURE
<222> LOCATION: (1681)..(1690)
<223> OTHER INFORMATION: This region may encompass 1-10 residues
<220> FEATURE:
<221> NAME/KEY: MISC_FEATURE
<222> LOCATION: (1692)..(1701)
<223> OTHER INFORMATION: This region may encompass 1-10 residues
<220> FEATURE:
<221> NAME/KEY: MISC_FEATURE
<222> LOCATION: (1703)..(1712)
<223> OTHER INFORMATION: This region may encompass 1-10 residues
<220> FEATURE:
<221> NAME/KEY: MISC_FEATURE
<222> LOCATION: (1714)..(1723)
<223> OTHER INFORMATION: This region may encompass 1-10 residues
<220> FEATURE:
<221> NAME/KEY: MISC_FEATURE
<222> LOCATION: (1725)..(1734)
<223> OTHER INFORMATION: This region may encompass 1-10 residues
<220> FEATURE:
<221> NAME/KEY: MISC_FEATURE
<222> LOCATION: (1736)..(1745)
<223> OTHER INFORMATION: This region may encompass 1-10 residues
<220> FEATURE:
<221> NAME/KEY: MISC_FEATURE
<222> LOCATION: (1747)..(1756)
<223> OTHER INFORMATION: This region may encompass 1-10 residues
<220> FEATURE:
<221> NAME/KEY: MISC_FEATURE
<222> LOCATION: (1758)..(1767)
<223> OTHER INFORMATION: This region may encompass 1-10 residues
<220> FEATURE:
<221> NAME/KEY: MISC_FEATURE
<222> LOCATION: (1769)..(1778)
<223> OTHER INFORMATION: This region may encompass 1-10 residues
```

```
<220> FEATURE:
<221> NAME/KEY: MISC_FEATURE
<222> LOCATION: (1780)..(1789)
<223> OTHER INFORMATION: This region may encompass 1-10 residues
<220> FEATURE:
<221> NAME/KEY: MISC_FEATURE
<222> LOCATION: (1791)..(1800)
<223> OTHER INFORMATION: This region may encompass 1-10 residues
<220> FEATURE:
<221> NAME/KEY: MISC_FEATURE
<222> LOCATION: (1802)..(1811)
<223> OTHER INFORMATION: This region may encompass 1-10 residues
<220> FEATURE:
<221> NAME/KEY: MISC_FEATURE
<222> LOCATION: (1813)..(1822)
<223> OTHER INFORMATION: This region may encompass 1-10 residues
<220> FEATURE:
<221> NAME/KEY: MISC_FEATURE
<222> LOCATION: (1824)..(1833)
<223> OTHER INFORMATION: This region may encompass 1-10 residues
<220> FEATURE:
<221> NAME/KEY: MISC_FEATURE
<222> LOCATION: (1835)..(1844)
<223> OTHER INFORMATION: This region may encompass 1-10 residues
<220> FEATURE:
<221> NAME/KEY: MISC_FEATURE
<222> LOCATION: (1846)..(1855)
<223> OTHER INFORMATION: This region may encompass 1-10 residues
<220> FEATURE:
<221> NAME/KEY: MISC_FEATURE
<222> LOCATION: (1857)..(1866)
<223> OTHER INFORMATION: This region may encompass 1-10 residues
<220> FEATURE:
<221> NAME/KEY: MISC_FEATURE
<222> LOCATION: (1868)..(1877)
<223> OTHER INFORMATION: This region may encompass 1-10 residues
<220> FEATURE:
<221> NAME/KEY: MOD_RES
<222> LOCATION: (1879)..(1879)
<223> OTHER INFORMATION: K or R
<220> FEATURE:
<221> NAME/KEY: MISC_FEATURE
<222> LOCATION: (1880)..(1889)
<223> OTHER INFORMATION: This region may encompass 1-10 residues
<220> FEATURE:
<221> NAME/KEY: MISC_FEATURE
<222> LOCATION: (1891)..(1900)
<223> OTHER INFORMATION: This region may encompass 1-10 residues
<220> FEATURE:
<221> NAME/KEY: MISC_FEATURE
<222> LOCATION: (1902)..(1911)
<223> OTHER INFORMATION: This region may encompass 1-10 residues
<220> FEATURE:
<221> NAME/KEY: MISC_FEATURE
<222> LOCATION: (1913)..(1922)
<223> OTHER INFORMATION: This region may encompass 1-10 residues
<220> FEATURE:
<221> NAME/KEY: MISC_FEATURE
<222> LOCATION: (1924)..(1933)
<223> OTHER INFORMATION: This region may encompass 1-10 residues
<220> FEATURE:
<221> NAME/KEY: MISC_FEATURE
<222> LOCATION: (1935)..(1944)
<223> OTHER INFORMATION: This region may encompass 1-10 residues
<220> FEATURE:
<221> NAME/KEY: MISC_FEATURE
<222> LOCATION: (1946)..(1955)
<223> OTHER INFORMATION: This region may encompass 1-10 residues
<220> FEATURE:
<221> NAME/KEY: MISC_FEATURE
<222> LOCATION: (1957)..(1966)
<223> OTHER INFORMATION: This region may encompass 1-10 residues
<220> FEATURE:
<221> NAME/KEY: MISC_FEATURE
<222> LOCATION: (1968)..(1977)
<223> OTHER INFORMATION: This region may encompass 1-10 residues
<220> FEATURE:
<221> NAME/KEY: MISC_FEATURE
<222> LOCATION: (1979)..(1988)
```

```
<223> OTHER INFORMATION: This region may encompass 1-10 residues
<220> FEATURE:
<221> NAME/KEY: MISC_FEATURE
<222> LOCATION: (1990)..(1999)
<223> OTHER INFORMATION: This region may encompass 1-10 residues
<220> FEATURE:
<221> NAME/KEY: MISC_FEATURE
<222> LOCATION: (2001)..(2010)
<223> OTHER INFORMATION: This region may encompass 1-10 residues
<220> FEATURE:
<221> NAME/KEY: MISC_FEATURE
<222> LOCATION: (2012)..(2021)
<223> OTHER INFORMATION: This region may encompass 1-10 residues
<220> FEATURE:
<221> NAME/KEY: MISC_FEATURE
<222> LOCATION: (2023)..(2032)
<223> OTHER INFORMATION: This region may encompass 1-10 residues
<220> FEATURE:
<221> NAME/KEY: MISC_FEATURE
<222> LOCATION: (2034)..(2043)
<223> OTHER INFORMATION: This region may encompass 1-10 residues
<220> FEATURE:
<221> NAME/KEY: MISC_FEATURE
<222> LOCATION: (2045)..(2054)
<223> OTHER INFORMATION: This region may encompass 1-10 residues
<220> FEATURE:
<221> NAME/KEY: MISC_FEATURE
<222> LOCATION: (2056)..(2065)
<223> OTHER INFORMATION: This region may encompass 1-10 residues
<220> FEATURE:
<221> NAME/KEY: MISC_FEATURE
<222> LOCATION: (2067)..(2076)
<223> OTHER INFORMATION: This region may encompass 1-10 residues
<220> FEATURE:
<221> NAME/KEY: MISC_FEATURE
<222> LOCATION: (2078)..(2087)
<223> OTHER INFORMATION: This region may encompass 1-10 residues
<220> FEATURE:
<221> NAME/KEY: MISC_FEATURE
<222> LOCATION: (2089)..(2098)
<223> OTHER INFORMATION: This region may encompass 1-10 residues
<220> FEATURE:
<221> NAME/KEY: MOD_RES
<222> LOCATION: (2100)..(2100)
<223> OTHER INFORMATION: K or R
<220> FEATURE:
<221> NAME/KEY: MISC_FEATURE
<222> LOCATION: (2101)..(2110)
<223> OTHER INFORMATION: This region may encompass 1-10 residues
<220> FEATURE:
<221> NAME/KEY: MISC_FEATURE
<222> LOCATION: (2112)..(2121)
<223> OTHER INFORMATION: This region may encompass 1-10 residues
<220> FEATURE:
<221> NAME/KEY: MISC_FEATURE
<222> LOCATION: (2123)..(2132)
<223> OTHER INFORMATION: This region may encompass 1-10 residues
<220> FEATURE:
<221> NAME/KEY: MISC_FEATURE
<222> LOCATION: (2134)..(2143)
<223> OTHER INFORMATION: This region may encompass 1-10 residues
<220> FEATURE:
<221> NAME/KEY: MISC_FEATURE
<222> LOCATION: (2145)..(2154)
<223> OTHER INFORMATION: This region may encompass 1-10 residues
<220> FEATURE:
<221> NAME/KEY: MISC_FEATURE
<222> LOCATION: (2156)..(2165)
<223> OTHER INFORMATION: This region may encompass 1-10 residues
<220> FEATURE:
<221> NAME/KEY: MISC_FEATURE
<222> LOCATION: (2167)..(2176)
<223> OTHER INFORMATION: This region may encompass 1-10 residues
<220> FEATURE:
<221> NAME/KEY: MISC_FEATURE
<222> LOCATION: (2178)..(2187)
<223> OTHER INFORMATION: This region may encompass 1-10 residues
<220> FEATURE:
<221> NAME/KEY: MISC_FEATURE
```

```
<222> LOCATION: (2189)..(2198)
<223> OTHER INFORMATION: This region may encompass 1-10 residues
<220> FEATURE:
<221> NAME/KEY: MISC_FEATURE
<222> LOCATION: (2200)..(2209)
<223> OTHER INFORMATION: This region may encompass 1-10 residues
<220> FEATURE:
<221> NAME/KEY: MISC_FEATURE
<222> LOCATION: (1)..(2210)
<223> OTHER INFORMATION: This sequence may encompass 1-10
      "(GaS)x-B-(GbS)y" repeating units wherein a is 1 to
      10 b is 1 to 10 x is 1 to 10, and y is 1 to 10.
<220> FEATURE:
<223> OTHER INFORMATION: See specification as filed for detailed
      description of substitutions and preferred embodiments

<400> SEQUENCE: 39

Gly Gly Gly Gly Gly Gly Gly Gly Gly Ser Gly Gly Gly Gly
1               5                   10                  15

Gly Gly Gly Gly Gly Ser Gly Gly Gly Gly Gly Gly Gly Gly
                20                  25                  30

Ser Gly Gly Gly Gly Gly Gly Gly Gly Ser Gly Gly Gly Gly
        35                  40                  45

Gly Gly Gly Gly Gly Ser Gly Gly Gly Gly Gly Gly Gly Gly
50                  55                  60

Gly Ser Gly Gly Gly Gly Gly Gly Gly Gly Ser Gly Gly Gly
65              70                  75                  80

Gly Gly Gly Gly Gly Gly Ser Gly Gly Gly Gly Gly Gly Gly
                85                  90                  95

Gly Gly Ser Gly Gly Gly Gly Gly Gly Gly Gly Ser Xaa Gly
            100                 105                 110

Gly Gly Gly Gly Gly Gly Gly Gly Ser Gly Gly Gly Gly Gly
        115                 120                 125

Gly Gly Gly Gly Ser Gly Gly Gly Gly Gly Gly Gly Gly Ser
130                 135                 140

Gly Gly Gly Gly Gly Gly Gly Gly Ser Gly Gly Gly Gly Gly
145                 150                 155                 160

Gly Gly Gly Gly Gly Ser Gly Gly Gly Gly Gly Gly Gly Gly
                165                 170                 175

Ser Gly Gly Gly Gly Gly Gly Gly Gly Ser Gly Gly Gly Gly
            180                 185                 190

Gly Gly Gly Gly Gly Ser Gly Gly Gly Gly Gly Gly Gly Gly
        195                 200                 205

Gly Ser Gly Gly Gly Gly Gly Gly Gly Gly Ser Gly Gly Gly
210                 215                 220

Gly Gly Gly Gly Gly Gly Ser Gly Gly Gly Gly Gly Gly Gly
225                 230                 235                 240

Gly Gly Ser Gly Gly Gly Gly Gly Gly Gly Gly Ser Gly Gly
                245                 250                 255

Gly Gly Gly Gly Gly Gly Gly Ser Gly Gly Gly Gly Gly Gly
            260                 265                 270

Gly Gly Gly Ser Gly Gly Gly Gly Gly Gly Gly Gly Ser Gly
        275                 280                 285

Gly Gly Gly Gly Gly Gly Gly Ser Gly Gly Gly Gly Gly Gly
    290                 295                 300

Gly Gly Gly Gly Ser Gly Gly Gly Gly Gly Gly Gly Gly Ser
305                 310                 315                 320

Gly Gly Gly Gly Gly Gly Gly Gly Gly Ser Xaa Gly Gly Gly Gly
```

```
                325                 330                 335
Gly Gly Gly Gly Gly Ser Gly Gly Gly Gly Gly Gly Gly
            340                 345                 350
Gly Ser Gly Gly Gly Gly Gly Gly Gly Gly Ser Gly Gly
            355                 360                 365
Gly Gly Gly Gly Gly Gly Ser Gly Gly Gly Gly Gly Gly
            370                 375                 380
Gly Gly Ser Gly Gly Gly Gly Gly Gly Gly Ser Gly Gly
385                 390                 395                 400
Gly Gly Gly Gly Gly Gly Gly Ser Gly Gly Gly Gly Gly
            405                 410                 415
Gly Gly Gly Ser Gly Gly Gly Gly Gly Gly Gly Ser Gly
            420                 425                 430
Gly Gly Gly Gly Gly Gly Gly Ser Gly Gly Gly Gly Gly
            435                 440                 445
Gly Gly Gly Gly Ser Gly Gly Gly Gly Gly Gly Gly Ser
            450                 455                 460
Gly Gly Gly Gly Gly Gly Gly Gly Ser Gly Gly Gly Gly
465                 470                 475                 480
Gly Gly Gly Gly Gly Ser Gly Gly Gly Gly Gly Gly Gly
            485                 490                 495
Ser Gly Gly Gly Gly Gly Gly Gly Gly Ser Gly Gly Gly
            500                 505                 510
Gly Gly Gly Gly Gly Ser Gly Gly Gly Gly Gly Gly Gly
            515                 520                 525
Gly Ser Gly Gly Gly Gly Gly Gly Gly Gly Ser Gly Gly
            530                 535                 540
Gly Gly Gly Gly Gly Gly Ser Xaa Gly Gly Gly Gly Gly
545                 550                 555                 560
Gly Gly Gly Ser Gly Gly Gly Gly Gly Gly Gly Ser Gly
            565                 570                 575
Gly Gly Gly Gly Gly Gly Gly Gly Ser Gly Gly Gly Gly
            580                 585                 590
Gly Gly Gly Gly Ser Gly Gly Gly Gly Gly Gly Gly Ser
            595                 600                 605
Gly Gly Gly Gly Gly Gly Gly Gly Ser Gly Gly Gly Gly
            610                 615                 620
Gly Gly Gly Gly Gly Ser Gly Gly Gly Gly Gly Gly Gly
625                 630                 635                 640
Ser Gly Gly Gly Gly Gly Gly Gly Gly Ser Gly Gly Gly
            645                 650                 655
Gly Gly Gly Gly Gly Ser Gly Gly Gly Gly Gly Gly Gly
            660                 665                 670
Gly Ser Gly Gly Gly Gly Gly Gly Gly Gly Ser Gly Gly
            675                 680                 685
Gly Gly Gly Gly Gly Gly Gly Ser Gly Gly Gly Gly Gly
            690                 695                 700
Gly Gly Ser Gly Gly Gly Gly Gly Gly Gly Gly Ser Gly Gly
705                 710                 715                 720
Gly Gly Gly Gly Gly Gly Gly Ser Gly Gly Gly Gly Gly
            725                 730                 735
Gly Gly Gly Ser Gly Gly Gly Gly Gly Gly Gly Ser Gly
            740                 745                 750
```

-continued

```
Gly Gly Gly Gly Gly Gly Gly Ser Gly Gly Gly Gly Gly
        755                 760             765
Gly Gly Gly Gly Ser Xaa Gly Gly Gly Gly Gly Gly Gly
    770             775                 780
Ser Gly Gly Gly Gly Gly Gly Gly Gly Ser Gly Gly Gly
785                 790                 795         800
Gly Gly Gly Gly Gly Ser Gly Gly Gly Gly Gly Gly Gly
            805                 810             815
Gly Ser Gly Gly Gly Gly Gly Gly Gly Gly Ser Gly Gly
        820                 825                 830
Gly Gly Gly Gly Gly Gly Ser Gly Gly Gly Gly Gly Gly
        835                 840                 845
Gly Gly Ser Gly Gly Gly Gly Gly Gly Gly Gly Ser Gly Gly
        850                 855                 860
Gly Gly Gly Gly Gly Gly Ser Gly Gly Gly Gly Gly Gly
865                 870                 875         880
Gly Gly Gly Ser Gly Gly Gly Gly Gly Gly Gly Ser Gly
            885                 890                 895
Gly Gly Gly Gly Gly Gly Gly Ser Gly Gly Gly Gly Gly
        900                 905                 910
Gly Gly Gly Gly Ser Gly Gly Gly Gly Gly Gly Gly Ser
        915                 920                 925
Gly Gly Gly Gly Gly Gly Gly Ser Gly Gly Gly Gly Gly
        930                 935                 940
Gly Gly Gly Gly Ser Gly Gly Gly Gly Gly Gly Gly Gly
945                 950                 955         960
Ser Gly Gly Gly Gly Gly Gly Gly Gly Ser Gly Gly Gly
        965                 970                 975
Gly Gly Gly Gly Gly Gly Ser Gly Gly Gly Gly Gly Gly Gly
        980                 985                 990
Gly Ser Xaa Gly Gly Gly Gly Gly Gly Gly Gly Ser Gly Gly
        995                 1000                1005
Gly Gly  Gly Gly Gly Gly Gly  Gly Ser Gly Gly Gly  Gly Gly Gly
    1010                1015                1020
Gly Gly  Gly Gly Ser Gly Gly  Gly Gly Gly Gly Gly  Gly Gly Gly
    1025                1030                1035
Ser Gly  Gly Gly Gly Gly Gly  Gly Gly Gly Gly Ser  Gly Gly Gly
    1040                1045                1050
Gly Gly  Gly Gly Gly Gly Gly  Ser Gly Gly Gly Gly  Gly Gly Gly
    1055                1060                1065
Gly Gly  Gly Ser Gly Gly Gly  Gly Gly Gly Gly Gly  Gly Gly Ser
    1070                1075                1080
Gly Gly  Gly Gly Gly Gly Gly  Gly Gly Gly Ser Gly  Gly Gly Gly
    1085                1090                1095
Gly Gly  Gly Gly Gly Gly Ser  Gly Gly Gly Gly Gly  Gly Gly Gly
    1100                1105                1110
Gly Gly  Ser Gly Gly Gly Gly  Gly Gly Gly Gly Gly  Gly Ser Gly
    1115                1120                1125
Gly Gly  Gly Gly Gly Gly Gly  Gly Gly Ser Gly Gly  Gly Gly Gly
    1130                1135                1140
Gly Gly  Gly Gly Gly Ser Gly  Gly Gly Gly Gly Gly  Gly Gly
    1145                1150                1155
```

```
Gly Ser Gly Gly Gly Gly Gly Gly Gly Gly Gly Ser Gly Gly
    1160                1165                1170

Gly Gly Gly Gly Gly Gly Gly Gly Ser Gly Gly Gly Gly Gly
    1175                1180                1185

Gly Gly Gly Gly Ser Gly Gly Gly Gly Gly Gly Gly Gly Gly
    1190                1195                1200

Ser Gly Gly Gly Gly Gly Gly Gly Gly Gly Ser Xaa Gly Gly
    1205                1210                1215

Gly Gly Gly Gly Gly Gly Gly Ser Gly Gly Gly Gly Gly Gly
    1220                1225                1230

Gly Gly Gly Gly Ser Gly Gly Gly Gly Gly Gly Gly Gly Gly
    1235                1240                1245

Ser Gly Gly Gly Gly Gly Gly Gly Gly Gly Ser Gly Gly Gly
    1250                1255                1260

Gly Gly Gly Gly Gly Gly Gly Ser Gly Gly Gly Gly Gly Gly
    1265                1270                1275

Gly Gly Gly Ser Gly Gly Gly Gly Gly Gly Gly Gly Gly Ser
    1280                1285                1290

Gly Gly Gly Gly Gly Gly Gly Gly Gly Ser Gly Gly Gly Gly
    1295                1300                1305

Gly Gly Gly Gly Gly Gly Ser Gly Gly Gly Gly Gly Gly Gly
    1310                1315                1320

Gly Gly Ser Gly Gly Gly Gly Gly Gly Gly Gly Gly Ser Gly
    1325                1330                1335

Gly Gly Gly Gly Gly Gly Gly Gly Ser Gly Gly Gly Gly Gly
    1340                1345                1350

Gly Gly Gly Gly Ser Gly Gly Gly Gly Gly Gly Gly Gly Gly
    1355                1360                1365

Gly Ser Gly Gly Gly Gly Gly Gly Gly Gly Gly Ser Gly Gly
    1370                1375                1380

Gly Gly Gly Gly Gly Gly Gly Ser Gly Gly Gly Gly Gly Gly
    1385                1390                1395

Gly Gly Gly Gly Ser Gly Gly Gly Gly Gly Gly Gly Gly Gly
    1400                1405                1410

Ser Gly Gly Gly Gly Gly Gly Gly Gly Gly Ser Gly Gly Gly
    1415                1420                1425

Gly Gly Gly Gly Gly Gly Gly Ser Xaa Gly Gly Gly Gly Gly
    1430                1435                1440

Gly Gly Gly Gly Ser Gly Gly Gly Gly Gly Gly Gly Gly Gly
    1445                1450                1455

Ser Gly Gly Gly Gly Gly Gly Gly Gly Gly Ser Gly Gly Gly
    1460                1465                1470

Gly Gly Gly Gly Gly Gly Gly Ser Gly Gly Gly Gly Gly Gly
    1475                1480                1485

Gly Gly Gly Ser Gly Gly Gly Gly Gly Gly Gly Gly Gly Ser
    1490                1495                1500

Gly Gly Gly Gly Gly Gly Gly Gly Gly Ser Gly Gly Gly Gly
    1505                1510                1515

Gly Gly Gly Gly Gly Gly Ser Gly Gly Gly Gly Gly Gly Gly
    1520                1525                1530

Gly Gly Ser Gly Gly Gly Gly Gly Gly Gly Gly Gly Ser Gly
    1535                1540                1545

Gly Gly Gly Gly Gly Gly Gly Gly Gly Ser Gly Gly Gly Gly Gly
```

-continued

```
            1550                1555                1560

Gly Gly Gly Gly Gly Ser  Gly Gly Gly Gly Gly  Gly Gly Gly
            1565                1570                1575

Gly Ser Gly Gly Gly Gly  Gly Gly Gly Gly Gly  Ser Gly Gly
            1580                1585                1590

Gly Gly Gly Gly Gly Gly  Gly Ser Gly Gly Gly  Gly Gly Gly
            1595                1600                1605

Gly Gly Gly Gly Ser Gly  Gly Gly Gly Gly Gly  Gly Gly Gly
            1610                1615                1620

Ser Gly Gly Gly Gly Gly  Gly Gly Gly Gly Ser  Gly Gly Gly
            1625                1630                1635

Gly Gly Gly Gly Gly Gly  Gly Ser Gly Gly Gly  Gly Gly Gly
            1640                1645                1650

Gly Gly Gly Ser Xaa Gly  Gly Gly Gly Gly Gly  Gly Gly Gly
            1655                1660                1665

Ser Gly Gly Gly Gly Gly  Gly Gly Gly Gly Ser  Gly Gly Gly
            1670                1675                1680

Gly Gly Gly Gly Gly Gly  Gly Ser Gly Gly Gly  Gly Gly Gly
            1685                1690                1695

Gly Gly Gly Ser Gly Gly  Gly Gly Gly Gly Gly  Gly Gly Ser
            1700                1705                1710

Gly Gly Gly Gly Gly Gly  Gly Gly Gly Ser Gly  Gly Gly Gly
            1715                1720                1725

Gly Gly Gly Gly Gly Ser  Gly Gly Gly Gly Gly  Gly Gly Gly
            1730                1735                1740

Gly Gly Ser Gly Gly Gly  Gly Gly Gly Gly Gly  Gly Ser Gly
            1745                1750                1755

Gly Gly Gly Gly Gly Gly  Gly Gly Ser Gly Gly  Gly Gly Gly
            1760                1765                1770

Gly Gly Gly Gly Gly Ser  Gly Gly Gly Gly Gly  Gly Gly Gly
            1775                1780                1785

Gly Ser Gly Gly Gly Gly  Gly Gly Gly Gly Gly  Ser Gly Gly
            1790                1795                1800

Gly Gly Gly Gly Gly Gly  Gly Ser Gly Gly Gly  Gly Gly Gly
            1805                1810                1815

Gly Gly Gly Gly Ser Gly  Gly Gly Gly Gly Gly  Gly Gly Gly
            1820                1825                1830

Ser Gly Gly Gly Gly Gly  Gly Gly Gly Gly Ser  Gly Gly Gly
            1835                1840                1845

Gly Gly Gly Gly Gly Gly  Gly Ser Gly Gly Gly  Gly Gly Gly
            1850                1855                1860

Gly Gly Gly Ser Gly Gly  Gly Gly Gly Gly Gly  Gly Gly Ser
            1865                1870                1875

Xaa Gly Gly Gly Gly Gly  Gly Gly Gly Gly Ser  Gly Gly Gly
            1880                1885                1890

Gly Gly Gly Gly Gly Gly  Gly Ser Gly Gly Gly  Gly Gly Gly
            1895                1900                1905

Gly Gly Gly Ser Gly Gly  Gly Gly Gly Gly Gly  Gly Gly Ser
            1910                1915                1920

Gly Gly Gly Gly Gly Gly  Gly Gly Gly Ser Gly  Gly Gly Gly
            1925                1930                1935

Gly Gly Gly Gly Gly Gly  Ser Gly Gly Gly Gly  Gly Gly Gly
            1940                1945                1950
```

Gly Gly Ser Gly Gly Gly Gly Gly Gly Gly Gly Ser Gly
     1955                1960                1965

Gly Gly Gly Gly Gly Gly Gly Gly Ser Gly Gly Gly Gly
     1970                1975                1980

Gly Gly Gly Gly Gly Ser Gly Gly Gly Gly Gly Gly Gly
     1985                1990                1995

Gly Ser Gly Gly Gly Gly Gly Gly Gly Gly Ser Gly Gly
     2000                2005                2010

Gly Gly Gly Gly Gly Gly Gly Ser Gly Gly Gly Gly Gly
     2015                2020                2025

Gly Gly Gly Gly Ser Gly Gly Gly Gly Gly Gly Gly Gly
     2030                2035                2040

Ser Gly Gly Gly Gly Gly Gly Gly Gly Gly Ser Gly Gly
     2045                2050                2055

Gly Gly Gly Gly Gly Gly Gly Ser Gly Gly Gly Gly Gly
     2060                2065                2070

Gly Gly Gly Ser Gly Gly Gly Gly Gly Gly Gly Gly Ser
     2075                2080                2085

Gly Gly Gly Gly Gly Gly Gly Gly Gly Ser Xaa Gly Gly Gly
     2090                2095                2100

Gly Gly Gly Gly Gly Gly Gly Ser Gly Gly Gly Gly Gly Gly
     2105                2110                2115

Gly Gly Gly Ser Gly Gly Gly Gly Gly Gly Gly Gly Ser
     2120                2125                2130

Gly Gly Gly Gly Gly Gly Gly Gly Ser Gly Gly Gly Gly
     2135                2140                2145

Gly Gly Gly Gly Gly Gly Ser Gly Gly Gly Gly Gly Gly Gly
     2150                2155                2160

Gly Gly Ser Gly Gly Gly Gly Gly Gly Gly Gly Ser Gly
     2165                2170                2175

Gly Gly Gly Gly Gly Gly Gly Gly Ser Gly Gly Gly Gly
     2180                2185                2190

Gly Gly Gly Gly Gly Ser Gly Gly Gly Gly Gly Gly Gly Gly
     2195                2200                2205

Gly Ser
     2210

<210> SEQ ID NO 40
<211> LENGTH: 112
<212> TYPE: PRT
<213> ORGANISM: Artificial Sequence
<220> FEATURE:
<223> OTHER INFORMATION: Description of Artificial Sequence: Synthetic
      labile peptide linker
<220> FEATURE:
<221> NAME/KEY: MOD_RES
<222> LOCATION: (1)..(1)
<223> OTHER INFORMATION: K or R
<220> FEATURE:
<221> NAME/KEY: MISC_FEATURE
<222> LOCATION: (2)..(11)
<223> OTHER INFORMATION: This region may encompass 1-10 residues
<220> FEATURE:
<221> NAME/KEY: MISC_FEATURE
<222> LOCATION: (13)..(22)
<223> OTHER INFORMATION: This region may encompass 1-10 residues
<220> FEATURE:
<221> NAME/KEY: MISC_FEATURE
<222> LOCATION: (24)..(33)
<223> OTHER INFORMATION: This region may encompass 1-10 residues

```
<220> FEATURE:
<221> NAME/KEY: MISC_FEATURE
<222> LOCATION: (35)..(44)
<223> OTHER INFORMATION: This region may encompass 1-10 residues
<220> FEATURE:
<221> NAME/KEY: MISC_FEATURE
<222> LOCATION: (46)..(55)
<223> OTHER INFORMATION: This region may encompass 1-10 residues
<220> FEATURE:
<221> NAME/KEY: MISC_FEATURE
<222> LOCATION: (57)..(66)
<223> OTHER INFORMATION: This region may encompass 1-10 residues
<220> FEATURE:
<221> NAME/KEY: MISC_FEATURE
<222> LOCATION: (68)..(77)
<223> OTHER INFORMATION: This region may encompass 1-10 residues
<220> FEATURE:
<221> NAME/KEY: MISC_FEATURE
<222> LOCATION: (79)..(88)
<223> OTHER INFORMATION: This region may encompass 1-10 residues
<220> FEATURE:
<221> NAME/KEY: MISC_FEATURE
<222> LOCATION: (90)..(99)
<223> OTHER INFORMATION: This region may encompass 1-10 residues
<220> FEATURE:
<221> NAME/KEY: MISC_FEATURE
<222> LOCATION: (101)..(110)
<223> OTHER INFORMATION: This region may encompass 1-10 residues
<220> FEATURE:
<221> NAME/KEY: MOD_RES
<222> LOCATION: (112)..(112)
<223> OTHER INFORMATION: K or R
<220> FEATURE:
<223> OTHER INFORMATION: See specification as filed for detailed
      description of substitutions and preferred embodiments

<400> SEQUENCE: 40

Xaa Gly Gly Gly Gly Gly Gly Gly Gly Ser Gly Gly Gly Gly Gly
1               5                   10                  15

Gly Gly Gly Gly Gly Gly Ser Gly Gly Gly Gly Gly Gly Gly Gly
            20                  25                  30

Gly Ser Gly Gly Gly Gly Gly Gly Gly Gly Ser Gly Gly Gly
        35                  40                  45

Gly Gly Gly Gly Gly Gly Ser Gly Gly Gly Gly Gly Gly Gly
    50                  55                  60

Gly Gly Ser Gly Gly Gly Gly Gly Gly Gly Gly Ser Gly Gly
65                  70                  75                  80

Gly Gly Gly Gly Gly Gly Ser Gly Gly Gly Gly Gly Gly Gly
            85                  90                  95

Gly Gly Gly Ser Gly Gly Gly Gly Gly Gly Gly Gly Ser Xaa
            100                 105                 110

<210> SEQ ID NO 41
<211> LENGTH: 23
<212> TYPE: PRT
<213> ORGANISM: Artificial Sequence
<220> FEATURE:
<223> OTHER INFORMATION: Description of Artificial Sequence: Synthetic
      labile peptide linker
<220> FEATURE:
<221> NAME/KEY: MISC_FEATURE
<222> LOCATION: (1)..(10)
<223> OTHER INFORMATION: This region may encompass 1-10 residues
<220> FEATURE:
<221> NAME/KEY: MOD_RES
<222> LOCATION: (12)..(12)
<223> OTHER INFORMATION: K or R
<220> FEATURE:
<221> NAME/KEY: MISC_FEATURE
<222> LOCATION: (13)..(22)
<223> OTHER INFORMATION: This region may encompass 1-10 residues
```

```
<220> FEATURE:
<223> OTHER INFORMATION: See specification as filed for detailed
      description of substitutions and preferred embodiments

<400> SEQUENCE: 41

Gly Gly Gly Gly Gly Gly Gly Gly Gly Gly Ser Xaa Gly Gly Gly Gly
1               5                   10                  15

Gly Gly Gly Gly Gly Gly Ser
            20

<210> SEQ ID NO 42
<211> LENGTH: 24
<212> TYPE: PRT
<213> ORGANISM: Artificial Sequence
<220> FEATURE:
<223> OTHER INFORMATION: Description of Artificial Sequence: Synthetic
      labile peptide linker
<220> FEATURE:
<221> NAME/KEY: MOD_RES
<222> LOCATION: (1)..(1)
<223> OTHER INFORMATION: K or R
<220> FEATURE:
<221> NAME/KEY: MISC_FEATURE
<222> LOCATION: (2)..(11)
<223> OTHER INFORMATION: This region may encompass 1-10 residues
<220> FEATURE:
<221> NAME/KEY: MISC_FEATURE
<222> LOCATION: (13)..(22)
<223> OTHER INFORMATION: This region may encompass 1-10 residues
<220> FEATURE:
<221> NAME/KEY: MOD_RES
<222> LOCATION: (24)..(24)
<223> OTHER INFORMATION: K or R
<220> FEATURE:
<223> OTHER INFORMATION: See specification as filed for detailed
      description of substitutions and preferred embodiments

<400> SEQUENCE: 42

Xaa Gly Gly Gly Gly Gly Gly Gly Gly Gly Gly Ser Gly Gly Gly Gly
1               5                   10                  15

Gly Gly Gly Gly Gly Gly Ser Xaa
            20
```

The invention claimed is:

1. A method of making a construct comprising a first VHH and a second VHH connected by a labile peptide linker, wherein:
   (i) the labile peptide linker is labile to one or more proteases present in the intestinal tract;
   (ii) the labile peptide linker is stable to yeast proteases;
   (iii) the labile peptide linker comprises of a polypeptide sequence of the format:

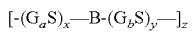
   $[-(G_aS)_x-B-(G_bS)_y-]_z$ wherein
   a is 3 to 5
   b is 3 to 5
   x is 1 or 2
   y is 1 or 2
   z is 1 to 3 and
   B is K; and
   (iv) wherein the construct comprises a first VHH and a second VHH;
   (v) wherein
   (a) the labile peptide linker is labile to one or more proteases present in the intestinal tract such that greater than 50% by mass of the construct is cleaved into first and second VHHs after 160 minutes after mixing in the Trypsin Protease Assay;
   (b) the labile peptide linker is stable to yeast proteases such that no more than 10% by mass of the construct is cleaved into first and second VHHs after producing the construct using the Yeast Expression Protocol; or
   (c) the first VHH and the second VHH are resistant to one or more proteases present in the intestinal tract such that at least 70% by mass of the first VHH and at least 70% by mass of the second VHH remain uncleaved after 10 minutes after mixing in the Trypsin Protease Assay;
   wherein the method comprises providing a host yeast cell capable of expressing the construct, producing the construct in the host yeast cell, and recovering the construct from the host yeast cell.

2. The method according claim 1, wherein the labile peptide linker is labile to one or more proteases present in the intestinal tract such that greater than 50% by mass of the construct is cleaved into first and second VHHs after 160 minutes after mixing in the Trypsin Protease Assay.

3. The method according to claim 1, wherein the labile peptide linker is stable to yeast proteases such that no more than 10% by mass of the construct is cleaved into first and second VHHs after producing the construct using the Yeast Expression Protocol.

4. The method according to claim 1, wherein the first VHH and the second VHH are resistant to one or more proteases present in the intestinal tract such that at least 70% by mass of the first VHH and at least 70% by mass of the second VHH remain uncleaved after 10 minutes after mixing in the Trypsin Protease Assay.

5. The method according to claim 1, wherein the one or more proteases are present in the small or large intestine.

6. The method according to claim 1, wherein the labile peptide linker comprises a cleavage site for trypsin or a trypsin-like protease.

7. The method according to claim 1, wherein the labile peptide linker comprises at least 1 K residue.

8. The method according to claim 1, wherein the labile peptide linker has a length of at least 3 residues.

9. The method according to claim 1, wherein the labile peptide linker has a length of no greater than 40 residues.

10. The method according to claim 1, wherein the labile peptide linker comprises of a polypeptide sequence of the format:

$$[-(G_aS)_x-B-(G_bS)_y-]_z$$

wherein
a is 4;
b is 4;
x is 1 or 2;
y is 1 or 2;
z is 1; and
B is K.

11. The method according to claim 1, wherein the labile peptide linker comprises SEQ ID NO: 2.

12. The method according to claim 11 wherein the labile peptide linker consists of SEQ ID NO: 2.

13. A method of making a construct comprising a first VHH and a second VHH connected by a labile peptide linker, wherein:
 (i) the labile peptide linker is labile to one or more proteases present in the intestinal tract;
 (ii) the labile peptide linker is stable to yeast proteases;
 (iii) the labile peptide linker comprises of a polypeptide sequence of the format:

$$[-(G_aS)_x-B-(G_bS)_y-]_z$$

wherein
a is 4;
b is 4;
x is 2;
y is 2;
z is 1; and
B is K; and
 (iv) the construct comprises a first VHH and a second VHH,
wherein the method comprises providing a host yeast cell capable of expressing the construct, producing the construct in the host yeast cell, and recovering the construct from the host yeast cell.

14. The method according to claim 13, wherein the labile peptide linker comprises at least 1 K residue.

15. The method according to claim 13, wherein the labile peptide linker has a length of no greater than 40 residues.

16. The method according to claim 13, wherein the labile peptide linker comprises SEQ ID NO: 2.

* * * * *